United States Patent
Littman et al.

(10) Patent No.: US 6,696,244 B2
(45) Date of Patent: *Feb. 24, 2004

(54) G-COUPLED RECEPTORS ASSOCIATED WITH RETROVIRAL ENTRY INTO CELLS, AND THERAPEUTIC USES THEREOF

(75) Inventors: Dan R. Littman, New York, NY (US); Hongkui Deng, Shrewsbury, MA (US); Derya Unutmaz, Nashville, TN (US); Vineet N. Kewalramani, Rockford, IL (US)

(73) Assignee: New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/852,156

(22) Filed: May 9, 2001

(65) Prior Publication Data

US 2002/0076694 A1 Jun. 20, 2002

Related U.S. Application Data

(63) Continuation-in-part of application No. 09/116,498, filed on Jul. 16, 1998, now Pat. No. 6,251,582.
(60) Provisional application No. 60/052,827, filed on Jul. 17, 1997.

(51) Int. Cl.[7] ............................ C12Q 1/70; C12Q 3/00; C12Q 1/00; C12Q 1/66; G01N 33/53
(52) U.S. Cl. ............... 435/5; 435/3; 435/4; 435/7.1; 435/7.2; 435/7.21; 435/8
(58) Field of Search ......................... 435/5, 3, 4, 7.1, 435/7.2, 7.21, 8

(56) References Cited

U.S. PATENT DOCUMENTS 6,251,582 B1 * 6/2001 Littman et al. ............... 435/5

OTHER PUBLICATIONS

Chen, Zhiwei et al., *J. Virol.*, vol. 71, No. 4 pp. 2705–2714 (1997).

Deng, Hongkui et al., *Nature*, vol. 381 pp. 661–666 (1996).

Deng, Hongkui et al., *Nature*, vol. 388 pp. 296–300 (1997).

Heiber, Michael et al., *Genomics*, vol 32 pp. 462–465 (1996).

Loetscher, M. et al., *Curr Biol*, vol. 7 pp. 652–660 (1997).

Qin, Shixin et al., *Eur J. Immunol.* vol. 26 pp. 640–647 (1996).

Stefano, Kelly A. et al., *J. Virol.*, vol. 67, No. 11 pp. 6707–6715 (1993).

Theodorou, Ioannis et al., *Lancet.*, vol. 349, pp. 1219–1220 (1997).

* cited by examiner

Primary Examiner—Hankyel T. Park
(74) Attorney, Agent, or Firm—Klauber & Jackson

(57) ABSTRACT

The present invention provides two new HIV/SIV translocation promoting agents, Bonzo and BOB. The present invention also provides the amino acid and DNA sequences of human, African green monkey, and pigtail macaque of the receptor protein Bonzo. Mammalian cells transfected with Bonzo and/or BOB and human CD4 as well as antibodies to the receptor Bonzo are also included. Furthermore, a method of identifying other such translocation promoting agents is also disclosed. Diagnostic and therapeutic uses of the translocation promoting agents of the present invention are also provided. Furthermore, the present invention provides methods of identifying agents that can modulate the expression and/or function of Bonzo/STRL33. Such agents can be used to either treat inflamation, or alternatively, to enhance the immune response.

15 Claims, 22 Drawing Sheets

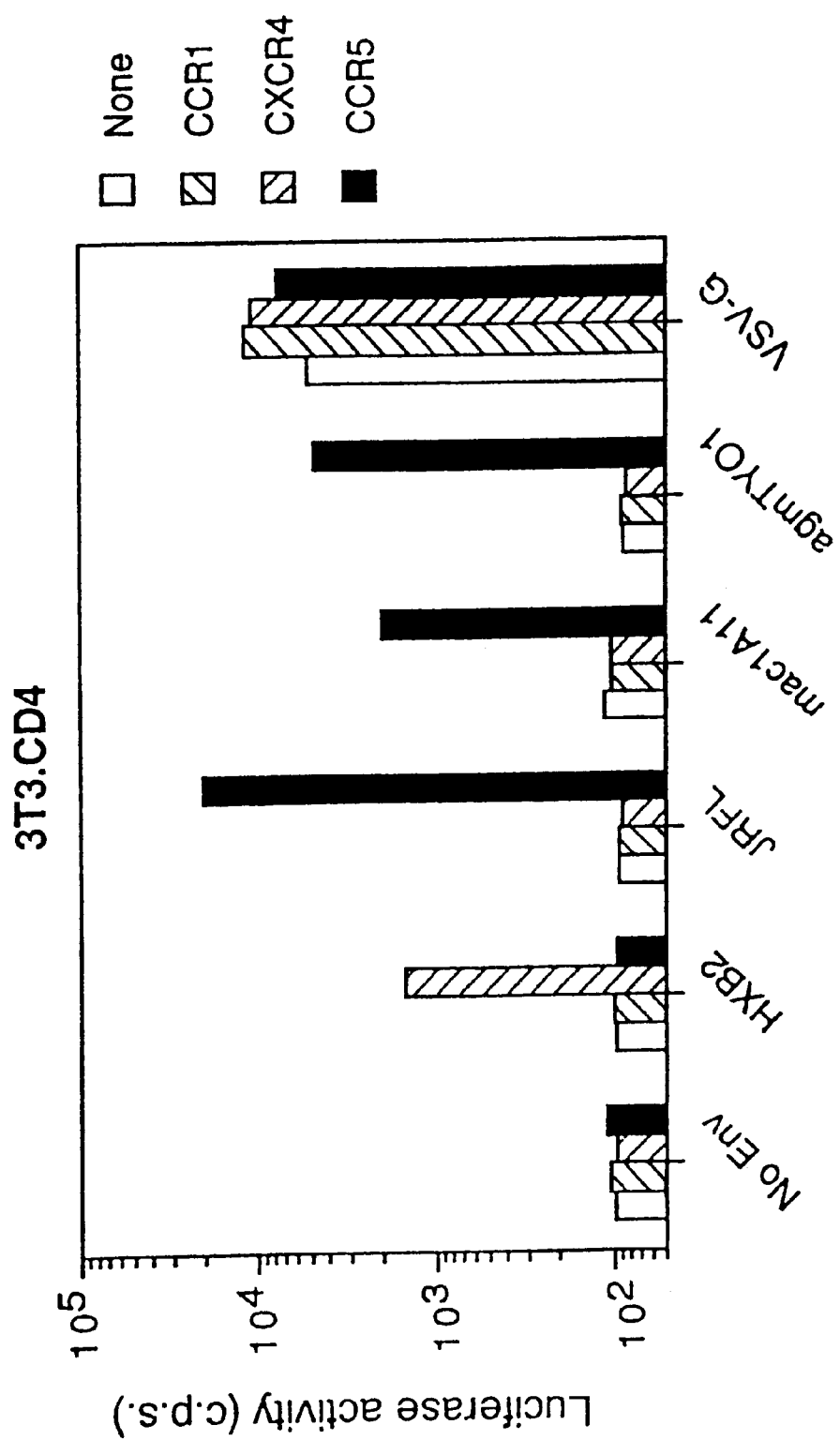

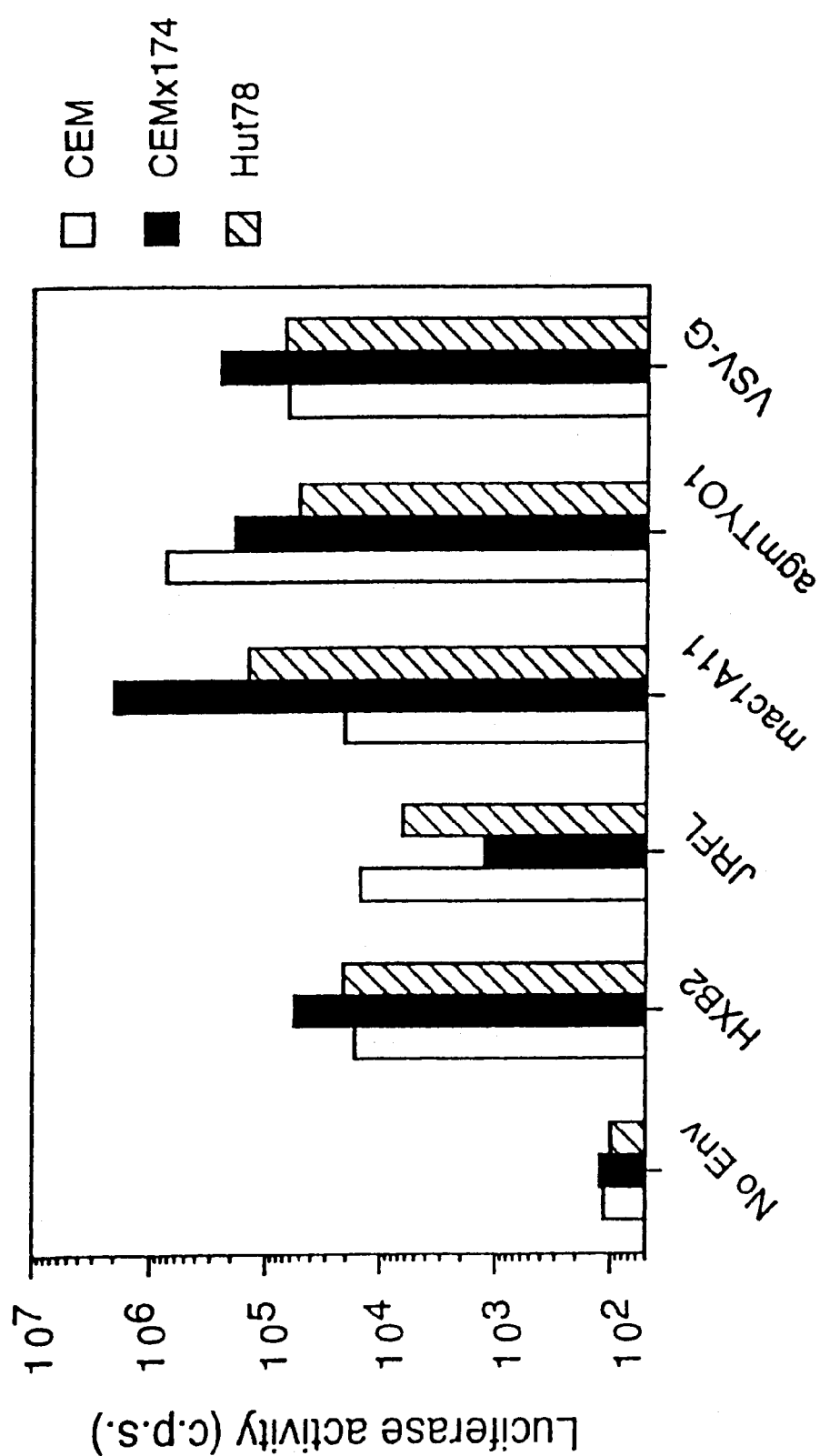

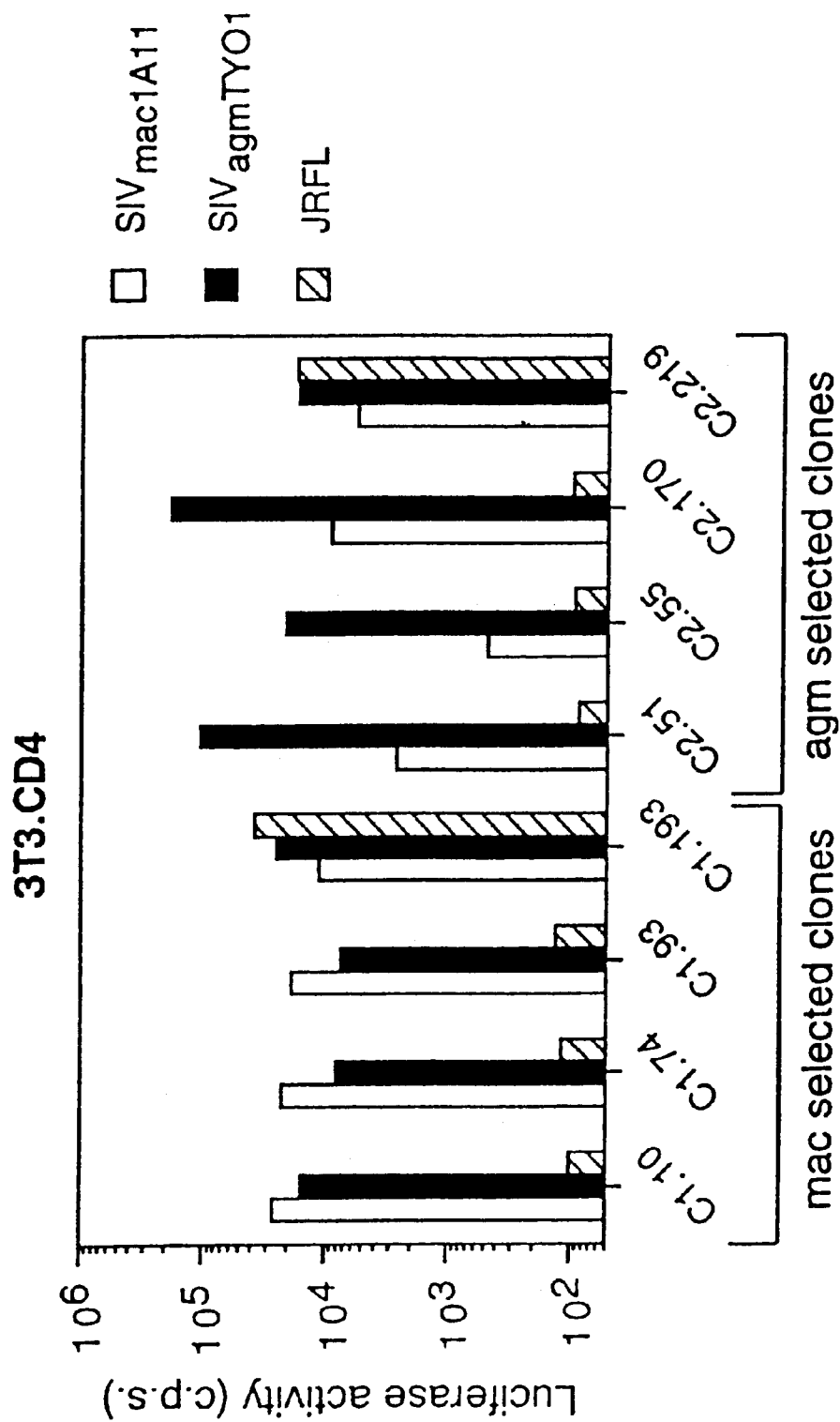

FIG.2C

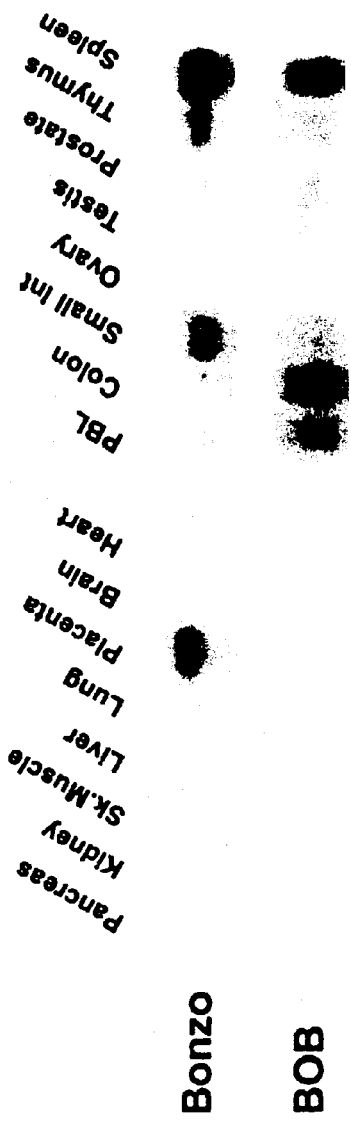
FIG.4A
FIG.4B
FIG.4C

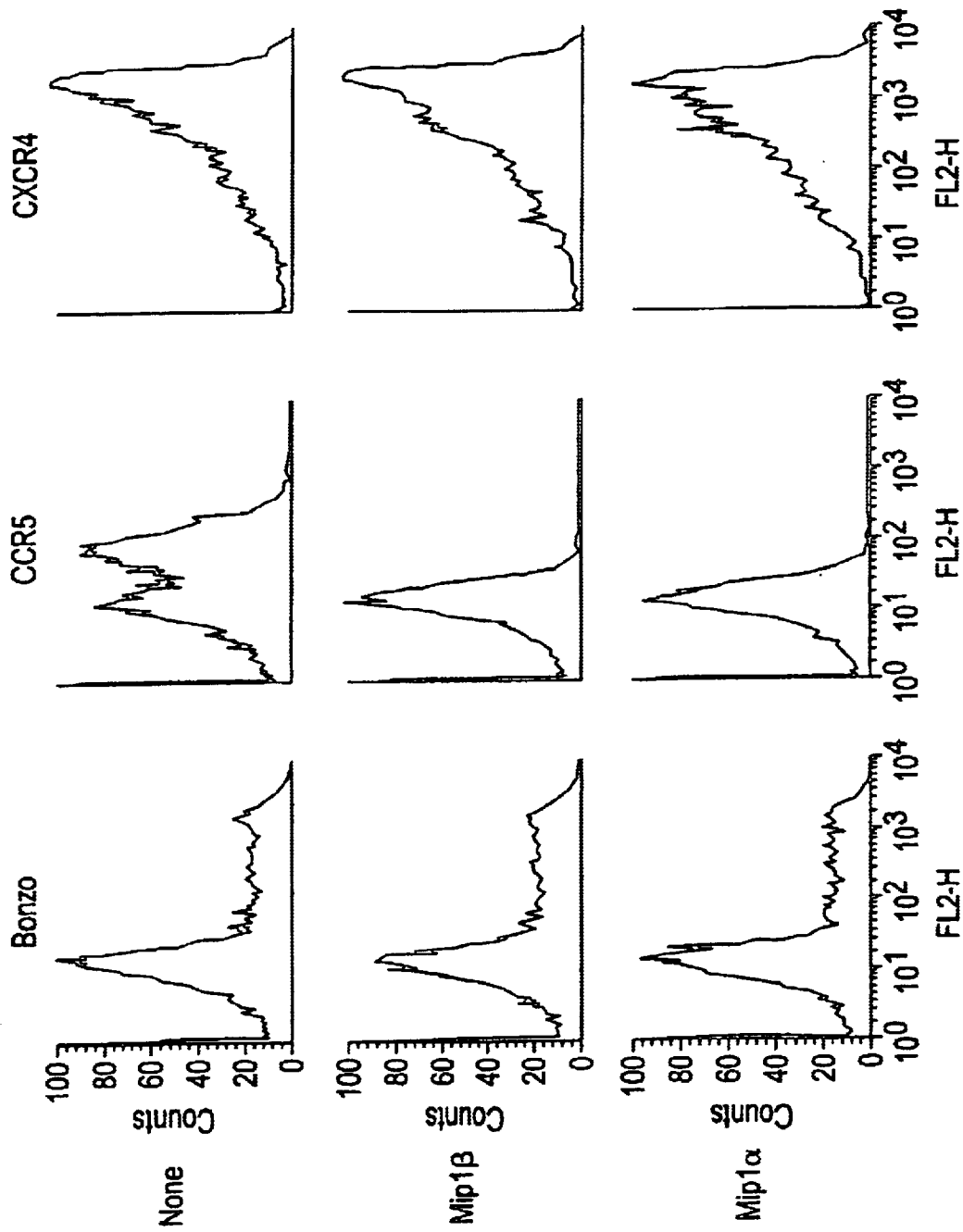

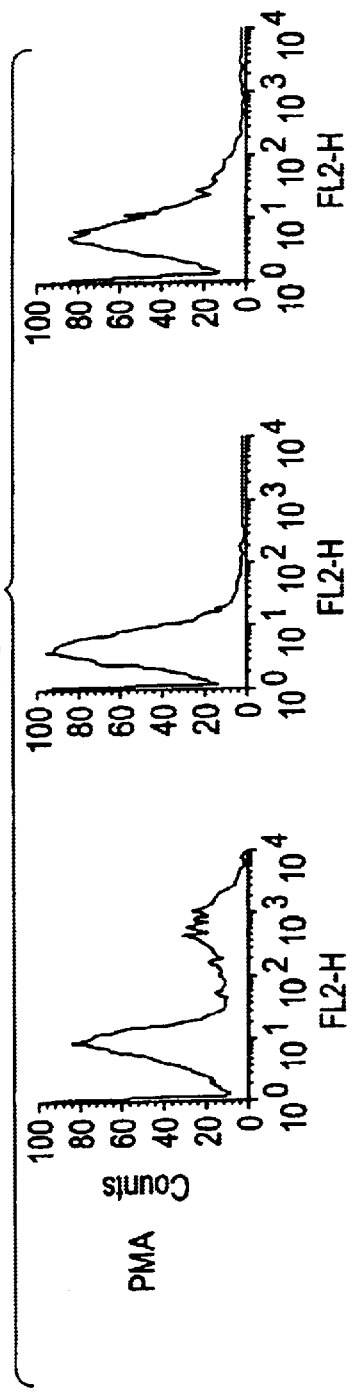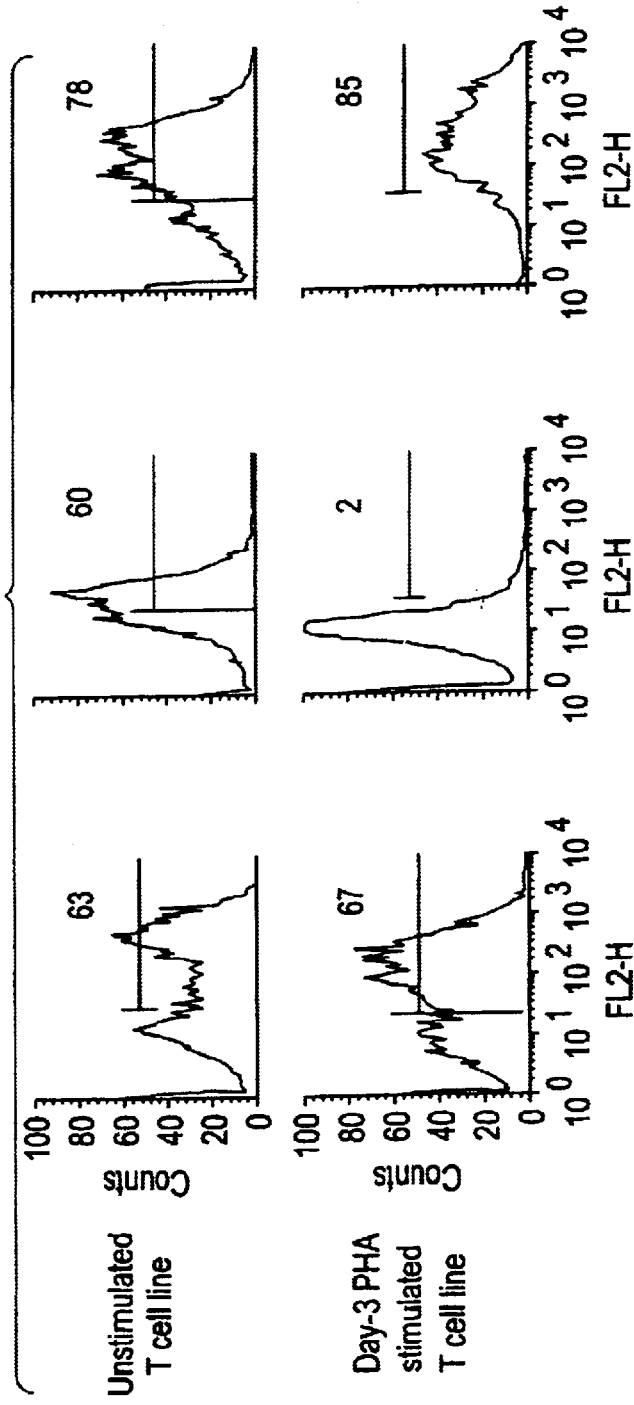

G-COUPLED RECEPTORS ASSOCIATED WITH RETROVIRAL ENTRY INTO CELLS, AND THERAPEUTIC USES THEREOF

CROSS REFERENCE TO RELATED APPLICATIONS

The present Application is a continuation-in-part of copending Ser. No. 09/116,498, filed Jul. 16, 1998, now U.S. Pat. No. 6,251,582, which is a non-provisional application claiming priority to Provisional Patent Application Ser. No. 60/052,827 filed Jul. 17, 1997, the disclosures of which are hereby incorporated by reference in their entireties. Applicants claim the benefits of these applications under 35 U.S.C. §§119 (e) and 120.

GOVERNMENT SUPPORT

The research leading to the present inventions was funded in part by Grant No. RO1 AI 33303 from the National Institutes of Health. The government may have certain rights in the invention.

TECHNICAL FIELD OF THE INVENTION

The present invention relates generally to the infection of target cells by HIV-1, HIV-2 and SIV and more particularly to agents identified herein that mediate the entry of retroviruses into such target cells, and to the diagnostic and therapeutic uses to which such agents may be put. Furthermore, the present invention relates to methods of identifying agents that can modulate the expression and/or function of Bonzo/STRL33. Such agents can be used to either treat inflamation, or alternatively, to enhance the immune response.

BACKGROUND OF THE INVENTION

The human immunodeficiency viruses infect $CD4^+$ macrophages and T helper cells. Although HIV-1 entry requires cell surface expression of CD4, to which the viral envelope glycoproteins bind, several studies have suggested that it is not sufficient for fusion of the viral envelope to the cellular plasma membrane. Early studies have shown that while human cells expressing a transfected CD4 gene were permissive for virus entry, murine cells expressing human CD4 were not. These findings led to the suggestion that there is a species-specific cell surface cofactor required in addition to CD4 for HIV-1 entry. Subsequent studies have shown that strains of HIV-1 that had been adapted for growth in transformed T-cell lines (T-tropic strains) could not infect primary monocytes or macrophages; in contrast, primary viral strains were found to infect monocytes and macrophages, but not transformed T cell lines. This difference in tropism was found to be a consequence of specific sequence differences in the gp120 subunit of the envelope glycoprotein, suggesting that multiple cell type-specific cofactors may be required for entry in addition to CD4.

The nature of the cofactors required for HIV entry proved elusive until it was recently discovered that the principal receptor for entry of macrophage-tropic (M-tropic) HIV-1 strains was CCR5, whereas the principal receptor for entry of T-cell line-tropic (T-tropic) strains was CXCR4. On the other hand, both M-tropic and T-tropic strains of simian immunodeficiency virus (SIV) can be mediated by CCR5, but not CXCR4 [Chew et al., *J. Virol,* 71:2705–2714 (1997); Marcon et al., *J. Virol,* 71:2522–2527 (1997); and Edinger et al., *Proc. Natl. Acad. Sci. USA,* 94:4005–4010 (1997)]. More importantly, SIV strains were also found to infect $CD4^+$ cells that lack CCR5 [Chen et al., 1997, supra; and Edinger et al., 1997, supra].

In humans, CCR5-tropic viruses are primarily involved in transmission, while viruses with broader tropism, particularly for CXCR4, emerge during progression to immunodeficiency [Fauci, *Nature,* 384:529–534 (1996)]. It is not yet known whether appearance of CXCR4-tropic viruses is a consequence or the cause of immune system decline. Insight into this key problem of virus evolution is likely to require experimental manipulation in animal models. Infection of non-human primates with SIV is currently the only good animal model for studying pathogenesis of the immunodeficiency viruses [Desrosiers, *Annu Rev Immunol,* 8:557–578 (1990)]. Moreover, different species of non-human primates vary widely in their responses to SIV infection. For example, Rhesus macaques succumb to immunodeficiency that closely resembles AIDS in humans, but sooty mangabeys and African green monkeys can sustain infection with little evidence of immune system damage [Kestler, *Science,* 248:1109–1112 (1990)]. These interspecies differences provide important clues for understanding and combating disease progression in HIV-infected humans.

Therefore, there is a need to identify and structurally characterize translocation promoting agents other than CCR5 and CXCR4 that function in conjunction with CD4 during SIV and/or HIV infection of human cells as well in the subsequent disease progression. Further, there is a need to determine the specific strains of the retroviruses that can use such translocation promoting agents as alternatives to CXCR4 and CCR5. In addition, there is a need to provide methods of identifying drugs that can interfere with retroviral infection by hindering the interaction of CD4, the various translocation promoting agents and the retroviral envelope glycoproteins.

The citation of any reference herein should not be construed as an admission that such reference is available as "Prior Art" to the instant application.

SUMMARY OF THE INVENTION

The present invention provides an expression cloning strategy to identify SIV receptors which may play a role in human acquired immunodeficiency disease. Two particular nucleic acids encoding two members of the 7-transmembrane G-protein coupled receptor family were identified and isolated by the methods described herein. These SIV receptors were also found to be used by particular strains of HIV-2 and M-tropic HIV-1.

One aspect of the present invention provides an isolated nucleic acid encoding a translocation promoting agent that is substantially homologous to SEQ ID NO:1. In a preferred embodiment of this type the nucleic acid is obtained from a primate. In one such embodiment the nucleic acid encodes a translocation promoting agent that is substantially homologous to SEQ ID NO:3. In another such embodiment the isolated nucleic acid encodes a translocation promoting agent that is substantially homologous to SEQ ID NO:5. In the most preferred embodiment the isolated nucleic acid encodes a translocation promoting agent isolated from a human source.

The present invention also includes nucleic acid primers and/or probes for all of the nucleic acids of the present invention. In addition, the nucleic acids of the present invention may be RNA, or single or doubled stranded DNA, including recombinant DNA.

The present invention also includes an isolated nucleic acid which encodes a translocation promoting agent having the amino acid sequence of SEQ ID NO:2 having one or more conservative substitutions. In a related embodiment the isolated nucleic acid encodes a translocating promoting agent having the amino acid sequence of SEQ ID NO:2. In a preferred embodiment of this type the isolated nucleic acid has a nucleic acid sequence of SEQ ID NO:1.

The present invention also includes an isolated nucleic acid encoding a translocation promoting agent having the amino acid sequence of SEQ ID NO:4 having one or more conservative substitutions. In a related embodiment the isolated nucleic acid encodes a translocation promoting agent having the amino acid sequence of SEQ ID NO:4. In a preferred embodiment of this type the isolated nucleic acid has the nucleic acid sequence of SEQ ID NO:3.

The present invention also includes an isolated nucleic acid encoding a translocation promoting agent having the amino acid sequence of SEQ ID NO:6 having one or more conservative substitutions. In a related embodiment the isolated nucleic acid encodes a translocating promoting agent having the amino acid sequence of SEQ ID NO:6. In a preferred embodiment of this type the isolated nucleic acid has the nucleic acid sequence of SEQ ID NO:5.

The present invention also includes an isolated nucleic acid encoding a translocation promoting agent having the amino acid sequence of SEQ ID NO:10 having one or more conservative substitutions. In a related embodiment the isolated nucleic acid encodes a translocating promoting agent having the amino acid sequence of SEQ ID NO:10. In a preferred embodiment of this type the isolated nucleic acid has the nucleic acid sequence of SEQ ID NO:9.

The present invention also includes an isolated nucleic acid encoding a translocation promoting agent having the amino acid sequence of SEQ ID NO:12 having one or more conservative substitutions. In a related embodiment the isolated nucleic acid encodes a translocating promoting agent having the amino acid sequence of SEQ ID NO:12. In a preferred embodiment of this type the isolated nucleic acid has the nucleic acid sequence of SEQ ID NO:11.

The present invention also includes nucleic acids which contain 18 or more nucleotides that hybridize to a nucleic acid having the nucleotide sequence of SEQ ID NO:1 under standard conditions.

The present invention also includes nucleic acids which contain 18 or more nucleotides that hybridize to a nucleic acid having the nucleotide sequence of SEQ ID NO:3 under standard conditions.

The present invention also includes nucleic acids which contain 18 or more nucleotides that hybridize to a nucleic acid having the nucleotide sequence of SEQ ID NO:5 under standard conditions.

The present invention also includes nucleic acids which contain 18 or more nucleotides that hybridize to a nucleic acid having the nucleotide sequence of SEQ ID NO:9 under standard conditions.

The present invention also includes nucleic acids which contain 18 or more nucleotides that hybridize to a nucleic acid having the nucleotide sequence of SEQ ID NO:11 under standard conditions.

The present invention also provides nucleic acids encoding fusion proteins containing the translocation promoting agents of the present invention and a peptide tag or protein. Such fusion proteins can include, for example Bonzo fused with green fluorescent protein, or Bonzo fused with glutathione-s-transferase.

Also included in the present invention are DNA constructs comprising the isolated nucleic acids of the present invention, that are operatively linked to an expression control sequence. In a preferred embodiment of this type the nucleic acid has the nucleotide sequence of SEQ ID NO:1.

The present invention also includes methods of using the DNA constructs of the present invention to express the translocation promoting agent which they encode. One such embodiment comprises introducing the construct into a host cell and expressing the translocation promoting agent in that host cell. In a preferred embodiment of this type the method includes purifying the translocation promoting agent that was expressed.

The present invention also includes unicellular host cells transformed with the DNA constructs of the present invention. In one preferred embodiment of this type the unicellular host is a primate cell. In a more preferred embodiment the unicellular host is a human cell.

Another aspect of the present invention provides an isolated translocation promoting agent having the amino acid sequence that is substantially homologous to SEQ ID NO:2. In one such embodiment the translocation promoting agent has the amino acid sequence of SEQ ID NO:2 having one or more conservative substitutions. In a preferred embodiment the translocation promoting agent has the amino acid sequence of SEQ ID NO:2.

Another aspect of the present invention provides an isolated translocation promoting agent having the amino acid sequence that is substantially homologous to SEQ ID NO:4. In one such embodiment the translocation promoting agent has the amino acid sequence of SEQ ID NO:4 having one or more conservative substitutions. In a preferred embodiment the translocation promoting agent has the amino acid sequence of SEQ ID NO:4.

Another aspect of the present invention provides an isolated translocation promoting agent having the amino acid sequence that is substantially homologous to SEQ ID NO:6. In one such embodiment the translocation promoting agent has the amino acid sequence of SEQ ID NO:6 having one or more conservative substitutions. In a preferred embodiment the translocation promoting agent has the amino acid sequence of SEQ ID NO:6.

Another aspect of the present invention provides an isolated translocation promoting agent having the amino acid sequence that is substantially homologous to SEQ ID NO:10. In one such embodiment the translocation promoting agent has the amino acid sequence of SEQ ID NO:10 having one or more conservative substitutions. In a preferred embodiment the translocation promoting agent has the amino acid sequence of SEQ ID NO:10.

Another aspect of the present invention provides an isolated translocation promoting agent having the amino acid sequence that is substantially homologous to SEQ ID NO:12. In one such embodiment the translocation promoting agent has the amino acid sequence of SEQ ID NO:12 having one or more conservative substitutions. In a preferred embodiment the translocation promoting agent has the amino acid sequence of SEQ ID NO:12.

Peptide fragments of all the translocation promoting agents of the present invention are also part of the present invention. Such fragments can be generated by treatment with proteolytic enzymes and the like.

The present invention also provides antibodies to the translocation promoting agents of the present invention. In one embodiment of this type the antibody is to the translocation promoting agent having the amino acid sequence of SEQ ID NO:2 having one or more conservative substitutions. In a preferred embodiment of this type the antibody is to the translocation promoting agent having the amino acid sequence of SEQ ID NO:2. In another embodiment of this type the antibody is to the translocation promoting agent having the amino acid sequence of SEQ ID NO:4 having one or more conservative substitutions. In a preferred embodiment of this type the antibody is to the translocation promoting agent having the amino acid sequence of SEQ ID NO:4. In an alternative embodiment of this type the antibody is to the translocation promoting agent having the amino acid sequence of SEQ ID NO:6 having one or more conservative substitutions. In a preferred embodiment of this type the antibody is to the translocation promoting agent having the amino acid sequence of SEQ ID NO:6. In yet another embodiment of this type the antibody is to the translocation promoting agent having the amino acid sequence of SEQ ID NO:10 having one or more conservative substitutions. In a preferred embodiment of this type the antibody is to the translocation promoting agent having the amino acid sequence of SEQ ID NO:10. In still another embodiment of this type the antibody is to the translocation promoting agent having the amino acid sequence of SEQ ID NO:12 having one or more conservative substitutions. In a preferred embodiment of this type the antibody is to the translocation promoting agent having the amino acid sequence of SEQ ID NO:12.

In a preferred embodiment the antibody is a monoclonal antibody and/or a chimeric antibody. The present invention also includes an immortal cell line that produces a monoclonal antibody of the present invention.

The present invention also provides a mammalian cell that expresses human CD4 and is transfected with a vector encoding Bonzo. In one such embodiment Bonzo is a human Bonzo. In a preferred embodiment the human Bonzo has an amino acid sequence of SEQ ID NO:2.

In another embodiment a mammalian cell which expresses CD4, but expresses low levels or no CXCR4 and CCR5, in the absence of transduction with a vector encoding CXCR4 and/or CCR5, is transfected with a vector encoding human Bonzo. In an alternative embodiment, the mammalian cell further comprises a vector encoding one or more translocation promoting agents such as CCR5, CXCR4, CCR2b, CCR3, and BOB.

A related aspect of the invention is a mammalian cell that is transfected with a vector encoding human CD4 and a vector encoding human or primate BOB. In one embodiment the primate BOB has the amino acid sequence of SEQ ID NO:10 or 12. In another embodiment the human BOB has the amino acid sequence of SEQ ID NO:8.

In another embodiment a mammalian cell which expresses CD4, but expresses low levels or no CXCR4 and CCR5, in the absence of transduction with a vector encoding CXCR4 and/or CCR5, is transfected with a vector encoding human BOB. In an alternative embodiment, the mammalian cell further comprises a vector encoding one or more translocation promoting agents such as CCR5, CXCR4, CCR2b, CCR3, and Bonzo.

The present invention also includes the mammalian cells of the present invention attached to solid support matrices. In preferred embodiments of these type the mammalian cell is a human cell.

Another aspect of the present invention is a transgenic non-human mammal comprising a DNA construct containing a human CD4 gene and DNA construct containing a human translocation promoting agent such as BOB or Bonzo. In a preferred embodiment the transgenic non-human mammal further comprises one or more DNA constructs which contain an alternative human translocation promoting agent such as CCR5, CXCR4, CCR2b, and/or CCR3. In a preferred embodiment the transgenic non-human mammal is a mouse.

The present invention further provides a method of identifying a nucleic acid that encodes a human translocation promoting agent which in conjunction with CD4 serves as a receptor for the entry into a cell of a virus having a specific viral envelope glycoprotein. One such method includes transfecting a mammalian cell with a viral vector containing a human cDNA with a flanking-viral insert. Preferably the mammalian cell expresses human CD4 and a known human translocation promoting agent, such as CCR5, but does not express the human translocation promoting agent encoded by the human cDNA which is obtained from a human cDNA library. Next the mammalian cell is transfected with a first selectable viral vector pseudotyped with the specific viral envelope glycoprotein. In this case the first selectable viral vector encodes a first selectable marker. The mammalian cell is then identified by expressing the first selectable marker. The identified mammalian cell is next transfected with a second selectable viral vector that is pseudotyped with a paticular viral envelope glycoprotein. The second selectable viral vector encodes a second selectable marker, and the known human translocation promoting agent can serve in conjunction with CD4 as a receptor for entry of a virus having the particular envelope glycoprotein. An identified mammalian cell is then selected which does not express the second selectable marker. DNA is then extracted from the selected mammalian cell and amplified by PCR using primers for the flanking insert from the viral vectors. In this way a nucleic acid encoding a human translocation promoting agent that can serve in conjunction with CD4 as a receptor for entry of virus having the specific viral envelope glycoprotein is identified.

In one such embodiment the first selectable viral vector is a selectable replication-defective virus. In a preferred embodiment of this type the first selectable viral vector is an HIV-pseudotyped vector. In another embodiment of this type the second selectable viral vector is a selectable replication-defective virus. In a preferred embodiment of this type the second selectable viral vector is an HIV-pseudotyped vector. In a more preferred embodiment both the first selectable viral vector and the second selectable viral vector are HIV-pseudotyped vectors.

In another embodiment of this type the viral vector containing the human cDNA is obtained from the supernatant of BOSC23 packaging cells after subcloning the human cDNA library in the retrovirus pMX and transfecting the human cDNA library into the BOSC23 packaging cells. In another embodiment the mammalian cell is 3T3.CD4. In yet another embodiment the first selectable marker confers antibiotic resistance to the cell. In a preferred embodiment of this type the antibiotic is puromycin and the identification of the mammalian cell expressing the first selectable marker is performed by administering puromycin to the cells and identifying cells that are puromycin resistant. In another embodiment the first selectable marker is green fluorescent protein. In a related embodiment the second selectable marker is green fluorescent protein. In another embodiment of this type the first selectable marker is luciferase. In still another embodiment of this type the second selectable marker is luciferase.

The known translocation promoting agent used in these methods can be any translocating promoting agent known including CCR5, CXCR4, CCR2b, CCR3, Bonzo, and BOB. In a preferred embodiment the known translocation promoting agent is CCR5 and the particular viral envelope glycoprotein is JRFL.

The present invention also includes assays for selecting for a suspected therapeutic agent for possible use in the treatment of AIDS with the use of one of the cells of the present invention. In one particular embodiment the cell is a mammalian cell that expresses human CD4 and is transfected with a vector encoding human Bonzo. In another particular embodiment the mammalian cell is transfected with a vector encoding human CD4 and a vector encoding a human translocation promoting agent such as Bonzo or BOB. In preferred embodiments of this type Bonzo and BOB are human Bonzo and human BOB.

One such method for selecting a suspected therapeutic agent for possible use in the treatment of AIDS comprises administering a potential therapeutic agent to the cell. The cell is next infected with a virus pseudotyped with an HIV envelope glycoprotein.

This is followed by measuring the ability of the cell to resist the infection. Finally the potential therapeutic agent is selected when the measured ability of the cell to resist the infection is statistically greater in the presence of the potential therapeutic agent than in the absence of the potential therapeutic agent. In this case the selected potential therapeutic agent is a suspected therapeutic agent. In a preferred embodiment of this type the virus contains a marker protein and measuring the ability of the cell to resist the infection is performed by detecting the amount of marker protein expressed in the cell. In this case the measured ability of the cell to resist the infection is inversely proportional to the amount of marker protein detected. In a more preferred embodiment of this type the marker protein is either luciferase or green fluorescent protein.

The present invention also includes an assay for selecting a plausible therapeutic agent for possible use in the treatment of AIDS with the use of a transgenic non-human mammal that comprises a DNA construct containing a human CD4 gene and a DNA construct containing either human Bonzo or human BOB. One such method comprises administering a suspected therapeutic agent to the transgenic non-human mammal. Then the transgenic non-human mammal is infected with a virus pseudotyped with an HIV envelope glycoprotein. The ability of the transgenic non-human mammal to resist infection is then measured. The suspected therapeutic agent is selected when the measured ability of the transgenic non-human mammal to resist the infection is statistically greater in the presence of the suspected therapeutic agent than in the absence of the therapeutic agent. In this case the selected therapeutic agent is a plausible therapeutic agent.

The present invention also includes a method of filtering a biological fluid to remove and/or isolate a virus expressing an HIV envelope glycoprotein that binds with CD4 and Bonzo and/or BOB wherein the biological fluid is passed through a mammalian cell which expresses human CD4 and human Bonzo and/or human BOB and is attached to a solid support matrix. In one such embodiment, the mammalian cell is transfected with a vector encoding human CD4 and a vector encoding human Bonzo and/or a vector encoding human BOB.

In yet another aspect of the present invention a method is provided for identifying a ligand for human Bonzo. In one such assay a potential ligand is contacted with a mammalian cell that expresses human Bonzo and CD4, but the mammalian cell does not express CCR5, CXCR4, CCR2b, CCR3, and BOB. Next the mammalian cell is transfected with a selectable replication defective virus (such as HIV) pseudotyped with a specific viral envelope glycoprotein. In this case Bonzo in conjunction with CD4 serves as a receptor for entry into a cell of a virus having the specific viral envelope glycoprotein. Finally the marker protein is detected and a ligand is selected when the amount of marker protein detected is less than that detected when the transfection of the mammalian cells with the selectable replication-defective virus is performed without the prior contacting of a potential ligand with the mammalian cell. In a preferred embodiment of this type the marker protein is either luciferase or green fluorescent protein. In another preferred embodiment the method includes contacting the selected ligand with purified human Bonzo and then detecting the binding of that ligand to the purified human Bonzo. In this case a ligand is identified by its binding to the purified human Bonzo. In a more preferred embodiment, the ligand binds to the purified human Bonzo under standard physiological conditions (e.g. 100 mM NaCl pH7.4, at 37° C.) and has a KD of less than $10^{-6}$ Molar.

In yet another aspect of the present invention a method is provided for identifying a ligand for human BOB. In one such assay a potential ligand is contacted with a mammalian cell that expresses human BOB and CD4, but the mammalian cell does not express CCR5, CXCR4, CCR2b, CCR3, and Bonzo. Next the mammalian cell is transfected with a selectable replication defective virus (such as HIV) pseudotyped with a specific viral envelope glycoprotein. In this case BOB in conjunction with CD4 serves as a receptor for entry into a cell of a virus having the specific viral envelope glycoprotein. Finally the marker protein is detected and a ligand is selected when the amount of marker protein detected is less than that detected when the transfection of the mammalian cells with the selectable replication-defective virus is performed without the prior contacting of a potential ligand with the mammalian cell. In a preferred embodiment of this type the marker protein is either luciferase or green fluorescent protein. In another preferred embodiment the method includes contacting the selected ligand which was selected with purified human BOB and then detecting the binding of that ligand to the purified human BOB. In this case a ligand is identified by binding to the purified human BOB. In a more preferred embodiment, the ligand binds to the purified human BOB under standard physiological conditions (e.g. 100 mM NaCl pH7.4, at 37° C.) and has a KD of less than $10^{-6}$ Molar.

The present invention further provides methods of identifying agents that can modulate the expression and/or function of Bonzo/STRL33. In one such method, the agent can be selected for enhancing the immune response to a specific pathogen and/or can be selected for enhancing the immune response against a specific vaccine. One embodiment comprises contacting an agent with a cell that encodes Bonzo/STRL33 and then determining (e.g., measuring) the amount of Bonzo/STRL33 expressed by a cell in the presence of the agent. An agent is identified as an agent that can enhance the immune response to a specific pathogen and/or against a specific vaccine when the amount of expression of Bonzo/STRL33 increases in the presence of the agent relative to in the absence of the agent. In one particular embodiment, determining the amount of Bonzo/STRL33 expressed by the cell is performed with an antibody raised against Bonzo/STRL33. In another embodiment determining the amount of Bonzo/STRL33 expressed by the cell is performed by PCR.

In another method, an agent can be selected for enhancing the immune response to a specific pathogen and/or can be selected for enhancing the immune response against a specific vaccine by contacting an agent with a cell that normally encodes Bonzo/STRL33, but in which the coding sequence for Bonzo/STRL33 has been replaced by a coding sequence for a reporter gene. The amount of the reporter gene expressed by the cell in the presence of the agent is then determined (e.g., measured). An agent is identified as an agent that can enhance the immune response to a specific pathogen and/or against a specific vaccine when the amount of the reporter gene expressed by the cell increases in the presence of the agent relative to in the absence of the agent. In a particular embodiment the coding sequence for the reporter gene encodes green fluorescent protein. In another embodiment, the coding sequence for the reporter gene encodes luciferase.

The present invention also provides the agents obtained by such methods. Preferably, the agent is a small organic molecule. The present invention further provides methods of enhancing the immune response for a specific pathogen or to enhance the effect of a specific vaccine that comprises administering an agent identified by a method of the present invention to an animal subject. Preferably the animal subject is a human.

The present invention also provides methods of identifying agents that can inhibit the recruitment of memory cells. One such embodiment comprises contacting an agent with a cell that encodes Bonzo/STRL33 and then determining (e.g., measuring) the amount of Bonzo/STRL33 expressed by a cell in the presence of the agent. An agent is identified as an agent that can inhibit the recruitment of memory cells when the amount of expression of Bonzo/STRL33 decreases in the presence of the agent relative to in the absence of the agent. In one particular embodiment, determining the amount of Bonzo/STRL33 expressed by the cell is performed with an antibody raised against Bonzo/STRL33. In another embodiment determining the amount of Bonzo/STRL33 expressed by the cell is performed by PCR.

In another method, the agent can be selected for inhibiting the recruitment of memory cells by contacting an agent with a cell that normally encodes Bonzo/STRL33, but in which the coding sequence for Bonzo/STRL33 has been replaced by a coding sequence for a reporter gene. The amount of the reporter gene expressed by the cell in the presence of the agent is then determined (e.g., measured). An agent is identified as an agent that can inhibit the recruitment of memory cells when the amount of expression of Bonzo/STRL33 decreases in the presence of the agent relative to in the absence of the agent. In a particular embodiment the coding sequence for the reporter gene encodes green fluorescent protein. In another embodiment, the coding sequence for the reporter gene encodes luciferase.

The present invention also provides the agents obtained by such methods. Preferably, the agent is a small organic molecule. The present invention further provides methods of treating inflammation comprising administering an agent identified by a method of the present invention to an animal subject in need of such treatment. Preferably the animal subject is a human.

The present invention also provides methods of enhancing the immune response for a specific pathogen and/or to enhance the effect of a specific vaccine that comprises administering to an animal subject an agent that causes an increase in Bonzo/STRL 33 expression and/or function. In a preferred embodiment of this type the animal subject is a human.

The present invention further provides methods of treating inflammation that comprise administering to an animal subject in need of such treatment an agent that causes a decrease in Bonzo/STRL 33 expression and/or function. In a preferred embodiment of this type the animal subject is a human. In a particular embodiment the agent is an antisense nucleic acid to the Bonzo/STRL 33 transcript. In another such embodiment the agent is an antibody to the Bonzo/STRL 33 protein. In still another embodiment the agent is a particular compound that blocks the function of Bonzo/STRL 33 protein. In a particular embodiment of this type the agent is a small organic compound that binds to the Bonzo/STRL 33 protein and thereby inhibits its function.

These and other aspects of the present invention will be better appreciated by reference to the following drawings and Detailed Description.

BRIEF DESCRIPTION OF THE DRAWINGS

FIGS. 1a–1b show the specificity of SIV Envs for chemokine receptors on target cells. FIG. 1a depicts the results of the infection of 3T3.CD4 cells stably expressing CCR1, CCR5, or CXCR4 with luciferase reporter viruses pseudotyped with Envs of HIV-1 (HXB2 and JRFL), SIV (mac1A11 and agmTY01) or VSV-G. FIG. 1b depicts the infection of U87 cells and U87.CD4 cells with the pseudotyped reporter viruses. FIG. 1c depicts the results of the infection of transformed CD4$^+$ cell lines with the pseudotyped reporter viruses. Lysates were assayed 3 days post-infection for luciferase activity as described in Methods (Example 1).

FIGS. 2a–2c show the expression cloning of novel SIV receptors. FIG. 2a shows an outline of the expression cloning strategy used to isolate SIV receptors. FIG. 2b depicts the results of the infection of representative 3T3.CD4 clones, previously selected with HIV-puro(SIV) pseudotyped virus, with HIV-luc pseudotyped with SIV and M-tropic HIV-1 Envs. FIG. 2c shows the amino acid sequence alignment of the receptors encoded by the BOB and Bonzo cDNAs with HIV receptors CXCR4 and CCR5. Identical amino acids are shaded and the putative extracellular domains (based on CCR5 alignment) are boxed. The "DRY box" sequence, which is involved in signaling and is characteristic of chemokine receptors, is highlighted in bold. Bonzo contains a divergent "DRY box" motif compared to other HIV receptors; this sequence has thus been observed in only one other chemokine receptor, EBI 2.

FIG. 3a depicts the results of the infection of 293T cells transiently cotransfected with plasmids encoding CD4 plus CCR1, Bonzo, BOB, or CCR5. The cells were infected 2 days later with luciferase reporter viruses (e.g. HIV-luc) pseudotyped with different SIV or HIV-2 Envs. The HIV-2 Envs, UC1, FO784, ST/SXB1 and 7312a have been shown to use CCR5; ST/24.1 and ROD can use both CCR5 and CXCR4; UC2 is known to use only CXCR4. FIG. 3b depicts the results of the infection of the transiently transfected 293T cells with HIV-luc pseudotyped with HIV-1 Envs or control VSV-G. Target cells expressing CXCR4 were also included to identify T-tropic Envs, even though 293T cells express endogenous CXCR4. FIG. 3c depicts the results of 3T3.CD4 cells stably expressing CCR1, BOB, Bonzo, CCR5 or CXCR4 which were infected with the luciferase reporter viruses as described above. Luciferase activity was measured on day 3. Similar results were obtained in three independent experiments.

FIGS. 4a–4c shows the expression of BOB and Bonzo mRNAs in human lymphoid tissues and cell lines. FIG. 4a shows an RNA tissue blot of various human tissues (Clontech) probed with full length BOB and Bonzo cDNAs as described in Methods (Example 1). The signals correspond to 2.1 kb Bonzo and 2.2 Kb BOB transcripts. FIG. 4b depicts the RT-PCR analysis of BOB and Bonzo transcripts in human PBMC, resting or stimulated with PHA (Sigma) for 7 days, and purified lymphocyte subsets. Total RNAs isolated from these cells were amplified with primers specific for BOB, Bonzo or glyceraldehyde-3-phosphate dehydrogenase (GAPDH) as a control, shown in the bottom panel. Primer specificity has been verified on 3T3 cells expressing BOB or Bonzo. FIG. 4c shows the Northern blot analysis of poly(A)$^+$ mRNA from different cell types. Each lane was loaded with 5 μg poly(A)$^+$ mRNA except for PBMC, for which 10 μg of total RNA was used.

In FIG. 5a HOS cells stably expressing Bonzo were generated by retroviral transduction of the Bonzo or CCR5 cDNA using the pBabe vector [Deng et al., Nature 388:296 (1997)]. Cells were stained with the anti-Bonzo mAb followed by a PE-conjugated goat-anti-mouse antibody. In FIG. 5b 293T cells were transfected with a pcDNA3 plasmid encoding either GFP or Bonzo-GFP fusion protein. Cells were then stained, 48 h post-transfection, with Bonzo antibody as in Example 2 below.

FIGS. 6b and 6c are CD4$^+$ and CD8$^+$ T cell subsets. FIG. 6d are memory (CD4RO+) and naive (CD45RO−) T cells (gated for CD3$^+$ cells). FIG. 6e are NK cells (CD 16+). FIG. 6g are B cells (CD19+). FIG. 6f are γδ T cells (gated on CD3$^+$ cells). FIG. 6h shows the monocyte expression (CD14+). FIG. 6i are the Dendritic cells: Cells were first stained with anti-Bonzo antibody as described in Example 2 below, and then with FITC-conjugated anti-CD3, CD14 and CD19 and TC-conjugated anti-HLA-DR antibodies. A gate was set to exclude FITC positive cells (T cells, B cells and monocytes). The remaining HLA-DR$^+$ cells identify DC.

FIG. 7a shows CCR5 expression on T cell subsets and comparative staining of Bonzo (bottom panel). FIG. 7b shows Bonzo expression of T cell subsets from a CCR5-null individual.

FIGS. 11a–11c show the effects of chemokines, PMA and mitogen stimulation on Bonzo, CCR5 and CXCR4 cell surface expression. To maximize expression levels, CD4$^+$ cells cultured with IL-15 for 12 days were used in the Bonzo and CCR5 downregulation experiments, and IL-4 cultured cells were used for examining CXCR4 downregulation. FIG. 11a show cells that were cultured for 24 hours in the presence of the chemokines RANTES, MIP-1α, MIP-1β or SDF-1 α at 1 μg/ml each, before staining. FIG. 11b shows cells that were stimulated with 15 ng/ml PMA for 12 hours and stained for chemokine receptor expression. FIG. 11c shows cells that were activated CD4$^+$ human T cell lines maintained in IL-2 and were stained for chemokine receptor expression 2 weeks post stimulation (upper panel) or three days after re-stimulation through TCR (lower panel).

In FIG. 12a, from the top, the wild-type Bonzo genomic structure, the targeting construct, and the targeted Bonzo/EGFP knock-in structure, respectively. The arrows above each gene depict the directions of transcription. The open triangles are loxP sites. H, HindIII; A, ApaI; RV, EcoRI; C, ClaI. FIG. 12b is the Southern blot analysis of progeny of heterozygous intercrossing. The probe used is depicted by the solid bar beneath the targeted structure in FIG. 12a. The wild-type allele yields a 7 kb EcoRV genomic fragment, whereas the targeted allele yields a 6.6 kb fragment. FIG. 12c shows the RT-PCR analysis of expression of Bonzo mRNA in mutant mice. Primers used are described in Materials and Methods. In a TAE gel, a 590 bp DNA fragment is amplified from wide-type (top panel, lane 2) and heterozygous (lane 3) mice, but absent in Bz$^{-/-}$ mice (lane 4). A similar RT-PCR assay was carried out for GADPH mRNA, as a loading control (lower panel).

FIG. 13a shows GFP expression on CD3$^+$ T cells. FIG. 13b are cells stained with anti-mouse CD8-TC and CD44-PE, gated on CD8$^+$ T cells. FIG. 13c is IEL stained with PE conjugated anti-TCRγδ antibody. FIG. 13d is the GFP expression on naïve and memory mouse CD4 T cells. LN cells stained with CD4-TC and with either CD44$^-$PE or CD45RB$^-$PE and analyzed after gating was set on CD4$^+$ cells.

DETAILED DESCRIPTION OF THE INVENTION

Figure 1B:
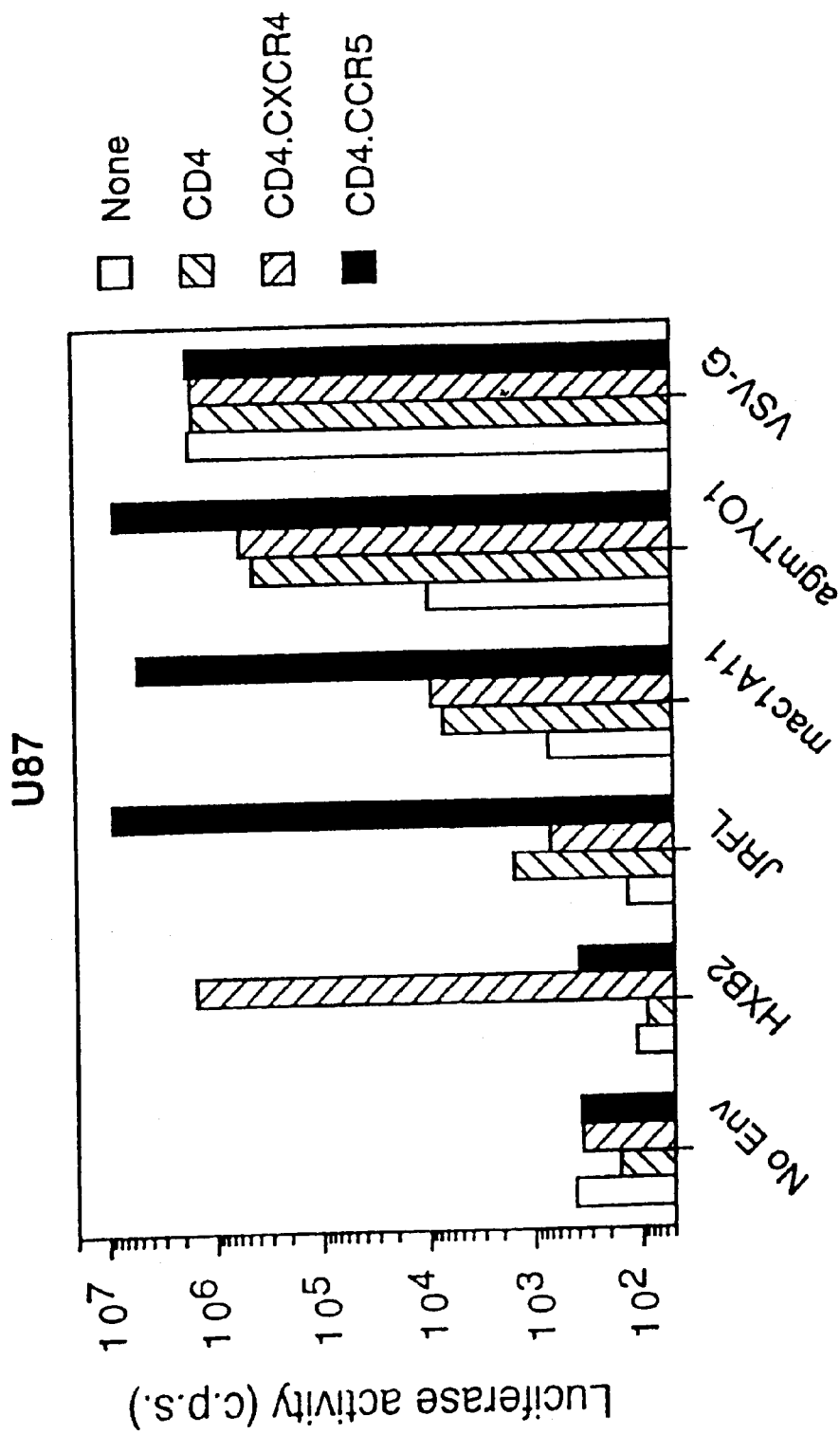

The present invention provides two new HIV/SIV translocation promoting agents, Bonzo and BOB. Such translocation promoting agents act in conjunction with CD4 to serve as a receptor for the entry into a cell of a virus having a specific viral envelope glycoprotein. The use of these new receptors in the experimental infection of nonhuman primates with particular SIV and HIV strains can provide important insights into both the viral transmission and mechanisms of SIV and HIV induced acquired immune deficiency syndrome. Furthermore, the ability of HIVs to infect cells by way of these newly disclosed receptors must now be included in the strategies aimed at blocking CCR5-tropic virus entry.

In addition, the present invention provides a facile method of identifying still other such translocation promoting agents (see Example 1).

One initial objective out of which the present invention grew is to understand the mechanism through which HIV and SIV gain entrance into target cells. It has been known that the virus binds to CD4, but that CD4 is not sufficient for infection. With the new molecules available, it is possible to study the biochemical events involved in initiation of fusion between the viral envelope and the cellular plasma membrane. Another, and, potentially, more important purpose is to develop small animal models for HIV infection, which allow a better understanding of the pathogenesis of AIDS and provide a system for testing potential therapies.

While SIVs do not appear to use CXCR4, they use CCR5, Bonzo, and BOB as receptors. Variations in the structure or expression of these molecules represent host variables that influence the outcome of SIV infection. Therefore it is important to determine the correlation between the ability of primary strains of SIV to use the receptors of the present invention and the susceptibility of the animals to disease progression.

By means of the teachings of the present invention it is possible to screen for/identify the natural ligands for Bonzo and BOB. It is possible to screen for inhibitors of envelope-chemokine receptor interactions. In conjunction with CD4 (membrane-bound or in a soluble form), this latter screen provides a powerful approach for blocking the infectious life cycle prior to viral entry.

The present invention provides animal model systems, developed from the teachings herein, for studying HIV infection and pathogenesis. This allows testing of drugs in an animal system prior to human trials. This discovery allows identification of additional related G-protein coupled receptors that have a role in the broadening of the viral host range in vivo and in pathogenesis in organ systems such as the brain.

This discovery indicates that chemokine receptors encoded by other viruses, particularly members of the Herpes virus family (e.g., CMV, HHV-6, HHV-8), may serve to broaden the host range of HIV in individuals infected with both HIV and such viruses. This can therefore increase the range of tissues infected or provide a ligand for HIV envelope that can result in deleterious signal transduction in various tissues. This information could lead to novel approaches to block the synergy between HIV and viral cofactors.

Furthermore, as shown in Example 2 the expression pattern of Bonzo/STRL33, an orphan SIV/HIV coreceptor, is highly restricted to the memory subset of T cells and is upregulated upon stimulation of these cells with IL-2 or IL-15. Both the pattern and the regulation of Bonzo expression closely paralleled that of CC family chemokine receptors CCR5 or CCR6 and are inversely correlated with CXCR4 expression. However, in striking contrast to CCR5, Bonzo expression was not downmodulated by PMA or mitogen stimulation of T cells. Targeted replacement of the Bonzo gene with a gene encoding green fluorescent protein in mice revealed that the expression and cytokine regulation of mouse Bonzo are comparable to those of its human counterpart. The similar expression and regulation patterns of Bonzo and the HIV coreceptor CCR5 has important implications for understanding the role of HIV/SIV receptors in viral evolution and pathogenesis.

In addition, Bonzo is unique in that its sequence bears a non-canonical "DRY" box motif which is thought to couple chemokine receptors to G-proteins [Unutmaz et. al., *Semin Immunol* 10:225 (1998), Deng et al. *Nature* 388:296 (1997)]. As provided herein, mice in which the Bonzo gene has been replaced with EGFP is of considerable utility for tracking the migration patterns of memory T cell in responses to inflammatory stimuli. The insight into expression pattern and function of Bonzo should also help elucidate its role during SIV/HIV infection.

Indeed, Bonzo is specifically expressed in memory T cells, particularly cytotoxic T cells (but also helper T cells). Hence, the inhibition of Bonzo function blocks the recruitment of memory cells to sites of inflammation, while agonists recruit memory cells and could thus can be used for immune enhancement in response to specific pathogens or vaccines. Heretofore, with the exception of particular cell lines and tissues, it was not known where Bonzo was expressed, or in which kinds of lymphocytes. The results disclosed in Example 2 enables an approach to developing therapeutics targeted to particular leukocyte populations.

Various terms are used in the specification, which are defined as follows:

The term "translocation promoting agent" is used herein interchangeably with the terms "translocating promoter", "translocating promoting agent" and "translocating promoting protein", and refer to receptor proteins found on, or in membranes of $CD4^+$ cells that interact with and/or in conjunction with CD4 in HIV and /or SIV translocation into the cell. Two translocation promoting agents exemplified in the present invention are the proteins named "Bonzo"(also named STRL33 or TYMSTR, or Bonzo/STRL33) and "BOB". In one particular embodiment, Bonzo is a human protein having an amino acid sequence of SEQ ID NO:2. In another embodiment, Bonzo is an African green monkey protein having an amino acid sequence of SEQ ID NO:4. In still another embodiment, Bonzo is a pigtail macaque protein having an amino acid sequence of SEQ ID NO:6. In yet another embodiment, the translocation promoting agent is "BOB", a human protein having an amino acid sequence of SEQ ID NO:8. There are now six "known" members of the chemokine receptor family that have been shown to function in HIV-1 entry (i.e., known human translocation promoting agents) CCR5, CXCR4, CCR2b, CCR3 and with the present disclosure, Bonzo and BOB.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

As used herein a "small organic molecule" is an organic compound [or organic compound complexed with an inorganic compound (e.g., metal)] that has a molecular weight of less than 3 kilodaltons, and preferably less than 1.5 kilodaltons. An "agent" of the present invention is preferably a small organic molecule.

A composition comprising "A"(where "A" is a single protein, DNA molecule, vector, recombinant host cell, etc.)

is substantially free of "B"(where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

In a specific embodiment, the term "about" means within 20%, preferably within 10%, and more preferably within 5%.

Genes Encoding Translocation Promoting Proteins

The present invention contemplates isolation of a gene encoding a translocation promoting agent of the invention, including a full length, or naturally occurring form of translocation promoting agent, and any antigenic fragments thereof from any animal, particularly mammalian and more particularly human source. As used herein, the term "gene" refers to an assembly of nucleotides that encode a polypeptide, and includes cDNA and genomic DNA nucleic acids.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage, virus, or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA. DNA:RNA. DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 18 nucleotides; preferably at least about 36 nucleotides; and more preferably the length is at least about 48 nucleotides. Such nucleic acids can be used as primers or nucleic acid probes for the nucleic acids encoding the translocation promoting agents of the present invention.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" as used herein refers to one method of inserting a foreign DNA sequence of a vector into chromosome. The vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

As used herein a reporter gene is a nucleic acid that is readily detectable and/or encodes a gene product that is readily detectable such as green fluorescent protein (as used in the Examples below and/or as described in U.S. Pat. No. 5,625,048 issued Apr. 29, 1997, and WO 97/26333, published Jul. 24, 1997, the disclosures of each are hereby incorporated by reference herein in their entireties) or luciferase. Reporter genes are standardly employed in drug assays to enhance the sensitivity of the assay and/or to make the assay simpler to perform.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be secreted or expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell 50:667 (1987)].

Accordingly, the term "sequence similarity" in all its grammatical forms refers to the degree of identity or correspondence between nucleic acid or amino acid sequences of proteins that do not share a common evolutionary origin [see, Reeck et al., Cell 50:667 (1987)]. However, in common usage and in the instant application, the term "homologous," when modified with an adverb such as "substantially," may refer to sequence similarity and not a common evolutionary origin.

In a specific embodiment, two DNA sequences are "substantially homologous" or "substantially similar" when at least 50% (preferably at least 75%, and most preferably at least 90 to 95%) of the nucleotides match over the defined length of the DNA coding sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program with the default parameters.

The term "corresponding to" is used herein to refer similar or homologous sequences, more preferably substantially similar or substantially homologous sequences, whether the exact position is identical or different from the molecule to which the similarity or homology is measured. The term "corresponding to" refers to the sequence similarity, and not the numbering of the amino acid residues or nucleotide bases.

A gene encoding a translocation promoting agent, whether genomic DNA or cDNA, can be isolated from any source, particularly from a human cDNA or genomic library. Methods for obtaining a particular translocating promoting agent gene are well known in the art, as described above (see, e.g., Sambrook et al., 1989, supra). The DNA may be obtained by standard procedures known in the art from cloned DNA (e.g., a DNA "library"), and preferably is obtained from a cDNA library prepared from tissues with high level expression of the protein (e.g., a macrophage/monocyte or T lymphocyte cDNA library, since these are the cells that evidence highest levels of expression of translocation promoting proteins), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

Once the DNA fragments are generated, identification of the specific DNA fragment containing the desired translocation promoting agent gene may be accomplished in a number of ways. For example, if an amount of a portion of a translocation promoting agent gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). For example, a set of oligonucleotides corresponding to the partial amino acid sequence information obtained for the translocation promoting agent protein can be prepared and used as probes for DNA encoding the translocation promoting agent, or as primers for cDNA or mRNA (e.g., in combination with a poly-T primer for RT-PCR). Preferably, a fragment is selected that is highly unique to the translocation promoting agent of the invention. Those DNA fragments with substantial homology to the probe will hybridize. As noted above, the greater the degree of homology, the more stringent hybridization conditions can be used. In a specific embodiment, high stringency hybridization conditions are used to identify a homologous translocation promoting agent gene.

Further selection can be carried out on the basis of the properties of the gene, e.g., if the gene encodes a protein product having the isoelectric, electrophoretic, amino acid composition, or partial amino acid sequence of a translocation promoting agent as disclosed herein. Thus, the presence of the gene may be detected by assays based on the physical, chemical, immunological, or functional properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for a translocation promoting agent of the present invention. For example, polyclonal antibody to the human translocation promoting agent, can be used to confirm expression of the translocation promoting agent, (either simian or human).

Receptors that act as translocation promoting agents for particular HIV or SIV strains can be identified using an HIV-luciferase vector (for example) pseudotyped with the corresponding HIV or SIV envelope glycoproteins (ENVS) to infect $CD4^+$ cell lines. The genes encoding such identified translocation promoting agents can then be isolated. For example, a human T cell clone cDNA library can be subcloned into a viral vector, preferably a retroviral vector, e.g., pMX, and then transfected into a packaging cell such as BOSC23. The supernatant from these cells can then be used to transfect the $CD4^+$ cells (e.g., 3T3.CD4 cells). The transduced cells are next challenged with a selectable replication-defective virus, such as HIV-puro, (which bestows puromycin resistance to the transfected cell) pseudotyped with virus bearing ENVS from HIV or SIV strains, for example $SIV_{agmTY01}$ or $SIV_{mac1A11}$. The cells are next treated with puromycin to select for cells infected by the HIV-puro virus (which bestows the puromycin resistance). The puromycin resistant colonies are next transfected with an HIV pseudotyped with an HIV envelope glycoprotein which has a specific requirement for a known translocation promoting agent. (For example, viruses pseudotyped with the HIV envelope glycoprotein JRFL infect cells expressing the chemokine receptor CCR5.) The genomic DNA is next extracted from the puromycin resistant colonies that were also resistant to the infection of the HIV pseudotyped with an HIV envelope glycoprotein which has the specific requirement for a known translocation promoting agent. In the case in which the virus was pseudotyped with JRFL, the cells in these colonies would be lacking CCR5. The extracted DNA is then subjected to PCR amplification using the primer flanking inserts from the viral vectors. Nucleic acids which encode the translocation promoting agents are detected in this manner. The PCR products can then be subcloned into an expression vector and the DNA sequences can then be determined.

The present invention also relates to genes encoding analogs and derivatives of the translocation promoting agent of the invention, that have the same or homologous functional activity as the translocation promoting agent, and homologs thereof from other species. The production and use of derivatives and analogs related to the translocation promoting agent are within the scope of the present invention. In a specific embodiment, the derivative or analog is functionally active, i.e., capable of exhibiting one or more functional activities associated with a full-length, wild-type translocation promoting agent of the invention. In another embodiment, the translocation promoting agent contains a different cytoplasmic domain, e.g., which associates the protein with the cell membrane but cannot mediate G protein activation and/or translocation.

Derivatives of translocation promoting agents can be made by altering nucleic acids encoding translocation promoting agents by substitutions, additions or deletions that provide for functionally modified molecules. Preferably, derivatives are made that have diminished HIV-translocational activity relative to the native translocating promoting agent. Other derivatives may encode soluble fragments of the translocating promoting agent extracellular domain that have the lower affinity for the natural ligand of the translocating promoting agent of the invention but greater affinity for an HIV or SIV envelope protein. Such soluble derivatives may be potent inhibitors of HIV or SIV binding to the translocation promoting agent on cells, e.g., to Bonzo or BOB on macrophages and T cells.

Due to the degeneracy of nucleotide coding sequences, other DNA sequences which encode substantially the same amino acid sequence as a translocation promoting agent gene may be used in the practice of the present invention. These include but are not limited to allelic genes, homologous genes from other species, and nucleotide sequences comprising all or portions of translocation promoting agent genes which are altered by the substitution of different codons that encode the same amino acid residue within the sequence, thus producing a silent change. Likewise, the translocation promoting agent derivatives of the invention include, but are not limited to, those containing, as a primary amino acid sequence, all or part of the amino acid sequence of a translocation promoting agent protein including altered sequences in which functionally equivalent amino acid residues are substituted for residues within the sequence resulting in one or more conservative amino acid substitutions. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. Such substitutions are defined herein as conservative substitutions. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

The genes encoding translocation promoting agent derivatives and analogs of the invention can be produced by various methods known in the art. The manipulations which result in their production can occur at the gene or protein level. For example, the cloned translocation promoting agent gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of a translocation promoting agent, care should be taken to ensure that the modified gene remains within the same translational reading frame as the translocation promoting agent gene, uninterrupted by translational stop signals, in the gene region where the desired activity is encoded.

Additionally, the translocation promoting agent-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations diminish the HIV translocation activity of the mutated translocation promoting agent gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2$\mu$ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of Translocation Promoting Agents

The nucleotide sequence coding for a translocation promoting agent of the present invention, or antigenic fragment, derivative or analog thereof, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a translocation promoting agent of the invention is operationally associated with a promoter in an expression vector of the invention.

Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding a translocation promoting agent and/or its flanking regions.

As pointed out above, potential chimeric partners for a translocation promoting agent include other transmembrane domains, or a domain for modification with a phospholipid anchor.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant translocation promoting agent of the invention, or fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding a translocation promoting agent is cultured in an appropriate cell culture medium under conditions that provide for expression of translocation promoting agent by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a translocation promoting agent may be controlled by any promoter/enhancer element known in the art, but these regulatory elements must be functional in the host selected for expression. In one embodiment the translocation promoting agent is under the control of the CD4 enhancer/promoter/silencer, as described [Killeen et al., (1993) supra]. Promoters which may be used to control the translocation promoting agent gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Omitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, the transmembrane translocation promoting agent expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, translocation promoting activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

A recombinant translocation promoting agent expressed as an integral membrane protein can be isolated and purified by standard methods. Generally, the integral membrane protein can be obtained by lysing the membrane with detergents, such as but not limited to, sodium dodecyl sulfate (SDS), Triton X-100, nonidet P-40 (NP-40), digoxin, sodium deoxycholate, and the like, including mixtures thereof. Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

For the assays of the invention that depend on evaluating the activity of the translocation promoting protein or the expression thereof, the gene encoding the translocation promoting protein or a reporter protein can be transfected or used to transform host cells. In one embodiment, the cells are obtained from knockin animals in which a reporter gene has replaced the coding sequence for the translocation promoting protein (see Example 2).

In a particular embodiment, the host cells are transfected to co-express human CD4, and preferably, such cells lack the ability to express an endogenous or native translocation promoting agent. Co-expression of the translocation promoting agent and CD4 facilitates HIV and/or SIV translocation, which is the endpoint for an assay to identify antagonists of HIV and/or SIV translocation.

Antibodies to Translocation Promoting Protein

According to the invention, the translocation promoting agent produced recombinantly or by chemical synthesis, and fragments or other derivatives or analogs thereof, including fusion proteins, may be used as an immunogen to generate antibodies that recognize the translocation promoting agent protein. Such antibodies include but are not limited to polyclonal, monoclonal, chimeric, single chain, Fab fragments, and an Fab expression library. The anti-translocation promoting agent antibodies of the invention may be cross reactive, e.g., they may recognize translocation promoting agent from different species. Polyclonal antibodies have greater likelihood of cross reactivity. Alternatively, an antibody of the invention may be specific for a single form of translocation promoting agent, such as the murine translocation promoting agent. Preferably, such an antibody is specific for human translocation promoting agent. In Example 2 below, a particular monoclonal antibody was raised against Bonzo.

In a specific embodiment, an antibody of the invention is specific for a masked epitope on the translocation promoting agent that is exposed on binding to HIV or SIV. In another embodiment, an antibody of the invention is specific for an epitope created by the binding of the translocation promoting agent with HIV or SIV, and/or CD4, or both HIV or SIV and CD4. For example, the binding of HIV envelope protein to CD4 induces a conformational change in gp120 or gp130, which results in an increased affinity of gp120 or gp130 for Bonzo or BOB, and possibly a concomitant unmasking of a Bonzo or BOB epitope. Such antibodies can be selected on the basis of binding under conditions of HIV or SIV binding to the translocation promoting agent, e.g., at 4° C. to inhibit translocation, and screened for non-binding to the free translocation promoting agent.

Various procedures known in the art may be used for the production of polyclonal antibodies to the translocation promoting agent or derivative or analog thereof. For the production of antibody, various host animals can be immunized by injection with the translocation promoting agent, or a derivative (e.g., fragment or fusion protein) thereof, including but not limited to rabbits, mice, rats, sheep, goats, etc. In one embodiment, the translocation promoting agent or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the translocation promoting agent, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Nati. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology described in [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for a translocation promoting agent together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce translocation promoting agent-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for a translocation promoting protein, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a translocation promoting protein, one may assay generated hybridomas for a product which binds to a translocation promoting agent fragment containing such epitope. For selection of an antibody specific to a translocation promoting agent from a particular species of animal, one can select on the basis of positive binding with a translocation promoting agent expressed by or isolated from cells of that species of animal.

The foregoing antibodies can be used in methods known in the art relating to the localization and activity of the translocation promoting agent, e.g., for Western blotting, imaging translocation promoting agent in situ, measuring levels thereof in appropriate physiological samples, etc. using any of the detection techniques mentioned above or known in the art.

Suitable labels for antibodies (as well as for the other proteins, peptides and nucleic acids of the present invention) include enzymes, fluorophores (e.g., fluorescene isothiocyanate (FITC), phycoerythrin (PE), Texas red (TR), rhodamine, free or chelated lanthanide series salts, especially $Eu^{3+}$ green fluorescent protein, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker. In the instance where a radioactive label, such as the isotopes $^{3}H$, $^{14}C$, $^{32}P$, $^{35}S$, $^{59}Fe$, $^{90}Y$, $^{125}I$, $^{131}I$, and $^{186}Re$ are used, known currently available counting procedures may be utilized. In the instance where the label is a protein, e.g., an enzyme or fluorescent protein, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g., U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety including proteins comprising such moieties such as green fluorescent protein. In addition to these direct labeling devices, indirect labels comprising enzymes can also be used according to the present invention.

Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453. Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as $[^{35}S]$-methionine or $[^{32}P]$-orthophosphate. In addition to metabolic (or biosynthetic) labeling with $[^{35}S]$-methionine, the invention further contemplates labeling with $[^{14}C]$-amino acids and $[^{3}H]$-amino acids (with the tritium substituted at non-labile positions).

In a specific embodiment, antibodies that agonize or antagonize the activity of translocation promoting protein can be generated. Such antibodies can be tested using the assays for identifying ligands, for example.

Such antibodies, when conjugated with a toxin or radioactive element, can be used to target HIV-permissive cells for destruction. Thus, cells harboring HIV, particularly in its dormant phase, can be destroyed with antibodies, e.g., conjugated to a toxin such as ricin or a radioisotope such as $^{32}P$ or $^{125}I$, when such antibodies are specific for the translocation promoting protein.

Methods For Screening Drug Libraries

The present invention provides drug assays that rely on specific properties of translocation promoting proteins and/or Bonzo. In particular embodiments, cell lines expressing CD4 and one or more members of the chemokine receptor family, and more preferably Bonzo or BOB, are infected with an HIV-reporter virus or SIV-reporter virus that is pseudotyped with one or more selected envelope glycoproteins. Compound libraries are assayed for their ability to inhibit infection of the cells by the pseudotyped virus. Candidate compounds are selected and then counter-screened for non-specific effects on infection with virus pseudotyped with non-HIV or non-SIV envelope proteins such as MLV amphotropic env or with VSV-G env.

Cell lines include, but are not limited to murine 3T3 cells, human HeLa, U87MG, HOS, and 293 cells that are transgenically manipulated to express CD4. Additional human cell lines that do not normally express either CXCR4 or CKR-5 (such as SCL) can also be used. Additional cell lines are listed in Example 1, below.

HIV and SIV vectors include, but are not limited to HIV or SIV-luciferase, HIV or SIV-alkaline phosphatase, HIV or SIV-CD24 and HIV or SIV-2 LTR-Green Fluorescent Protein. In such vectors, the env gene can be inactivated by frame shifting, and the reporter gene is then inserted to replace the Nef open reading frame. Additional vectors can be made for easier screening in murine cells, in which expression of HIV-LTR-driven reporters is only about 1% of the level in human cells. Such vectors are based on the HIV-gpt prototype (Page et al. 1990), such that the reporter, e.g. luciferase is placed under control of the SV40 promoter within the env gene, ensuring high level expression following integration.

HIV-1 envelope glycoproteins whose tropism for CCRs and CXR4 have been determined are appropriate for screening for alternative translocating promoting agents. For example, CCR5-tropic envelope glycoproteins ADA and YU-2, (which can also use CCR3) 92US715, and 91US005 and one dual tropic for CXCR4 and CXCR5 (92HT593) are also able to infect cells tranfected with BOB. Two of the envelope proteins for primary HIV-1 strains (the dual tropic 92HT539 and CR5-tropic 92BRO25) also use Bonzo. In addition T-tropic envelope glycoproteins include HXB2, 92UG021, and 92HT599 also use BOB or Bonzo. Other CCR5-tropic envelope glycoproteins that do not use either BOB or Bonzo include BaL, 92UG975, 93HT966, 92RWO20, 93TH976, 92BRO20, and 93MW965. JRFL is a CCR5-tropic envelope glycoprotein that uses BOB only weekly. Envelope glycoproteins of SIV such as Mac1A11-Agm TY01, or Mac 239 can also be used to screen for receptors that are used by SIV.

In still other embodiments, drug assays are performed to identify agents that modulate the expression and/or function of Bonzo.

Identification of Potentially Therapeutic Compounds

Identification and isolation of a gene encoding a translocation promoting agent of the invention provides for expression of translocation promoting agent in quantities greater than can be isolated from natural sources, or in indicator cells that are specially engineered to indicate the activity of translocation promoting protein expressed after transfection or transformation of the cells. Accordingly, the present invention contemplates an alternative method for identifying agonists and antagonists of HIV translocation directed to modulating the activity of the translocation promoting agent using various screening assays known in the art. In one embodiment, such agonists or antagonists competitively inhibit HIV binding, or more particularly, an or SIV envelope protein binding to the translocation promoting agent; in another embodiment, the agonist or antagonist indirectly affects HIV translocation, whether by non-competitive binding to the translocation promoting agent, or by affecting the level of expression of the translocation promoting agent.

Any screening technique known in the art can be used to screen for antagonists of CD4-HIV or SIV envelope-translocation promoting agent association. The present invention contemplates screens for small molecule ligands or ligand analogs and mimics, as well as screens for natural ligands that bind to and antagonize such activity in vivo. For example, natural products libraries can be screened using assays of the invention for molecules that antagonize HIV-translocation promoting activity.

Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386–390 (1990); Cwirla, et al., *Proc. Natl. Acad. Sci.,* 87:6378–6382 (1990); Devlin et al., *Science,* 249:404–406 (1990)], very large libraries can be constructed ($10^{6-108}$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [14 *th International Congress of Biochemistry, Volume* 5, Abstract FR:013 (1988); Furka, Int. *J. Peptide Protein Res.* 37:487–493 (1991)], Houghton [U.S. Pat. No. 4,631,211, issued Dec. 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for translocation promoting protein ligands according to the present invention.

Alternatively, assays for binding of natural ligand to cells that express recombinant forms of a translocation promoting protein ligand binding domain, for Bonzo or BOB for example, can be performed. The soluble ligands can be provided readily as recombinant or synthetic proteins.

The screening can be performed with recombinant cells that express the translocation promoting agent, or alternatively, using purified protein, e.g., produced recombinantly, as described above. For example, the ability of a labeled, soluble or solubilized translocation promoting agent that includes the ligand-binding portion of the molecule, to bind ligand can be used to screen libraries, as described in the references cited above. In addition, orphan chemokines, potential chemokines, or potential ligands that are obtained from random phage libraries or chemical libraries, as described herein, can be tested by any of the numerous assays well known in the art and exemplified herein. In one particular embodiment of the present invention, an in situ assay is employed in which the detection of the calcium signaling elicited by the binding of a potential chemokine to a chemokine receptor is indicative of the chemokine having specificity for the chemokine receptor, and therefore is a ligand.

In addition, the present invention contemplates identifying modulators (e.g., agonists and antagonists) of Bonzo expression and/or function using various screening assays known in the art. In one embodiment, such modulators are identified through binding assays with Bonzo. Any screening technique known in the art can be used to screen for such modulators. The present invention further contemplates screens for small molecules as well as natural modulators that bind to and modulate Bonzo expression and/or function in vivo. As indicated above, phage libraries, chemical methods, synthetic libraries and/or commercial libraries also can be screened.

Screening can also be performed with recombinant cells that express a reporter gene that has been inserted in place of the coding sequence of Bonzo in the Bonzo gene locus. In a particular embodiment, the cells are obtained from a knockin mouse as described in Example 2 below. Such cells can be obtained by a number of methods well known in the art, including the isolation of cells from the bone marrow or blood of the mice. Alternatively, the knockin mice themselves can be used in the assay as described in Example 2 below.

Administration of the Therapeutic Compositions of the Present Invention

According to the present invention, the component or components of a therapeutic composition of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

Where administration of an antagonist to the Bonzo and/or BOB (CD4-gp120-gp41) complex is administered to prevent or treat AIDS, it is preferred for it to be introduced by injection into the blood. The antagonist may be a specific antibody raised against the Bonzo and/or BOB (CD4-gp120-gp41)complex or a mimic to Bonzo or BOB that competitively competes with Bonzo or BOB respectively, for the (CD4-gp120-gp41) complex. Alternatively the antagonist can be an antibody to Bonzo.

In another embodiment, the therapeutic compound can be delivered in a vesicle, in particular a liposome [see Langer, *Science* 249:1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing an antagonist to Bonzo or BOB.

In yet another embodiment, the therapeutic compound can be delivered in a controlled release system. For example, an antibody as described above, may be administered using intravenous infusion, an implantable osmotic pump, a transdermal patch, liposomes, or other modes of administration. In one embodiment, a pump may be used [see Langer, supra; Sefton, *CRC Crit. Ref Biomed. Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of a therapeutic target, e.g., the brain, thus requiring only a fraction of the systemic dose [see, e.g., Goodson, in *Medical Applications of Controlled Release*, supra, vol. 2, pp. 115–138 (1984)].

Other controlled release systems are discussed in the review by Langer [*Science* 249:1527–1533 (1990)].

Thus, a therapeutic composition of the present invention can be delivered by intravenous, intraarterial, intraperitoneal, intramuscular, or subcutaneous routes of administration. Alternatively, the therapeutic composition , properly formulated, can be administered by nasal or oral administration. A constant supply of the therapeutic composition can be ensured by providing a therapeutically effective dose (i.e., a dose effective to induce metabolic changes in a subject) at the necessary intervals, e.g., daily, every 12 hours, etc. These parameters will depend on the severity of the disease or condition being treated, other actions, such as diet modification, that are implemented, the weight, age, and sex of the subject, and other criteria, which can be readily determined according to standard good medical practice by those of skill in the art.

A subject in whom administration of the therapeutic composition is an effective therapeutic regiment for AIDS is preferably a human, but can be a primate with a related viral condition. On the other hand, agents that cause an increase in Bonzo/STRL 33 expression and/or function can be used in therapeutic compositions that enhance the immune response for a specific pathogen or that enhance the effect of a specific vaccine may be valuable for a wider number of species including humans, primates, farm animals, domestic pets etc. administering to an animal subject. Similarly, agents that cause a decrease in Bonzo/STRL 33 expression and/or function can be used to treat inflammation in a wide number of species.

Thus, as can be readily appreciated by one of ordinary skill in the art, the methods and pharmaceutical compositions of the present invention are particularly suited to administration to a number of animal subjects including humans.

Transgenic Vectors and Inhibition of Expression

In one embodiment, a gene encoding a translocation promoting agent, or antisense or ribozyme specific for translocation promoting agent mRNA (termed herein an "antigene") or a reporter gene can be introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus macrophage can be specifically targeted. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828 (1989)].

In another embodiment the gene or antigene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845.

In one embodiment, specific PBMCs are removed from an HIV-positive subject animal (e.g., a human) and the gene encoding Bonzo, for example, is replaced by a modified Bonzo gene that retains its natural activity but cannot translocate HIV-2. The subject animal is depleted of its corresponding PBMCs (e.g., if the gene modification was performed in a macrophage or T-cell, then the macrophages or T-cell are depleted) and the modified PBMCs are reintroduced into the subject animal. Such an animal subject should then have macrophages or T-cells, which are capable of responding to the appropriate natural ligand for Bonzo, but which are no longer susceptible to HIV-2 translocation/infection, via Bonzo. In a related embodiment, one or more additional translocation promoting agent genes (such as CC-CKR5 or CXCR4) are modified in a similar manner to more fully block HIV translocation/infection.

Targeted gene delivery is described in International Patent Publication WO 95/28494, published October 1995.

Alternatively, the vector can be introduced in vivo by lipofection [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988); Felgner and Ringold, *Science* 337:387–388 (1989)]. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

As noted above, the present invention extends to the preparation of antisense nucleotides and ribozymes that may be used to interfere with the expression of translocation promoting agent at the translational level. This approach utilizes antisense nucleic acid and ribozymes to block translation of a specific mRNA, either by masking that mRNA with an antisense nucleic acid or cleaving it with a ribozyme. Such antisense or ribozyme nucleic acids may be produced chemically, or may be expressed from an "antigene."

Antisense nucleic acids are DNA or RNA molecules that are complementary to at least a portion of a specific mRNA molecule [see Marcus-Sekura, *Anal. Biochem.* 172:298 (1988)]. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro [Marcus-Sekura, *Anal. Biochem.* 172:298 (1988); Hambor et al., *J. Exp. Med.* 168:1237 (1988)]. Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it [Cech, *J. Am. Med. Assoc.* 260:3030 (1988)]. Because they are sequence-specific, only mRNAs with particular sequences are inactivated.

Investigators have identified two types of ribozymes, Tetrahymena-type and "hammerhead"-type. Tetrahymena-type ribozymes recognize four-base sequences, while "hammerhead"-type recognize eleven-to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences encoding the translocation promoting agent can be used to prepare antisense molecules against and ribozymes that cleave mRNAs for translocation promoting agent, thus inhibiting expression of the gene encoding the translocation promoting agent, which can reduce the level of HIV translocation in macrophages and T cells.

Transgenic Mice

The transgenic mice of the present application can be produced as detailed in Killeen et al. (1993) EMBO 12 1547–1553, which is hereby incorporated by reference. The construction of the human $CD4^+$ murine $CD4^{31}$ mice are described by Killeen et al. (1993) EMBO 12 1547–1553. A Bonzo transgene is constructed using a human Bonzo minigene that includes all of the coding region exons and ~3 kb of sequence (including the first intron) upstream of the coding sequence. B6/SIL F2 eggs or B6/SIL F1× human $CD4^{30}$/murine $CD4^-$ eggs are microinjected with the human Bonzo transgene according to standard procedures described by Hogan et al. (1986). Founders are identified by Southern blotting using a human Bonzo cDNA probe.

Similarly the knockin mice can be prepared as described in Example 2 below.

Cells On Solid Support

Solid supports include glass beads, sugar beads (SEPHADEX, SEPHAROSE, Agarose, SEPHACEL etc.) magnetic beads, and dowex-type materials. Biological materials may be passed through cells bound to solid supports by common methods know to any person skilled in the art including but not limited by batchwise, by centrifugation, pressure-membrane filtration (e.g. Amicon or Millipore filtration) and through various types of columns.

The present invention may be better understood by reference to the following non-limiting Example, which is provided as exemplary of the invention. The following examples are presented in order to more fully illustrate the preferred embodiments of the invention. They should in no way be construed, however, as limiting the broad scope of the invention.

EXAMPLES

Example 1

Expression Cloning Of Novel Receptors Used By The Simian And Human Immunodeficiency Viruses Introduction Using an expression cloning strategy to identify SIV receptors, isolated genes encoding two members of the seven-transmembrane G-protein coupled receptor family were isolated that are used not only by SIV's, but also by strains of HIV-2 and M-tropic HIV-1. Both receptors are closely related to the chemokine receptor family and are expressed in lymphoid tissues. One of the receptors is also expressed in colon and thus may have a role in viral transmission. Use of these new receptors following experimental infection of non-human primates with SIV strains may provide important insight into viral transmission and mechanisms of SIV-and HIV-induced acquired immune deficiency syndrome.

Methods

Expression Cloning

A human T cell clone cDNA library L10/MX, in the retroviral vector pMX, was obtained from DNAX. High-titer retroviruses, produced by transient transfection of the library into the packaging cell line BOSC23 [Kitamura et al., *Proc. Natl. Acad. Sci. USA*, 92:9146–9150 (1995)], were used to infect NIH3T3 cells stably expressing human CD4. Briefly, 10 μg of the retroviral plasmid DNA was transfected into BOSC23 cells ($2 \times 10^6$ cells in a 10-cm culture dish) by calcium phosphate precipitation. Two days post transfection, the culture supernatant was collected, cleared of cell debris, and then added with 8 mg/ml polybrene to ten 10-cm dishes, each containing $5 \times 10^5$ 3T3.CD4 cells. After a 16 hour incubation at 37° C., the viral supernatant was replaced with DMEM-10% fetal calf serum. This high multiplicity infection resulted in 100% transduction of the 3T3.CD4 cells, as assayed in controls in which pMX.mCD4, (whose product is detectable by FACS analysis) was mixed in various ratios with the cDNA library. The library-transduced 3T3.CD4 cells were then transferred to 15-cm plates and were infected with a selectable replication-defective virus, HIV-puro, pseudotyped with either $SIV_{agmTY01}$ or $SIV_{mac1A11}$ Envs. HIV-puro pseudotypes were generated by transfecting 293T cells with 10 μg of pHIV-puro (an HIV construct in which env contains a frameshift mutation and nef has been replaced by the SV40 promoter regulating the puromycin resistance gene) and 10 μg of Env expressing plasmids. Virus-containing supernatants were harvested 48 hours post-transfection, filtered, and applied to the library-transduced 3T3.CD4 cells (10 ml viral supernatant per plate). After two days, the 3T3.CD4 cells were replated in 24-well plates ($1 \times 10^5$ cells per well) with medium containing 5 μg/ml puromycin. Selection medium was changed every 2 to 3 days, and visible colonies typically arose in 6 to 9 days. These colonies were then tested for their ability to be infected with HIV-luc pseudotyped with the HIV-1 M-tropic Env JRFL or SIV Envs from mac1A11 or agmTY01. Colonies infected by JRFL pseudotyped viruses were also stained with anti-CCR5 antibody.

Genomic DNA Isolation and PCR Cloning

To recover retrovirus-transduced cDNAs, 50 ng of genomic DNA isolated from each puromycin resistant clone was subjected to PCR. cDNA segments were amplified by using primers complementary to retroviral vector flanking the inserts (upstream 5'GGTGGACCATTCTCTAGACT, SEQ ID NO:13 and downstream 5'CCCTTTTTCTGGAGACTAAAT, SEQ ID NO:14). The PCR was set up using the Expand kit from Boehringer Mannheim and run for 35 cycles at 58° C. annealing temperature. The resulting PCR fragment was purified and cloned into the pCR3.1 vector (Invitrogen) and sequenced. Amino acid sequence alignments were analyzed using the DNASTAR program.

Pseudotyped Virus Infection Assays

Luciferase reporter viruses were prepared in 293T cells as described [Deng et al., 1996, supra; Landau et al., *J. Virol.*, 65:162–169 (1991)] using pNL-Luc-E⁻R⁻ vector and Env expression plasmids. Env expression vectors for HIV-1 JRFL, ADA, BaL, HXB2, 92UG021, 92US715, 92BR025, 92HT593, as well as SIV mac239, mac1A11 and agmTY01 have been described [Landau et al., 1991, supra; Westervelt et al., *Proc. Natl. Acad. Sci. USA*, 88:3097–3101 (1991); Hwang et al., *Science*, 257:535–537 (1992); Gao et al., *J. Virol.*, 70:1651–1657 (1996); Zingler et al., *J. Virol.*, 67:2824–2831 (1993)]. The HIV-2 ST24.1 and p7312A envelope expression plasmids were generated by PCR subcloning of the proviral DNA template into the expression plasmid pSP272. The HIV-2 UC1 envelope expression plasmids were synthesized by published procedures [Evans et al., *Science*, 240:1522–1525 (1988)] and UC2 [Barnett et al., *J. Virol.*, 67:1006–1014 (1993)]. Proviral DNAs from YU-2, HIV-2 ST/SXB1 [Kong et al., *Science*, 240:1525–1529 (1988)] and FO784 [Gao et al., *Nature*, 358:495–499 (1992)] were used in cotransfection with pNL-Luc-E⁻R⁻ vector to generate mixed viral particles containing both wild type and luciferase containing particles. Pseudotyped viruses in supernatants of transfected 293T cells were quantified by p24 ELISA (Coulter) to normalize virus stocks for infection. 293T cells transiently cotransfected with pMX.CD4 and with pBABE-puro expressing CCR1, BOB, Bonzo, CCR5, or CXCR4 [Deng et al., 1996, supra] were infected with pseudotyped viruses (50 ng p24 per infection, $5 \times 10^4$ cells per well in 24-well plates). 3T3.CD4 cells that stably express the different chemokine receptors [Deng et al., 1996, supra] were similarly infected. 3T3.CD4 cells expressing the new receptors were prepared by retroviral transduction with pMX.Bonzo and pMX.BOB. After 3 days, cells were harvested and resuspended in 120 μl of luciferase lysis buffer (Promega). The luciferase activity in 20 μl of lysate was assayed in a Wallac Microbeta 1450 Counter, using commercially available reagents (Promega).

Northern Blots

Polyadenylated RNA was prepared from various human cell lines with the Micro-Fast Track Kit (Invitrogen). Samples (5 μg of RNA) were electrophoresed through a 1% argarose-formaldehyde gel and transferred to a GeneScreen nitrocellulose membrane. Multiple tissue Northern blot I and II, purchased from Clontech, contains approximately 2 μg poly(A)⁺ RNA from each tissue. Integrity of blots was assayed by GAPDH probing. Full length cDNAs of BOB and Bonzo were labeled with $^{32}$P by the Random Primed DNA labeling Kit (Boehringer-Mannheim) and used to probe Northern blots.

Lymphocyte Purification and RT-PCR

Monocytes were purified from buffy coats using 46% percoll gradient. To purify T and B cell subsets, PBMC were stained with phycoerythrin conjugated anti-CD3 or anti-CD19 antibodies (Becton & Dickinson) and sorted using FACS (Coulter). Total RNA was isolated using RNAzol reagent (Cinna/Biotecx), treated with Rnase-free Dnase, and 0.5 μg was used for cDNA synthesis using Superscript II RNAse H reverse transcriptase and random hexamer primers (Gibco-BRL); one-twentieth of this reaction was used as a template for PCR amplification with Taq DNA polymerase. BOB primers used for RT-PCR: upstream (from ATG) 5'CATCTGCTCTTTGGTGATG (SEQ ID NO:15), downstream (550 bp from ATG) 5'GTATGGCTTATCATCAAT-CAGC (SEQ ID NO:16), amplifies ~600 bp transcript; Bonzo primers were: upstream (from 270 bp downstream of ATG) 5'CAGGCATCCATGAATGGGTGT (SEQ ID NO:17) and downstream (from stop codon) 5'CAAGGC-CTATAACTGGAACATG CTG (SEQ ID NO:18), amplifies ~750 bp transcript. The PCR reaction was run for 30 cycles at 94° C. for 40 seconds, 58° C. for 40 seconds, and 72° C. for 1 min. To exclude contamination of genomic DNA, control cDNA reactions in which reverse transcriptase was omitted were prepared in parallel. These were uniformly negative.

Results

An HIV-luciferase vector pseudotyped with SIV envelope glycoproteins (Envs) to infect several CD4+ cell lines was used to identify receptors used by SIV [Deng et al., *Nature*, 381:661–666 (1996)]. A murine 3T3.CD4 cell line expressing CCR5, but not CXCR4, was readily infected with viruses bearing Envs from either Rhesus macaque or African green monkey strains ($SIV_{mac1A11}$ or $SIV_{agmTy01}$, respectively) (FIG. 1a). The human astroglial U87.CD4 cell line, which does not express CCR5 or CXCR4 and is resistant to infection with pseudotypes displaying T-tropic HXB2 or M-tropic JRFL Envs [Clapham et al., *Virology*, 181:703–715 (1991)], was readily infectable with $SIV_{agmTY01}$ and, to a lesser degree, with $SIV_{mac1A11}$ Env-pseudotyped viruses (FIG. 1b). In contrast, CEM×174, a T cell/B cell hybrid that also lacks CCR5 expression and is commonly used to amplify SIV in culture [Stefano et al., *J. Virol.*, 67:6707–6715 (1993)], was preferentially infectable with $SIV_{mac1A11}$-pseudotyped virus (Table 1). A similar pattern was also observed in the Hut78 T cell line (Table 1), suggesting the presence of at least two additional receptors for SIV.

TABLE 1

Infection of T-cell Lines with SIV Isolates

| | Luciferase activity (c.p.s. × 10$^{-3}$) | | |
|---|---|---|---|
| Cell line | No Env | mac1A11 | agmTYO1 |
| CEM | <1 | 21 | 736 |
| CEMx174 | <1 | 2,025 | 191 |
| Hut78 | <1 | 145 | 51 |

Infection of transformed CD4+ cell lines was done by using HIV-luciferase-reporter virus pseudotyped with SIV Env proteins. Values are the average of duplicate determinations. Standard deviations were less than 15% of the average value.

Figure 2A:
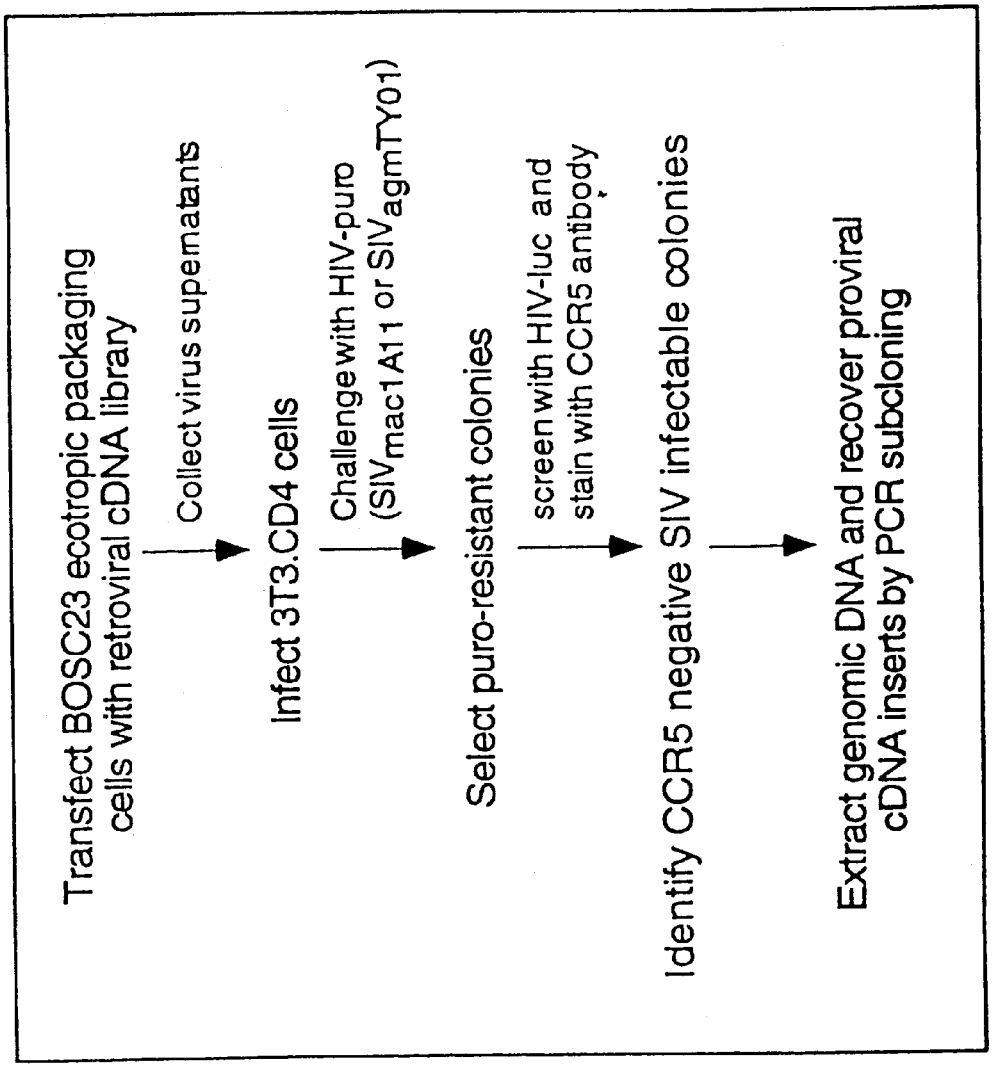
Figure 2C:
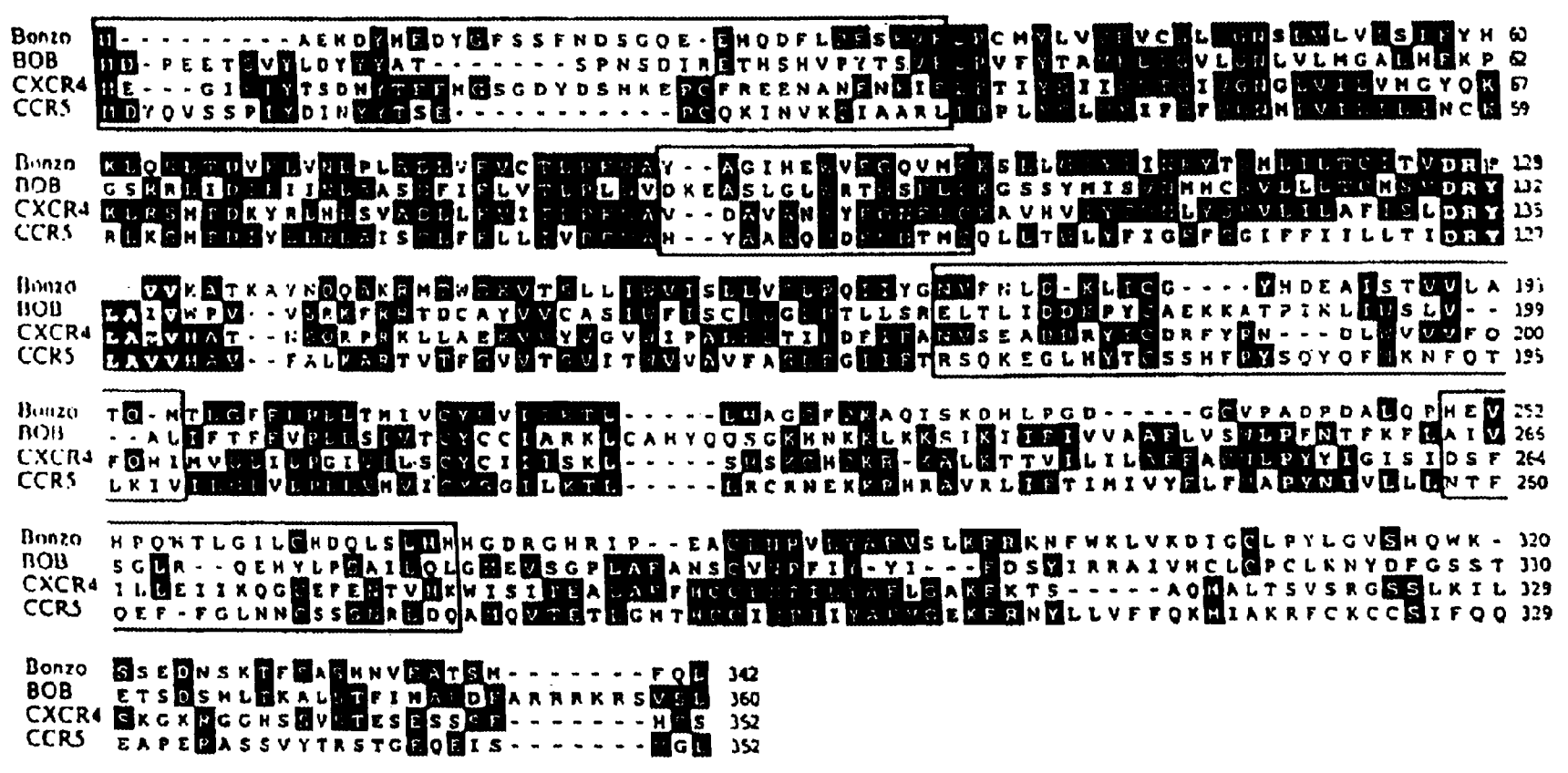

An expression cloning strategy, as outlined in FIG. 2a was employed to isolate the genes encoding such receptors. A human T cell clone cDNA library, subcloned in the retroviral vector pMX (obtained from DNAX), was transfected into BOSC23 packaging cells and supernatant from these cells was then used to infect 3T3.CD4 cells. The transduced 3T3.CD4 cells were in turn challenged with a selectable replication-defective virus (HIV-puro) pseudotyped with either the $SIV_{agmTY01}$ or $SIV_{mac1A11}$ Envs followed by puromycin selection. A total of 280 puromycin resistant colonies were obtained with the $SIV_{agmTY01}$ infection and about 170 with the $SIV_{mac1A11}$ infection. These colonies were then tested for their ability to be infected with HIV-luc pseudotyped with the HIV-1 M-tropic Env JRFL. Representative results after infection of several candidate colonies with virus bearing SIV or HIV Envs are shown in FIG. 2b. Approximately 10% of the $SIV_{agmTY01}$-selected and 90% of the $SIV_{mac1A11}$-selected colonies were infectable with the JRFL Env pseudotypes, and all of these JRFL Env infectable colonies were shown by PCR and antibody staining to express CCR5 (e.g. clones C1.193 and C2.219 in FIG. 2b). Genomic DNAs extracted from CCR5-negative colonies were subjected to PCR amplification using the primers flanking inserts in the pMX retroviral vectors. A common 2.1 kb band was detected with $SIV_{agmTY01}$-selected colonies, and a common 2.2 kb band with $SIV_{mac1A11}$-selected colonies. The PCR products were subcloned into expression vector pCR3.1 (Invitrogen), and the DNA sequences were determined. The cDNA selected with the $SIV_{amgTY01}$ pseudotypes was found to encode a novel protein of 342 amino acids, Bonzo; whereas its counterpart selected with the $SIV_{mac1A11}$ pseudotypes encodes a protein of 360 amino acids, designated BOB (Brother of Bonzo). Comparison of these sequences with those in genome databases indicates that both molecules are members of the large family of G-protein coupled receptors. BOB is identical to a previously cloned orphan receptor, GPR15 [Heiber et al. *Genomics*, 32:462–465 (1996)], whereas Bonzo is a novel gene with no identity to sequences in the expressed sequence tag (EST) databases. Both BOB and Bonzo are related to the chemokine receptor family proteins, however, they share only 20–25% amino acid sequence identity with CCR5 and CXCR4. Sequence alignments of these receptors and of CCR5 and CXCR4 are shown in FIG. 2c. Homologues of the SIV receptors from African green monkey and pigtail macaque were also cloned using specific primers. These were found to be 94–97% identical to the human sequences.

Figure 3A:
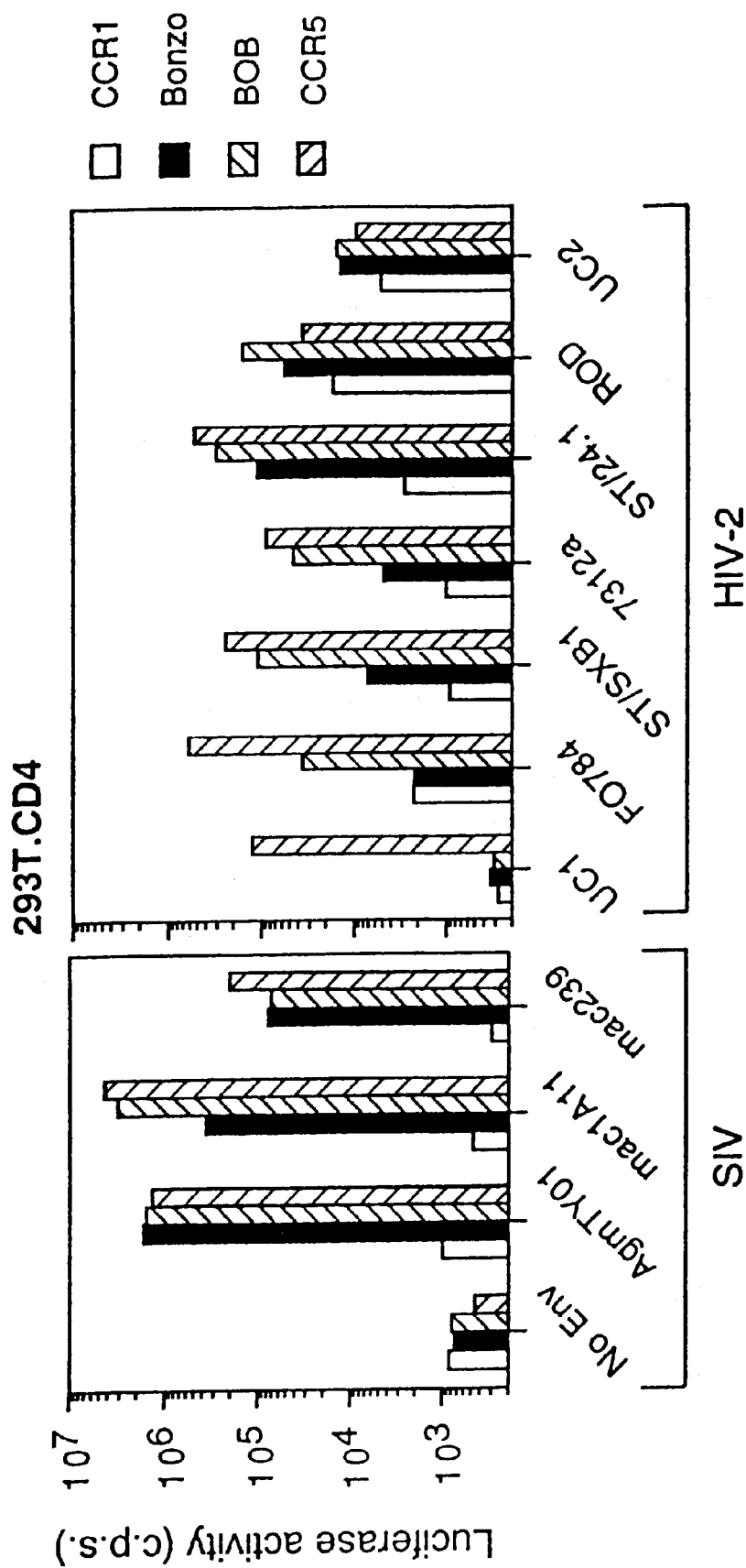
FIGS. 3a–3c shows that BOB and Bonzo mediate entry of SIV, HIV-2 and M-tropic or dual-tropic HIV-1 strains.
Figure 3B:
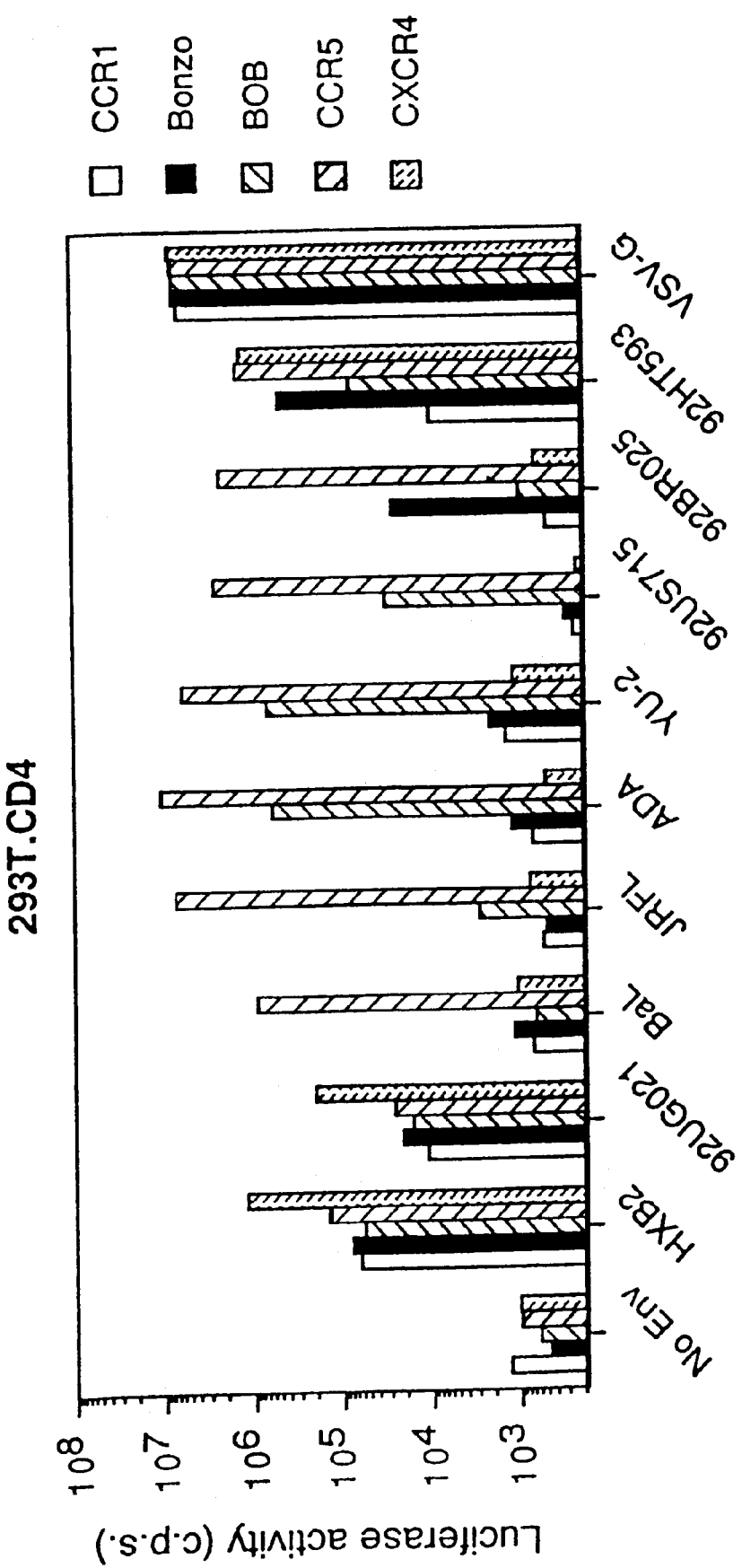
Figure 3C:
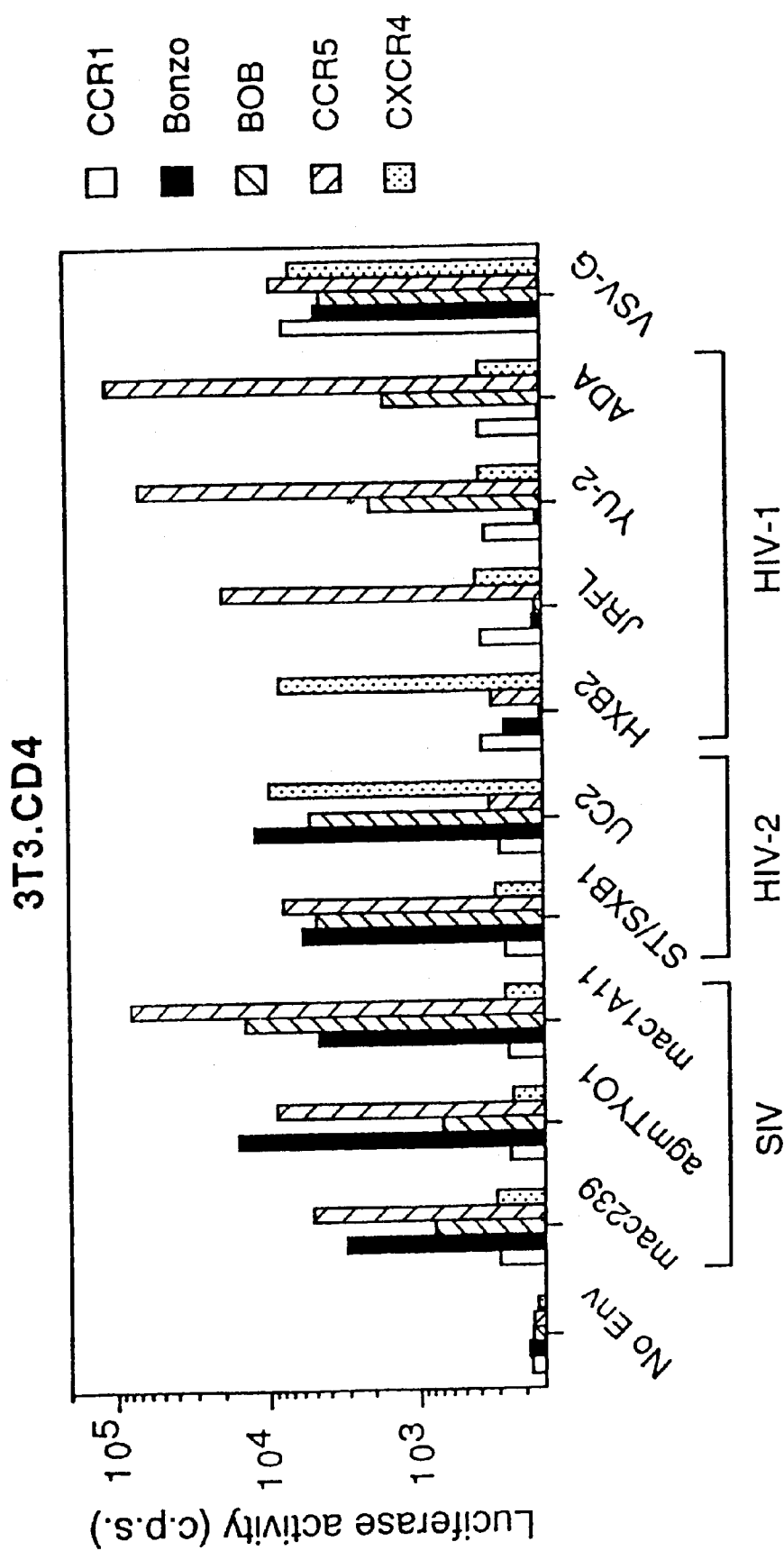

To test the viral receptor function of the newly identified molecules, their cDNAs were cloned into the pBABE-puro expression vector and were transiently transfected into human 293T cells along with human CD4. Cells were separately transfected with vectors encoding CCR5 or CCR1 as controls. Transfected cells were then infected with HIV-luc viruses pseudotyped with Envs from a diverse set of SIV, HIV-2, and primary HIV-1 isolates. As shown in FIG. 3a, the three SIV envelopes tested were all able to use Bonzo, BOB, and CCR5. The inability of SIV Env-pseudotyped virus to infect CCR1-transfected control cells also shows that none of the SIV Envs tested can use CXCR4, which is expressed endogenously in 293T cells. Most of the HIV-2 Envs tested were also able to use BOB (FIG. 3a). Several HIV-2s that grow on transformed T cell lines can also use CXCR4, thus explaining their high background in 293T cells (e.g. ROD and UC2). Most of the HIV-2 envelopes tested were able to use CCR5 to varying degrees, with the exception of UC2, which exclusively uses CXCR4. The specificities of the different HIV-2 Envs have been confirmed in infections of 3T3.CD4 cells, as discussed below (FIG. 3c).

Next a panel of HIV-1 envelopes whose tropism for CCRs and CXCR4 had been previously determined were examined. Several CCR5-tropic Envs (ADA and YU-2, which an also use CCR3 [Choe et al., *Cell*, 85:1135–1148; He et al., *Nature*, 385:645–649 (1997)], 92US715, and 91US005) and one dual-tropic for CXCR4 and CCR5 (92HT593) were also able to infect cells transfected with BOB (FIG. 3b). Two of the Envs from primary HIV-1 strains (the dual tropic 92HT593 and the CCR5-tropic 92BR025) also utilized Bonzo (FIG. 3b). None of the three T-tropic envelopes tested (HXB2, 92US021, and 92HT599) was found to use BOB or Bonzo. Several other CCR5-tropic Envs (BaL, 92UG975, 93HT966, 92RW020, 93TH976, 92BR020, and 93MW965) also did not use these receptors, and one (JRFL) used BOB only weakly (FIG. 3b).

Infection of 293T cells with viruses using CXCR4 results in high background due to expression of endogenous CXCR4 (e.g. HIV-2 UC2 in FIG. 3a). Therefore Bonzo, BOB, CCR5 and CCR1 were stably introduced into mouse 3T3 cells expressing hCD4, and these were infected with the panel of HIV-luc pseudotype viruses (FIG. 3c). The infection results were consistent with those obtained from the transient transfections of 293T cells. The $SIV_{mac1A11}$-pseudotyped virus infected cells expressing BOB more effectively than cells expressing Bonzo, while the converse was observed with virus bearing SIV$_{agmTYo1}$ Env. Infection of human osteosarcoma cells, expressing CD4 and either BOB, Bonzo or CCR5, with replication competent SIV$_{agm}$ and SIV$_{mac}$ strains yielded similar results.

Next the expression pattern of the newly identified receptors was determined in normal human tissues using Northern blot hybridization (FIG. 4a). Bonzo cDNA hybridized to a 2.1 kb mRNA species expressed at high levels in spleen, thymus, small intestine, and, to a lesser extent, in peripheral blood leukocytes, prostate and colon. In the placenta, a 2.6 kb species was detected. This species either represents a different homologous gene product, a product of differential splicing, or an antisense mRNA. Similarly, BOB mRNA was detected in spleen and peripheral blood leukocytes, and weaker expression was detected in thymus and small intestine. Interestingly, BOB mRNA was present in colon, where its high level suggests that it may be expressed in non-lymphoid cells. It will therefore be important to determine if this expression pattern is relevant for sexual transmission of HIV.

Expression of the newly identified receptors was also analyzed in PBMC and in FACS-purified subsets by RT-PCR (FIG. 4b). Expression of Bonzo mRNA was evident in unstimulated and PHA-stimulated PBMC, T cells, and monocytes, but not in B cells. BOB mRNA was detected in PHA-stimulated PBMC, purified T cells, and weakly in unstimulated PBMC. However, expression was either minimal or absent in monocytes and B cells.

The role of the novel receptors in regard to the susceptibility of various cell lines to infection with SIV was examined next. Northern blot analysis of RNA from cell lines shows that CEM×174 cells, the parental 174 cells, and Hut78 cells express high levels of BOB, but not Bonzo (FIG. 4c). This pattern of expression correlates with the preferential infection of CEM×174 and Hut78 cells by the SIVs from rhesus macaque. Low levels of Bonzo mRNA could be detected in CEM and U87 cells, both by Northern analysis (FIG. 4c) and by RT-PCR. Furthermore, antiserum raised against the N-terminal sequence of Bonzo blocked infection of U87.CD4 and CEM cells with HIV-luc pseudotyped with SIV Envs. The expression pattern of Bonzo thus explains the ability of these cells to be infected with African green monkey strains of SIV.

The finding that envelope glycoproteins from both HIV-1 and HIV-2 primary strains can use Bonzo and BOB as receptors implies that these receptors have important roles in infection of humans. Recent reports have also described CCR5$^{-/-}$ homozygous individuals who are infected with HIV-1 [Theodorou et al., Lancet., 349:1219–1220 (1997); Biti et al., Nat. Med., 3:252–253 (1997); O'Brien et al., Lancet., 349:1219 (1997)]. In light of our finding that several M-tropic strains can efficiently use the novel receptors, especially BOB, it is tempting to speculate that these receptors may substitute for CCR5 in the establishment of HIV-1 infection. It is possible, however, that these individuals are infected with CXCR4-tropic viruses. SIV was recently shown to replicate in human CCR5-deficient PBMC [Chen et al., J. Virol., 71:2705–2714 (1997)]. Based on the results presented here, this is most likely explained by the ability of SIVs to use Bonzo and/or BOB as receptors in the mutant cells. It is likely that the HIV-1 recovered from infected CCR5-negative individuals can likewise utilize these newly identified receptors.

There are now six members of the chemokine receptor family that have been shown to function in HIV-1 entry: CCR5, CXCR4, CCR2b, CCR3, Bonzo, and BOB. Application of the expression cloning approach described here is likely to result in identification of additional receptors when primary HIV-1 Envs and expression libraries from other tissues are used in the screening. The ability of HIVs to infect cells by way of the newly-described receptors, which are expressed in human T lymphocytes and monocytes, may significantly complicate strategies aimed at blocking CCR5-tropic virus entry.

Example 2

The Primate Lentiviral Receptor Bonzo/Strl33 Is Coordinately Regulated With Ccr5 And Its Expression Pattern Is Conserved Between Human And Mouse Introduction Chemokine receptors belong to a subset within the superfamily of seven transmembrane domain (7TM) G-protein-coupled receptors which generally function to direct the complex migratory or trafficking patterns of leukocytes [Murphy, Cytokine Growth Factor Rev 7.47 (1996), Ward et al. Immunity 9:1 (1998)]. Most chemokines are small secreted proteins that are grouped according to the highly conserved position of cysteine residues within their N-terminal region into C, CC, CXC, and CX$_3$C families [Schall et al., Curr Opin Immunol 6:865 (1994), Baggiolini et al., Annu Rev Inmunol 15:675 (1997), Baggiolini, Nature 392:565 (1998)]. Chemokines play necessary and important roles in regulating the trafficking of lymphocytes to intra or inter-lymphoid tissues as well as to sites of inflammation. The complex migratory patterns of lymphoid lineage cells is governed by subset-specific expression of chemokine receptors and by their access to specific ligands. Several chemokine receptors and chemokine receptor-like orphan receptors also serve, in conjunction with CD4, as coreceptors for infection by human and simian immunodeficiency viruses (HIV and SIV).

Although chemokine receptors often exhibit multiple ligand specificities, this "promiscuity" is generally limited to the binding of chemokines within the same family [Ward; et al. Immunity 9:1 (1998)]. Because of this, chemokine receptors are classified based on the family of chemokines that they bind. Greater sequence homology also exists within each of the CC and CXC families of chemokine receptors than between the two families. Moreover, the CC chemokine receptors CCR1–CCR5, CCR8, CCR9/10 and CX$_3$CR1 are closely linked on chromosome 3p21 [Raport et al. Gene 163:295 (1995), Samson et al., Genomics 36:522 (1996), Daugherty et al. Genomics 41:294 (1997), Bonini et al., DNA Cell Biol 16:1249 (1997), Roos et al., J Biol Chem 272:17251 (1997)].

Members of the chemokine receptor family also serve as coreceptors, in conjunction with the CD4 molecule, for entry of HIV and SIV into target cells [Feng et al., Science 272:872 (1996), Alkhatib et al., Science 272:1955 (1996), Deng et al., Nature 381:661 (1996), Dragic et al., Nature 381:667 (1996), Doranz et al., Cell 85:1149 (1996), Choe et al., Cell 85:1135 (1996)]. CCR5 is the major coreceptor for R5 strains (previously referred as M-tropic) of HIV-1 and most SIV strains, while CXCR4 allows entry of X4 strains (previously referred as T-tropic) of HIV-1 [Feng et al., Science 272:872 (1996), Alkhatib et al., Science 272:1955 (1996), Deng et al., Nature 381:661 (1996), Dragic et al., Nature 381:667 (1996), Doranz et al., Cell 85:1149 (1996), Choe et al., Cell 85:1135 (1996)]. Additionally, CCR2, CCR3, CCR8 and CX3CR1 have been reported to be used by some of the HIV/SIV isolates, albeit at lower efficiencies [Rucker et al., *J Virol* 71:8999 (1997), Unutmaz et al., *Semin Immunol* 10:225 (1998), Choe et al., *Semin Immunol* 10:249 (1998)]. Several chemokine-receptor-like orphan receptors have also been shown to function as coreceptors for HIV and SIV strains [Deng et al., *Nature* 388:296 (1997), Loetscher et al., *Curr Biol* 7:652 (1997), Liao et al., *J Exp Med* 185:2015 (1997), Alkhatib et al., *Nature* 388:238 (1997)]. One of these 7TM orphan receptors, Bonzo (also named STRL33 or TYMSTR), was identified as a principal coreceptor for several strains of SIV (including SIVagm and SIVsm family viruses) as well as some HIV-2 and HIV-1 strains [Deng et al., *Nature* 388:296 (1997), Loetscher et al., *Curr Biol* 7:652 (1997), Liao et al., *J Exp Med* 185:2015 (1997), Alkhatib et al., *Nature* 388:238 (1997)]. Bonzo is a putative chemokine receptor based on sequence homology with other chemokine receptor family members. However, its biological function is not understood and no natural ligand has yet been identified among the known human chemokines [Loetscher et al., *Curr Biol* 7:652 (1997)]. Expression of Bonzo mRNA is restricted to lymphoid tissues, PBMC and placenta [Deng et al., *Nature* 388:296 (1997), Loetscher et al., *Curr Biol* 7:652 (1997), Liao et al., *J Exp Med* 185:2015 (1997), Alkhatib et al., *Nature* 388:238 (1997)]. Interestingly, the Bonzo gene maps to human chromosome 3 close to the region where genes encoding CC family chemokine receptors are clustered [Loetscher et al., *Curr Biol* 7:652 (1997)]. Little is known about the cell subset specific expression and regulation of Bonzo. The in vivo distribution of Bonzo-expressing cells and the modulation of this expression may be important in determining the role of Bonzo in SIV and HIV pathogenesis.

Materials and Methods

Generation Of mAb Against Bonzo

A monoclonal antibody against Bonzo/STRL33 was raised at R&D systems by immunizing BALB/c mice with a syngeneic mouse myeloma (NSO) transfected with full-length human Bonzo/STRL-33 with a poly-histidine fused to the C-terminal end of the receptor sequence. The poly-his serves as an epitope tag which can be used to identify (via intracellular staining in FACS, or via western blot) transfected clones that appear to be expressing high levels of the gene of interest. An immunization protocol [Lucas et al., *J. Immunol* 145:1415 (1990)] for soluble protein was adapted for use with whole cells as the immunogen. The priming immunization was done by mixing the cell suspension in PBS with an equal volume of emulsified MPL/TDM adjuvant (Ribi); subsequent boosts used cells in PBS alone. Following immunization, lymph node cells were used for PEG-mediated fusion following conventional protocols. After 7 days of culture, supernatants were screened for antibodies that could bind to paraformaldehyde fixed NSO/STRL-33/poly-His cells used for immunization. Cultures that were positive in this primary screen were then tested for binding to NSO cells that had been transfected with an irrelevant gene (GDF-9) also expressed as a poly-his construct. One clone was chosen and subcloned based on strong binding of its supernatant to the unfixed relevant transfectants. This hybridoma secretes an IgG2b, κmAb that was purified and used in subsequent experiments. This antibody is designated as MAB699.

Preparation of Human PBMC and Resting T cells

PBMC were separated from buffy coats of healthy donors (New York Blood Bank) through Ficoll-Hypaque (Pharmacia, Uppsala, Sweden). Purification of T cells was performed as described [Unutmaz et al., *J Exp Med* 189:1735 (1999)]. Briefly, monocytes were first removed from PBMC by plastic adherence for two hours at 37° C. Non-adherent cells were incubated with anti-CD4 or anti-CD8 conjugated with DYNABEADS (Dynal, Oslo, Norway) at a 1:4 target/bead ratio. The bead-bound cells were recovered using a magnet (Dynal) washed at least 4 times to remove unbound cells. The $CD4^+$ or $CD8^+$ cells were detached from the beads using DETACHABEAD according to the manufacturer's instructions (Dynal). These cells were then incubated with anti-HLA-DR antibody followed by DYNABEADS conjugated with goat-anti-mouse IgG for magnetic removal of pre-activated T cells and contaminating dendritic cells or macrophages.

Media, Reagents and T Cell Cultures

The culture media used in all experiments was RPMI (Gibco) supplemented with 10% FCS (Hyclone), penicillin (50 U/ml, Gibco), streptomycin (50 µg/ml), Sodium pyruvate (1 mM, Gibco) and Glutamine (2 mM, Gibco). T cell lines were prepared by activation of purified resting T cells with allogeneic PBMC, treated with 50 µg/ml mitomycin-C (Sigma) for 30 min at 37° C., and 5 µg/ml PHA (Sigma). Cells were split three days post activation, expanded and maintained in culture media supplemented with 200 U/ml recombinant IL-2 (Chiron). T cell lines were maintained by restimulating the cells every two weeks with PHA and mitomycin C-treated allogeneic PBMCs. Culture of T cells with cytokines has been previously described [Unutmaz et al., *J Exp Med* 180:1159 (1994), Unutmaz et al., *J Exp Med* 189:1735 (1999)]. Cytokines IFNγ, IL-4, IL-7, IL-12 and IL-15 and chemokines RANTES, MIP-1α, MIP-1β, and SDF-1α were all obtained from R&D Systems (Minneapolis, Minn.).

Antibody Staining and FACS Analyses

Cells were incubated with the relevant antibody on ice for 30 min in PBS buffer with 2% FCS and 0.1% NaAzide. For staining of Bonzo, cells were incubated with anti-Bonzo mAb at 3 µg/ml; after two washes, cells were incubated with goat-anti-mouse IgG conjugated to PE or TC (Caltag). The cells were washed twice again and blocked with excess mouse IgG (100 µg/ml) followed by staining with directly conjugated antibodies against the relevant cell surface molecules. The antibodies used for staining were, PE, FITC, TC or PercP conjugates of: anti-human CCR5 and anti-human CXCR4, anti-mouse CD3, CD4, CD8, CD44, CD45RB, γδTCR (Pharmingen), anti-human CD4 and CD45RO, secondary antibodies goat-anti-mouse PE or FITC (Caltag), anti-human CD3, CD8, CD14, CD16, CD19, CD45RA, HLA-DR and γδTCR (all from Becton & Dickinson), or anti-human CCR6 (R&D Systems). Staining was analyzed on a FACScan® using CellQuest software. Live cells were gated based on forward and side scatter. Intracellular staining was performed using-Cytofic/Cytoperm solution according to manufactures protocol (Pharmingen). To perform FACS analyses on fresh human thymocytes, thymi were obtained during 7–9 months of age pediatric heart surgery cases. Thymic tissue was disrupted by mincing and forcing through stainless-steel mesh. Thymocytes were incubated, twice, at 37° C. for 30 min in complete medium to remove adherent cells. Single cell suspensions were then placed on ice and stained for FACS analysis as described above.

Gene Targeting in Embryonic Stem Cells and Generation of Mice

A 129/Sv mouse genomic DNA library was screened with human Bonzo cDNA and a 16 kb DNA fragment was isolated. Sequence analysis identified a 1.2 kb intronless open reading frame (ORF) homologous to that of the human Bonzo gene. To generate an EGFP (Clontech) knock-in targeting vector, three DNA fragments were sequentially inserted into a pBS-KS+ plasmid:

(1) a GFP expressing cassette followed by SV40 poly(A)n sequence;

(2) a neomycin resistance cassette (neo$^R$) flanked with loxP sites [Beverley, Semin Immunol 4:35 (1992)]; and (3) a herpes simplex virus thymidine kinase cassette (HSV-TK).

Subsequently, an 8 kb ApaI-NotI genomic fragment downstream of the Bonzo ORF was inserted between the neoR and HSV-TK cassettes, whereas a 1.6 kb genomic fragment upstream of the Bonzo ORF and containing the 5' untranslated region was inserted 5' of the GFP ORF. The resulting targeting vector was linearized with ClaI and electroporated into 129/Sv-derived E14 embryonic stem (ES) cells. G418 resistant ES cell clones were then screened for homologous recombination. In order to eliminate possible interference from the neo gene, correctly targeted clones were electroporated with a Cre recombinase-expressing vector (pCMV-Cre) to delete the neo$^R$ cassette, which was confirmed by sensitivity to G418 and by PCR or Southern blotting for the absence of the neo$^R$ coding region. The resulting clones were microinjected into C57Bl/6 blastocysts. Chimeric mice were mated with wild-type C57BL/6 mice to produce heterozygous progeny. Six-to eight-weeks old littermates from the mating of heterozygous mice were then analyzed.

Reverse Transcription-coupled PCR (RT-PCR) Analysis

Total RNA was extracted from mouse lymph nodes and spleen using Trizol reagent (Gibco BRL). The RNA was further treated with RNase-free DNase I (Boehringer Mannheim). 1$\mu$g of RNA was used in an Access RT-PCR system (Promega) with 50 pmol of sense (GCT TGC TCA TTT GGG TG, SEQ ID NO:19) and anti-sense (CGC CGC GTC GAC CTT CTC TAA GTG TGG CAA GGC, SEQ ID NO:20) Bonzo primers. Reverse transcription was performed for 45 min at 48° C., and cDNA amplification was carried out for 40 cycles at 94° C. for 30 seconds, 58° C. for 1 minute, 68° C. for 2 minutes. To exclude possible contamination with genomic DNA, control reactions in which reverse transcriptase was omitted were done in parallel.

Fluorescence Microscopy

Mouse organs were fixed in 4% formaldehyde for at least 12 hours and incubated in 15% sucrose in PBS for 1 hour. The samples were embedded in Histo Prep (Fisher) and later frozen with dry ice. Samples were cut into 15 $\mu$M sections with a Cryostat. Fluorescence microscopy was used to visualize GFP expression.

Results

Bonzo Expression Pattern on PBMC

Figure 5:
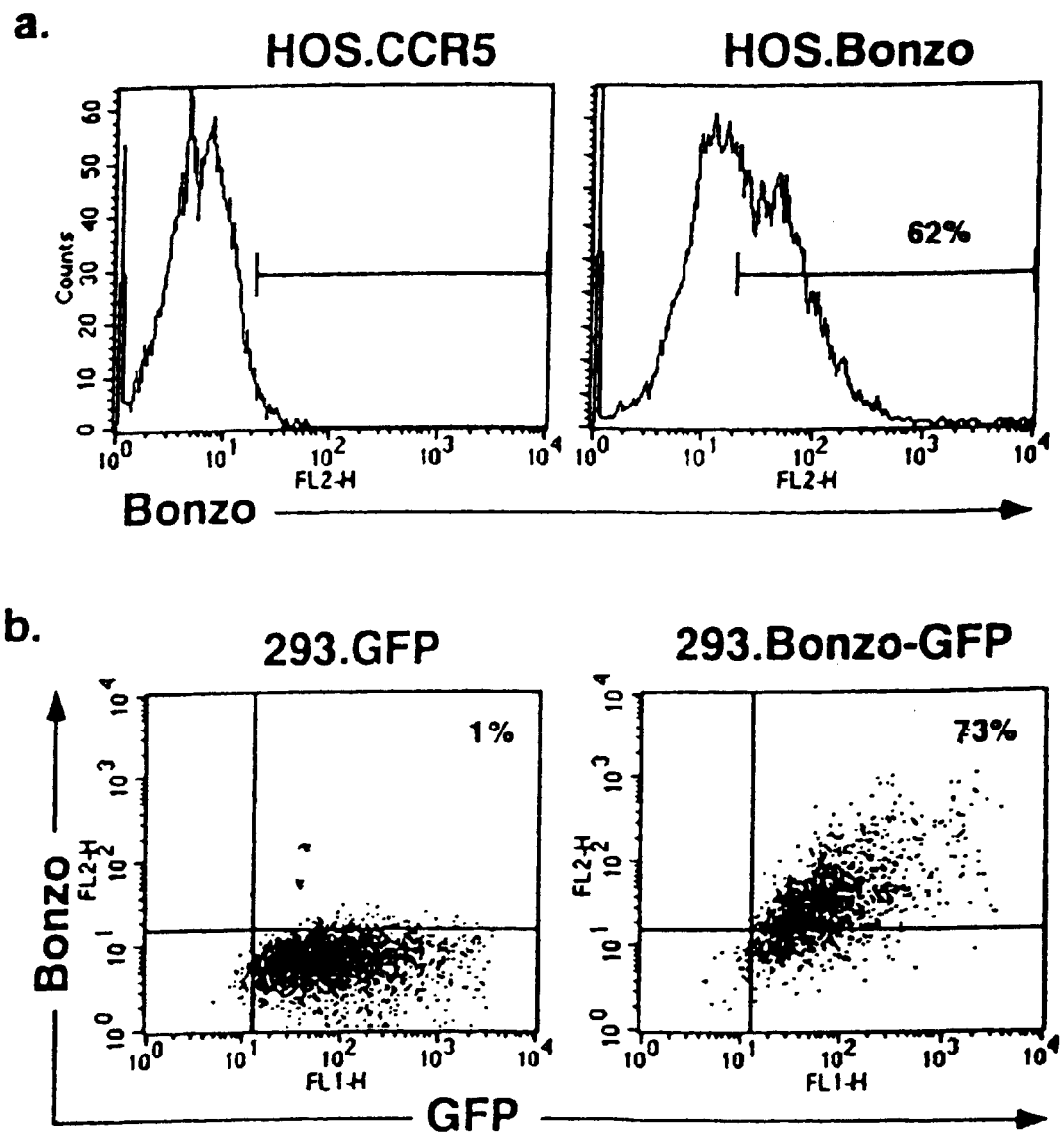
FIGS. 5a–5b show that the Bonzo antibody specifically stains transfected cells.
Figure 6:
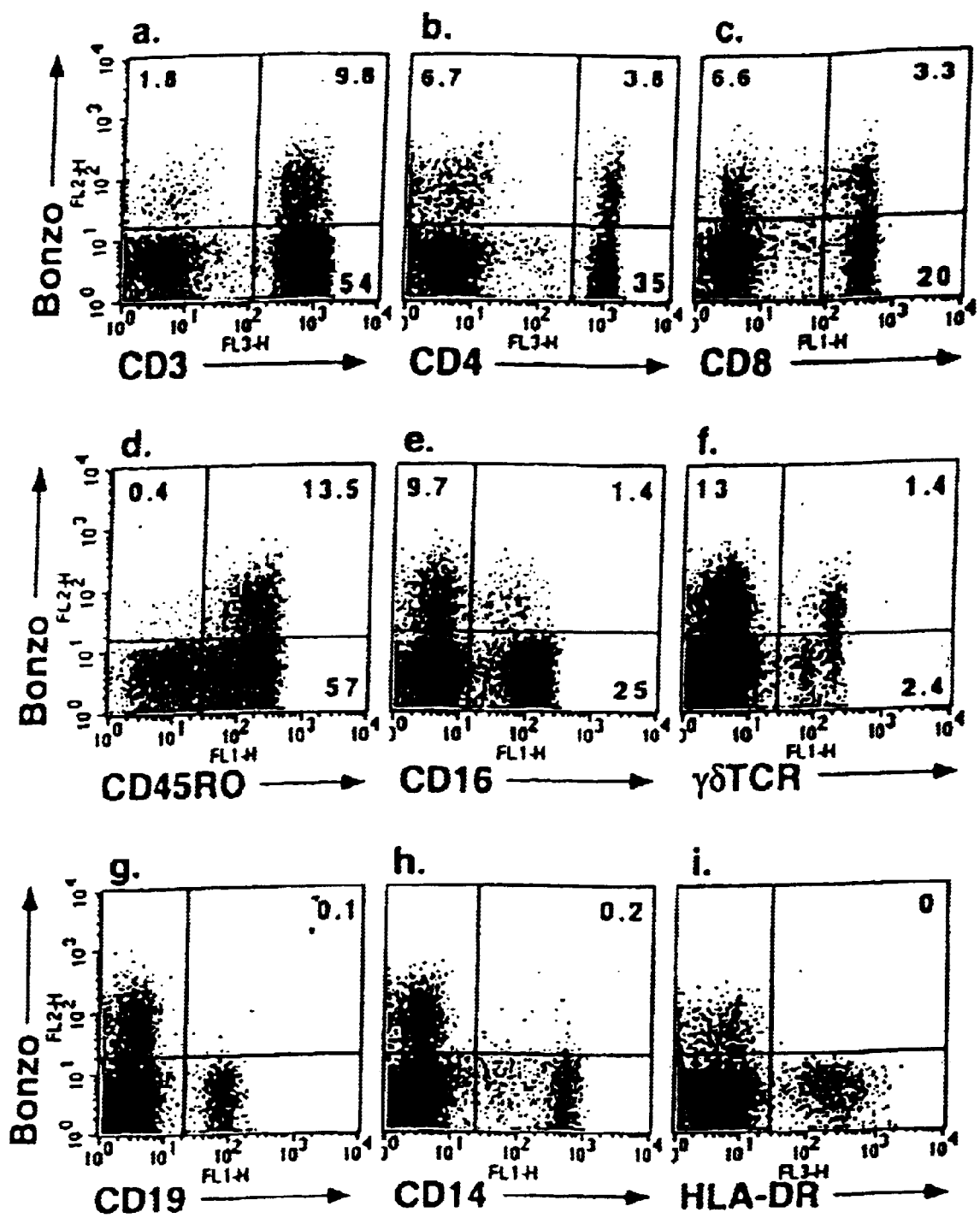
FIGS. 6a–6i show the expression of Bonzo on PBMC. Freshly isolated PBMC were stained with anti-Bonzo mAb followed by the PE conjugated secondary antibody and were subsequently stained with PE-conjugated antibodies specific for other cell surface molecules. Three donors gave similar results and data from one donor is shown. Numbers in quadrants are percent positives. Expression of Bonzo on FIG. 6a T cells (CD3$^+$).

A monoclonal antibody reacting against human Bonzo was obtained as described in the Materials and Methods. This antibody binds specifically to HOS cells that stably express the Bonzo cDNA (FIG. 5A) [Deng et al., Nature 388:296 (1997)]. Similar results were obtained using Bonzo-transduced NIH.3T3 cells or a mouse thymoma line. In addition, 293T cells were transfected with a plasmid encoding Bonzo-GFP fusion and stained with anti-Bonzo antibody. Only Bonzo-GFP expressing cells were positively stained with anti-Bonzo mAb and this correlated with GFP expression. In order to exclude the cross-reactivity of the antibody with other chemokine receptors HOS cell lines that stably expressed CCR1, CCR3, CCR4, CCR7, CCR8, APJ and V28 were also stained. None of these cell lines were stained with anti-Bonzo mAb. The expression pattern of Bonzo was then determined on PBMC of normal donors using multi-color FACS analysis. Expression of Bonzo was found to segregate primarily to CD3$^+$ T cells (FIG. 6a). Both CD4$^+$ and CD8$^+$ T cell subsets expressed Bonzo (FIG. 6b and 6c), although the percentage of Bonzo$^+$ cells was always higher within the CD8$^+$ subset in samples obtained from different donors. T cells can also be subdivided into memory and naive subsets based on expression of CD45 isoforms, CD45RO$^+$RA$^-$ and CD45RO$^-$ RA$^+$ respectively [Bleul et al. Proc Natl Acad Sci USA 94:1925 (1997)]. Bonzo was exclusively expressed on CD45RO$^+$ T cells (FIG. 6d). About 30–40% of $\gamma\delta$ T cells also expressed Bonzo (FIG. 6f). The few CD3-negative cells that expressed Bonzo were found to be CD16$^+$ NK cells (FIG. 6e) and no expression was detected on B cells, monocytes or dendritic cells (FIGS. 6g, 6h and 6i respectively).

Figure 7:
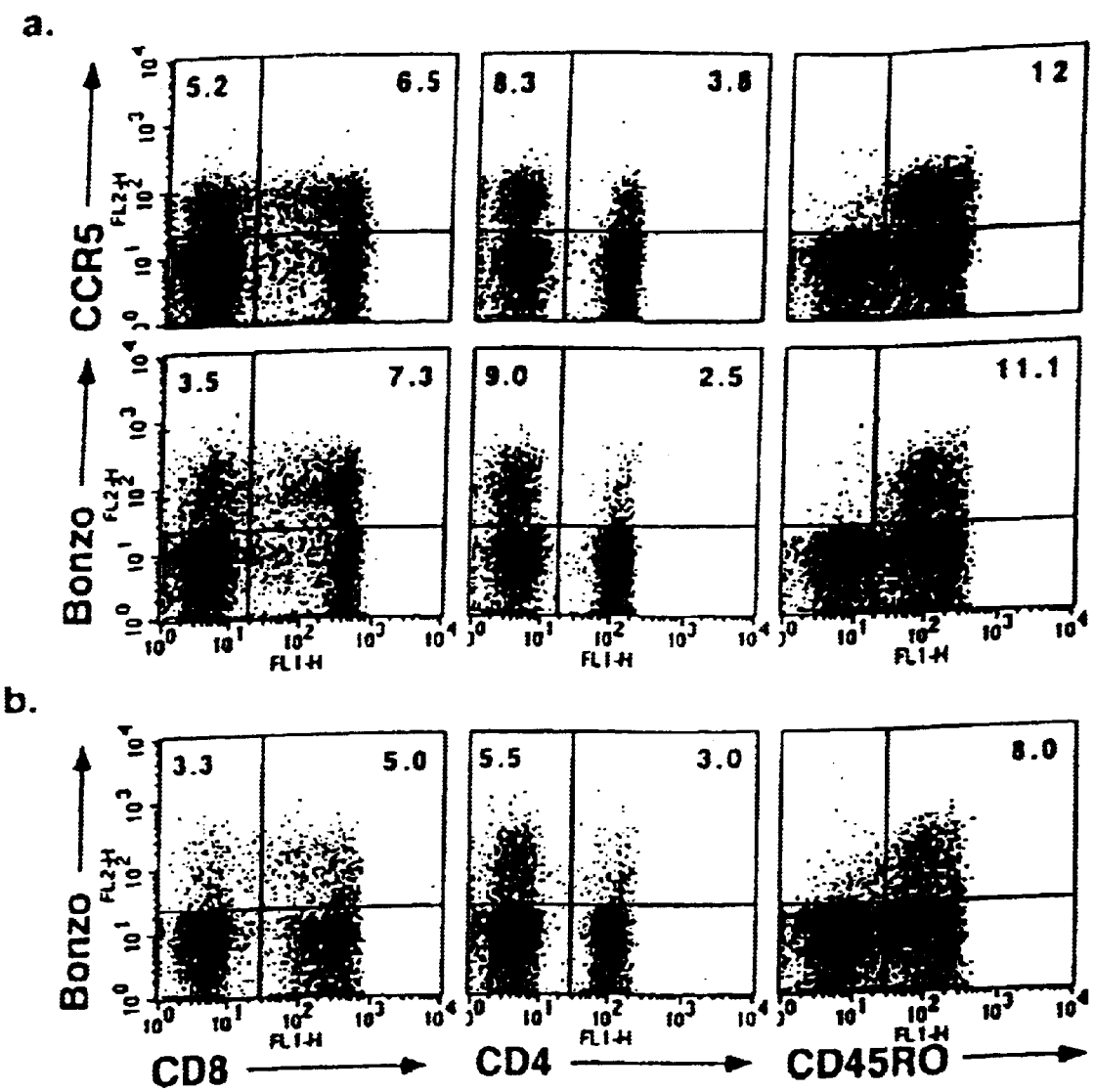
FIGS. 7a–7b shows that Bonzo and CCR5 are expressed on similar T cell subsets. PBMC were stained with mAbs against either Bonzo or CCR5, and then secondary PE-conjugated antibody followed by CD3-TC and FITC-conjugated anti-CD8, CD4 or CD45RO mAbs. Gating was restricted to CD3$^+$ cells.
Figure 8:
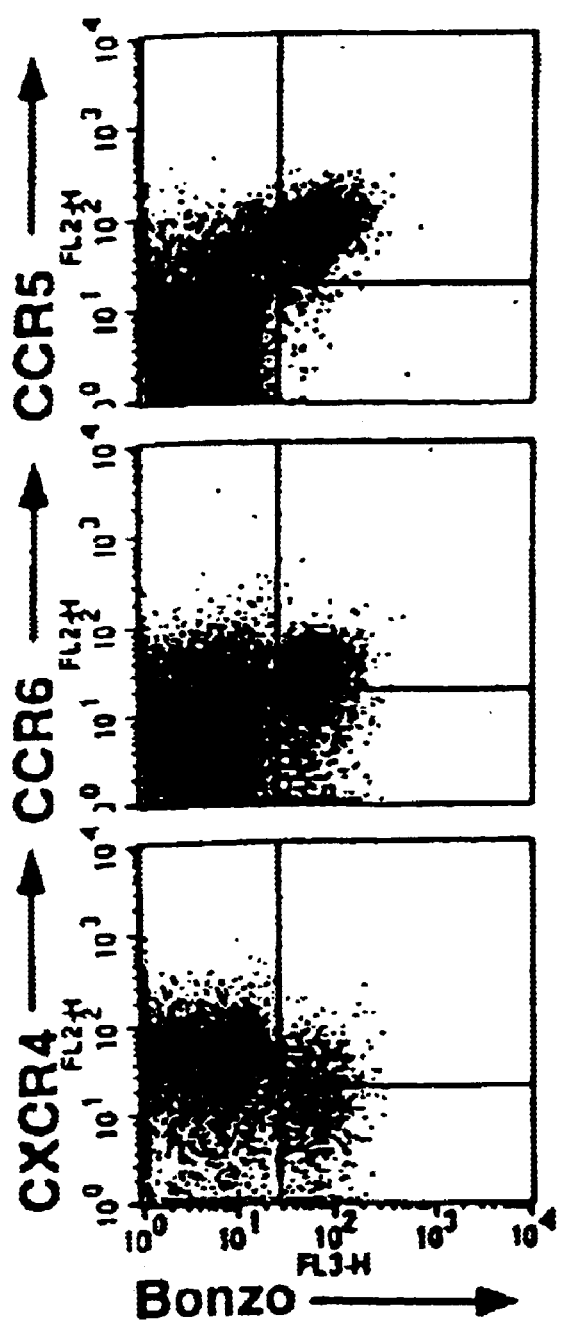
FIG. 8 shows the co-expression of Bonzo with CCR5. PBMC were stained with Bonzo as previously described, followed by either PE-conjugated anti-CCR5, CCR6 or CXCR4 and TC-conjugated anti-CD3 mAbs. Profiles are gated on CD3$^+$ cells.

It has been reported that expression of some chemokine receptors, such as the major HIV coreceptor CCR5, is also restricted to the memory subset of T cells [Liu et al., Cell 86:367 (1996)]. As shown in FIG. 7, the expression profile of CCR5 on resting T cells very closely parallels that of Bonzo. Indeed, co-staining of PBMC with antibodies specific for Bonzo and CCR5 showed that most Bonzo-positive cells were also CCR5$^+$(FIG. 8). PBMC from a healthy donor with a mutation in the CCR5 gene that prevents its cell surface expression [Loetscher et al., J Exp Med 184:569 (1996)] exhibited normal expression of Bonzo (FIG. 7b), demonstrating that absence of CCR5 from the cell surface does not negatively influence Bonzo expression. Most Bonzo-positive resting T cells also expressed CCR6 (FIG. 8), whereas expression of Bonzo and CXCR4 was inversely correlated (FIG. 8). This inverse expression pattern reflects lower levels of CXCR4 on memory T cells [Liu et al., Cell 86:367 (1996)], which preferentially express Bonzo (FIG. 6d).

The expression of Bonzo within the thymus and secondary lymphoid organs, adenoids and tonsils were also analyzed. Bonzo, CCR5 and CCR6 expression was either non-detectable or was present on less than 1% of thymocytes, whereas the majority of the thymocytes expressed CXCR4. Expression profiles of Bonzo, CCR5 and CCR6 on the lymphocytes isolated from tonsils or adenoids were similar to those observed on PBMC, although a greater proportion of T cells was positive and most of these cells expressed CD45RO$^+$ as well as the early activation marker CD69.

Regulation of Bonzo Expression by Cytokine Stimulation of Resting T Cells

Figure 9:
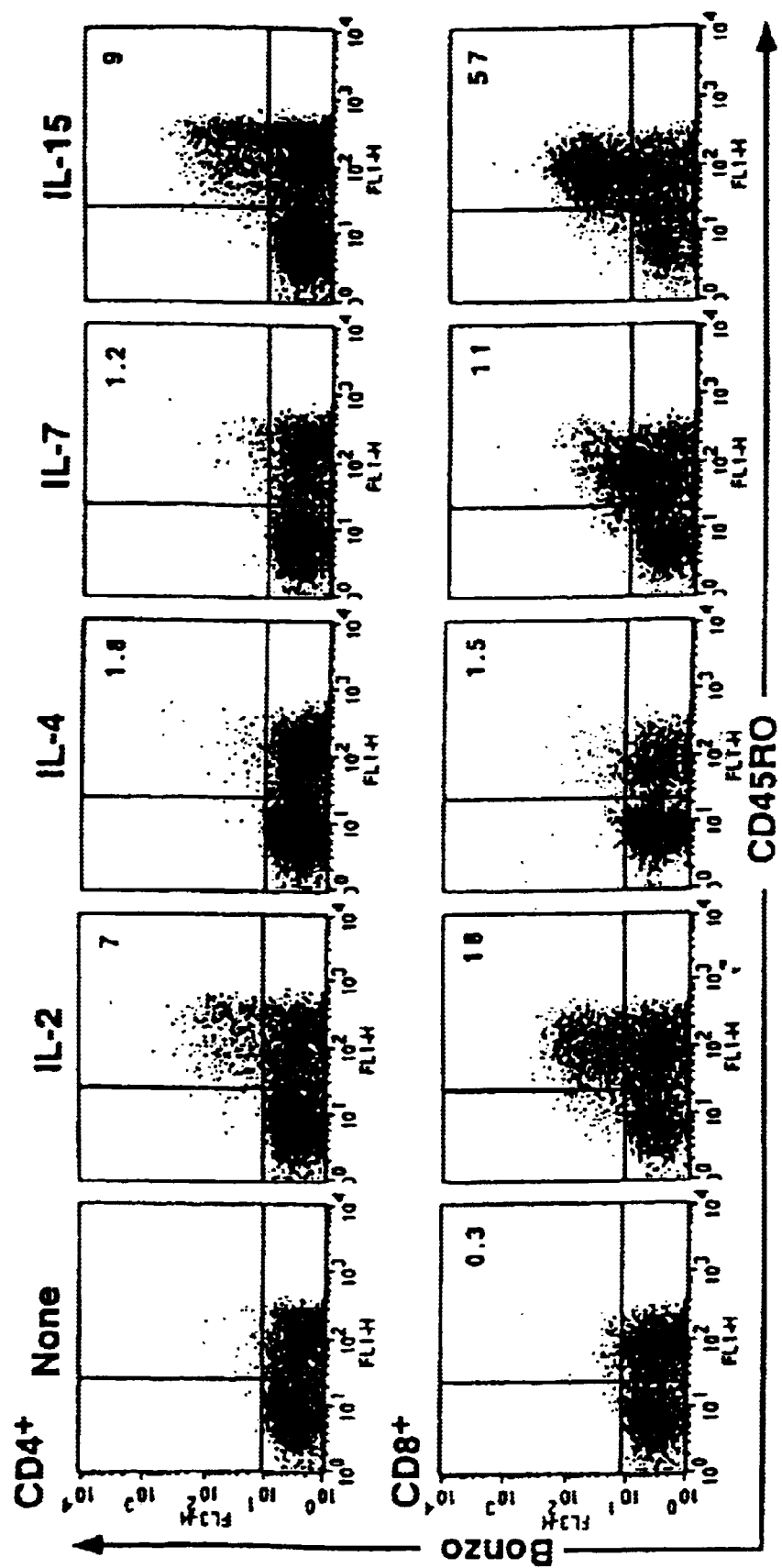
FIG. 9 shows cytokine mediated regulation of Bonzo and CCR5 on resting CD4$^+$ and CD8$^+$ T cells. Purified CD4$^+$ or CD8$^+$ resting T cells were cultured for 8 days in the presence of the cytokines IL-2 (200 U/ml), IL-4 (20 ng/ml), IL-7 (10 ng/ml), or IL-15 (10 ng/ml). Cells were then stained with mAbs specific for Bonzo and for CD45RO and CD4 or CD8 (top and lower panels, respectively).
Figure 10:
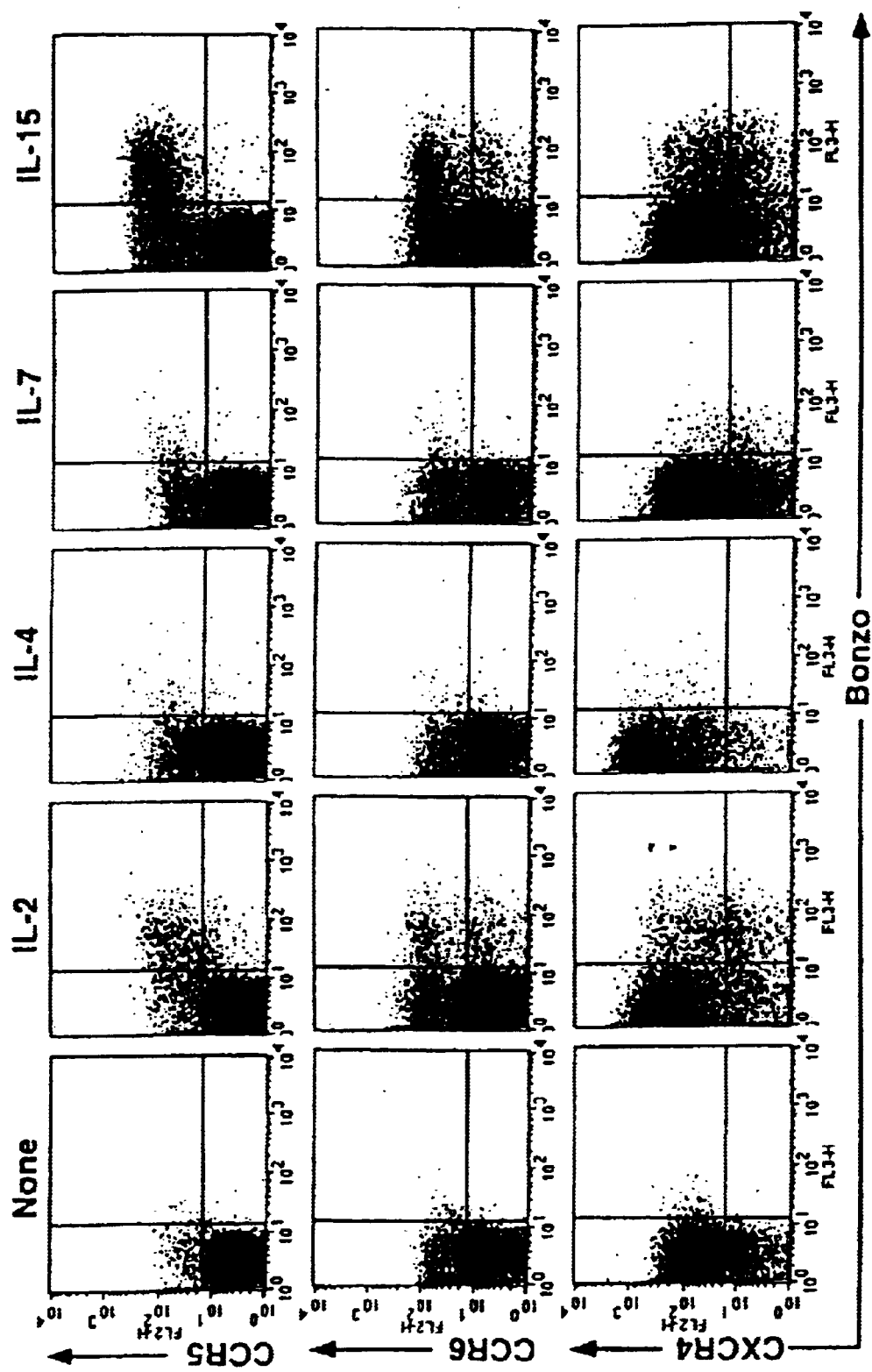
FIG. 10 shows cytokine mediated co-regulation of Bonzo and chemokine receptors CCR5, CCR6 or CXCR4 on resting T cells. Purified CD4$^+$ T cells were cultured with cytokines as described in FIG. 9. Cells were stained for Bonzo, CCR5, CCR6 or CXCR4 expression as in FIG. 8.

The concordant subset distribution of Bonzo and CCR5 suggested that the surface expression of these molecules may be regulated by similar mechanisms. It has been noted that IL-2 or IL-15 stimulation of human T cells can upregulate some of the CC chemokine receptors [Unutmaz et al., J Exp Med 189:1735 (1999), Perera et al., J Immutiol 162:2606 (1999), Jinquan et al., J Immunol 162:4285 (1999), Jourdan et al., J Immunol 160:4153 (1998)]. It was therefore queried whether Bonzo is similarly regulated by cytokines on resting human T cells. CD4$^+$ and CD8$^+$ resting T cells were purified from PBMC and cultured for 8 days in the presence of various cytokines. Culture of CD4$^+$ or CD8$^+$ T cells with IL-2 or L-15 resulted in upregulated expression of Bonzo exclusively on CD45RO$^+$ memory T cells (FIG. 9), with expression on CD8$^+$ T cells usually greater than on CD4$^+$ T cells. This result is consistent with the staining pattern observed on freshly isolated PBMC. Little expression was observed on CD4⁺ T cells cultured with IL-4 or IL-7 (FIG. 9) and none with IL-6, IL-12 or IFNγ. However, significant upregulation of Bonzo was observed on CD8⁺ T cells cultured with IL-7 (FIG. 9, lower panel). IL-2 and IL-15 also upregulated CCR5 and CCR6 expression on CD4⁺ T cells, and most Bonzo-expressing cells also co-expressed these CC chemokine receptors (FIG. 10). Similar results were obtained with CD8⁺ T cells. This result recapitulates the coordinate expression profile of Bonzo with CCR5 or CCR6 in freshly isolated PBMC (FIG. 8). Conversely, Bonzo positive cells had slightly lower CXCR4 expression as compared to Bonzo negative cells after stimulation with IL-2 or IL-15 (FIG. 10). CXCR4 expression was significantly upregulated in the presence of IL-4 and there was also a moderate increase in response to IL-2 or IL-15, in accordance with previous reports [Wang et al., *J Leukoc Biol* 64:642 (1998), Valentin et al., *Proc Natl Acad Sci USA* 95:8886 (1998), Gosling et al., *Proc Natl Acad Sci USA* 94:5061 (1997)].

Post-transcriptional Regulation of Bonzo Cell Surface Expression

Figures 2, 11A:
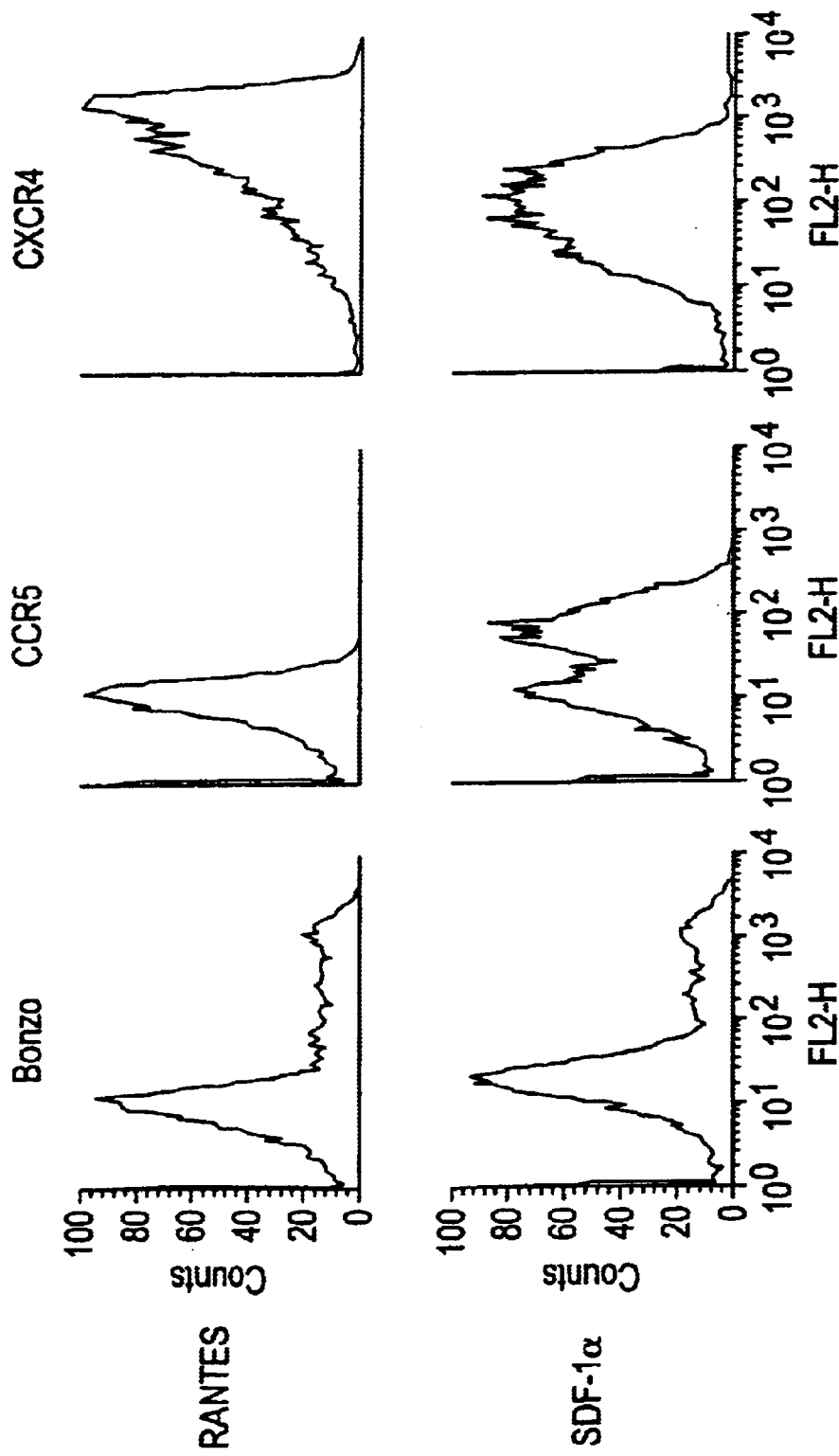

Most chemokine receptors contain a "DRY" sequence motif that appears to be required for coupling to G-proteins [Solari et al., *J Biol Chem* 272:9617 (1997)]. In contrast to other CC and CXC-family chemokine receptors, Bonzo possesses a non-canonical DRY box sequence at the second intracellular loop. This raised the possibility that, in response to its physiological ligand, Bonzo may not signal in a similar fashion to the other chemokine receptors. Recently, it has been reported that chemokine receptors are downregulated through ligand mediated endocytosis [Amara et al., *J Exp Med* 186:139 (1997), Alkhatib et al., *Virology* 234:340 (1997), Mack et al., *J Exp Med* 187:1215 (1998), Sallusto et al., *Immunol Today* 19:568 (1998)]. Therefore, it was reasoned that if any of the CCR5 ligands also bound to Bonzo, it may be possible to detect this through downregulation of Bonzo, in the absence of detectable signaling. FIG. 11a shows that none of the known CCR5 ligands (RANTES, MIP-1α, MIP-1β) had any effect on Bonzo expression, whereas they completely downmodulated CCR5 at the same concentrations. As expected, CXCR4 was downmodulated by its ligand SDF-1α, but not by CCR5 ligands (FIG. 11a). Interestingly, stimulation of cells with phorbol ester (PMA) also did not have any effect on Bonzo expression, although CCR5 and CXCR4 expression was completely downmodulated (FIG. 11b). Similarly, upon re-stimulation of T cell lines with mitogen, CCR5 expression was downmodulated, but that of Bonzo was unaffected (FIG. 11c). In order to determine whether Bonzo is premade and stored in intracellular compartments and released to the cell surface upon signaling, intracellular staining was performed on resting or cytokine-stimulated primary T cells with anti-Bonzo antibody. No difference was observed between cell surface staining alone or in conjunction with intracellular staining.

Targeted Disruption and Knock-in of EGFP into the Mouse Bonzo Gene Locus

Figure 12:
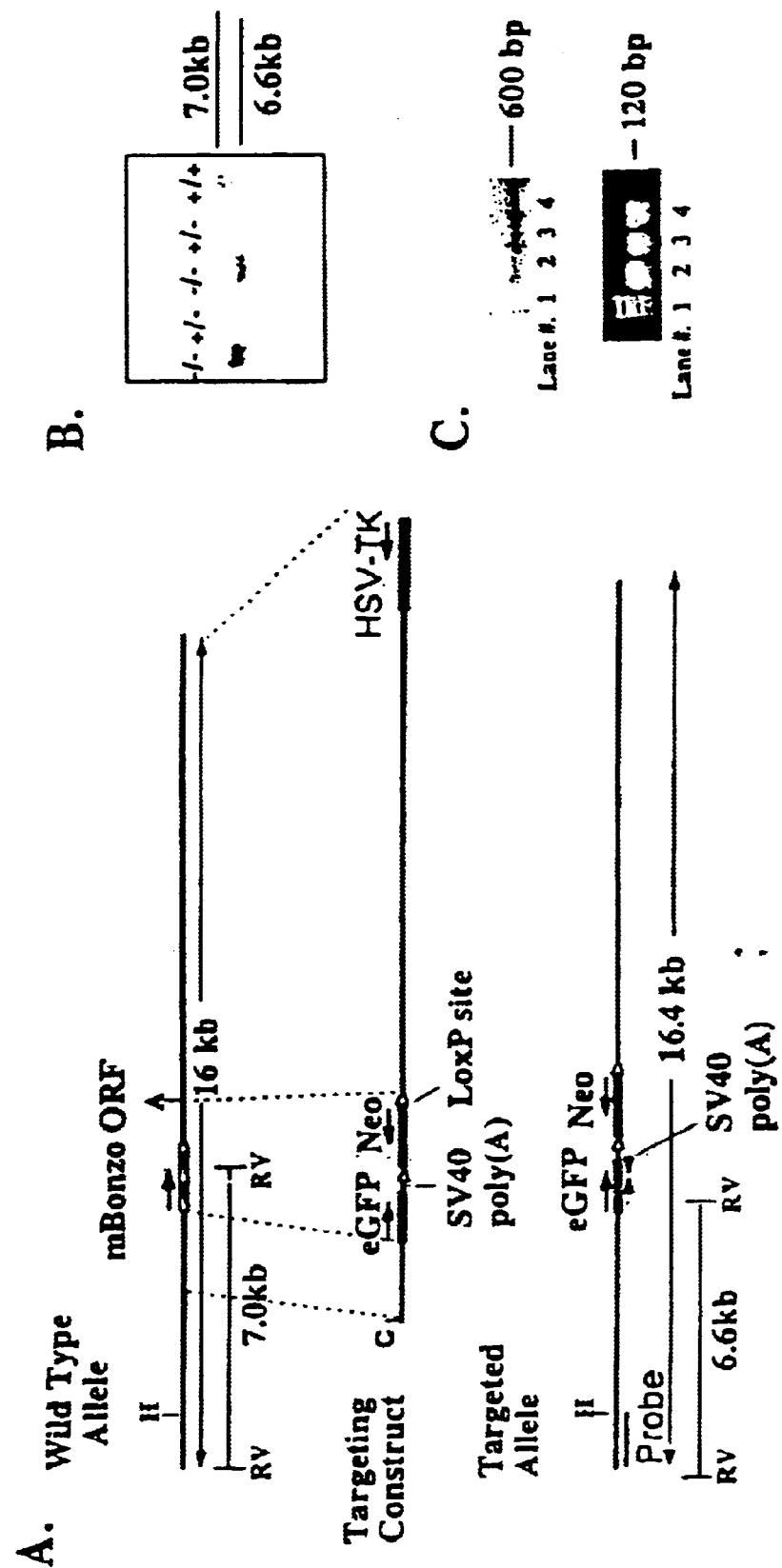
FIGS. 12a–12c depict the targeted knock-in of EGFP in the mouse Bonzo gene.

To gain insight into the expression pattern and function of Bonzo in mice, a gene targeting strategy was used that replaced the Bonzo coding sequence with that of EGFP (FIG. 12a). Germline transmission was obtained with two independent ES cell clones. Deletion of the Bonzo gene was verified by Southern blot analysis (FIG. 12b). In an RT-PCR assay, a 3' portion of Bonzo mRNA was amplified from total RNA derived from lymph node and spleen of both Bonzo⁺/⁻ (Bz⁺/⁻) and Bonzo⁻/⁻(Bz⁻/⁻) mice. No amplification was observed from Bz⁻/⁻ mice (FIG. 12c). Mating of heterozygous mice gave rise to Bz⁻/⁻ mice in Mendelian proportions.

Bz⁻/⁻ mice were phenotypically indistinguishable from Bz⁺/⁺ and Bz⁺/⁻ littermates in a specific pathogen-free environment. Histological analysis of organs displayed no morphological difference among the three genotypes. Flow-cytometric analysis of cells from lymphoid organs showed no alteration in various cell populations. Proliferation of T cells from Bz⁺/⁻ or Bz⁻/⁻ mice was assessed in response to different concentrations of anti-CD3 antibody, in the presence or absence of anti-CD28 antibody. No difference was observed between Bz⁻/⁺ and Bz⁻/⁻ cells. NP-KLH-immunized Bz⁺/⁻ and Bz⁻/⁻ mice also displayed similar levels of NP-specific IgM and IgG1 production, suggesting that T cell help and B cell function were normal in Bonzo-deficient mice.

Tracing Mouse Bonzo Expression in EGFP Knock-in Mice

The in-frame substitution of EGFP for Bonzo yields a sensitive tool to trace Bonzo expression and regulation in vivo. Histological analysis did not show any GFP expression in non-lymphoid tissues. Strong green fluorescence was detected in spleen and lymphoid nodes. In spleen, GFP positive cells were clustered in the periarteriolar lymphoid sheath (PALS) area in the white pulp, where T cells reside. Notably, there was no difference of expression pattern in Bz⁺/⁻ and Bz⁻/⁻ mice.

Figure 13:
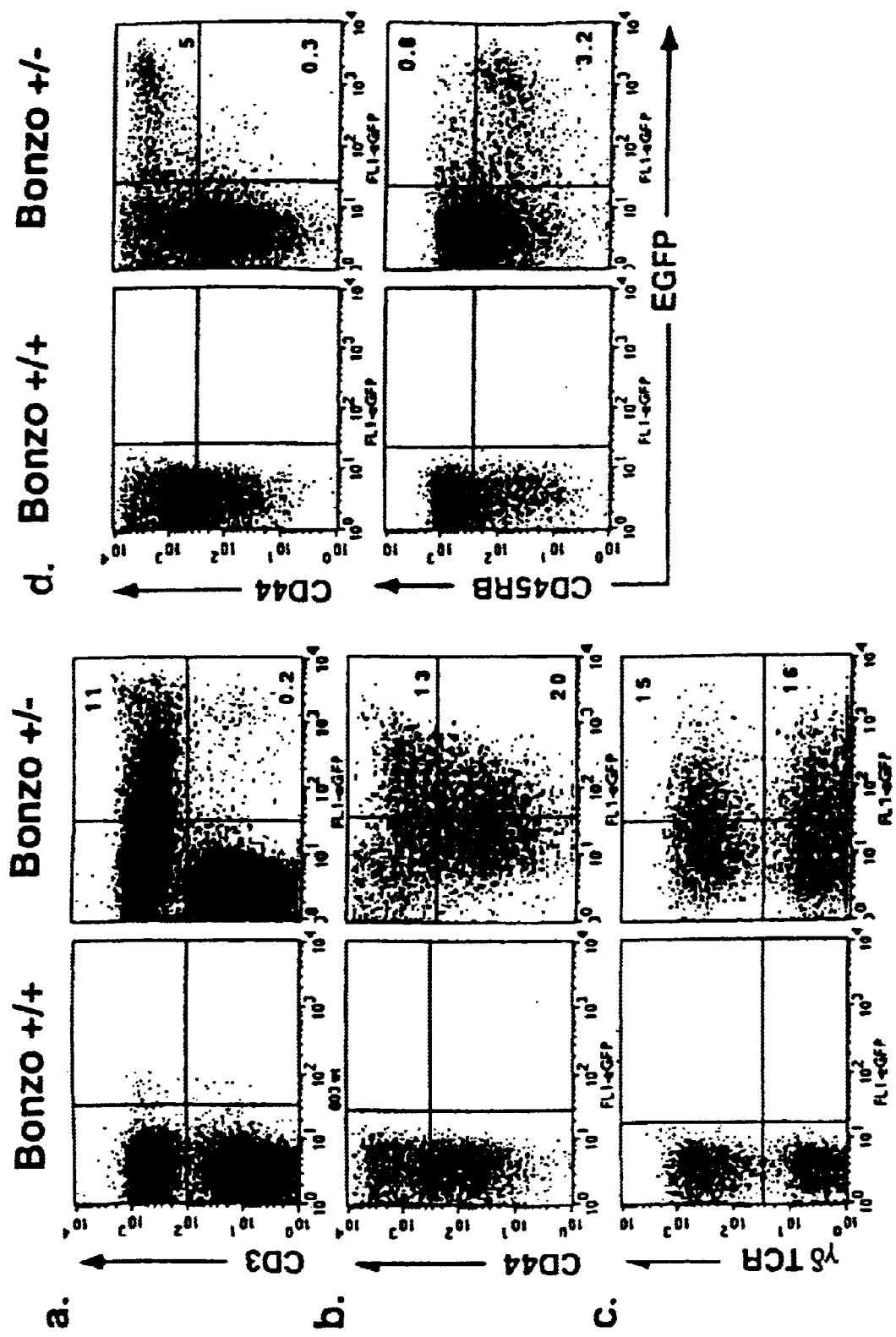
FIGS. 13a–13d show GFP expression on lymphocyte subsets from Bonzo knock-in mice. FACS analyses of T cell subsets from lymph nodes of Bonzo-GFP knock-in mice.

FACS analysis of GFP expression was next performed in different lymphoid subsets. GFP expression was undetectable in B cells, granulocytes, monocytes or macrophage, and dendritic cells. In thymus, no expression was observed in CD4⁺CD8⁺ cells or double negative thymocytes. Only a small subset of single positive cells showed strong expression. Within the lymph nodes and spleen almost all GFP⁺ cells were CD3⁺ T cells (FIG. 13a). The mean fluorescence of GFP expressing Bz⁻/⁻ cells was slightly higher than that in Bz⁺/⁻ cells, most likely due to GFP expression from both targeted alleles. Few CD4⁺ T cells expressed GFP, whereas the majority of CD8⁺ T cells were positive, with a broad distribution of intensity of GFP expression. The distribution of GFP expression was next analysed on naïve versus memory T cells in Bonzo knock-in mice. CD8⁺ cells were all CD44⁺ and it was difficult to discriminate naïve versus memory cells (FIG. 13b). γδ T cells from lymphoid organs or resident within the skin, reproductive tract, or gut also expressed GFP (FIG. 13c). Interestingly, GFP expression on CD4⁺ murine T cells was restricted to CD44⁺ and CD45RB$^{lo}$ subset (FIG. 13d), suggesting that, as in human CD4⁺ T cells, Bonzo is primarily expressed in the memory subset of mouse CD4⁺ T cells.

Figure 14:
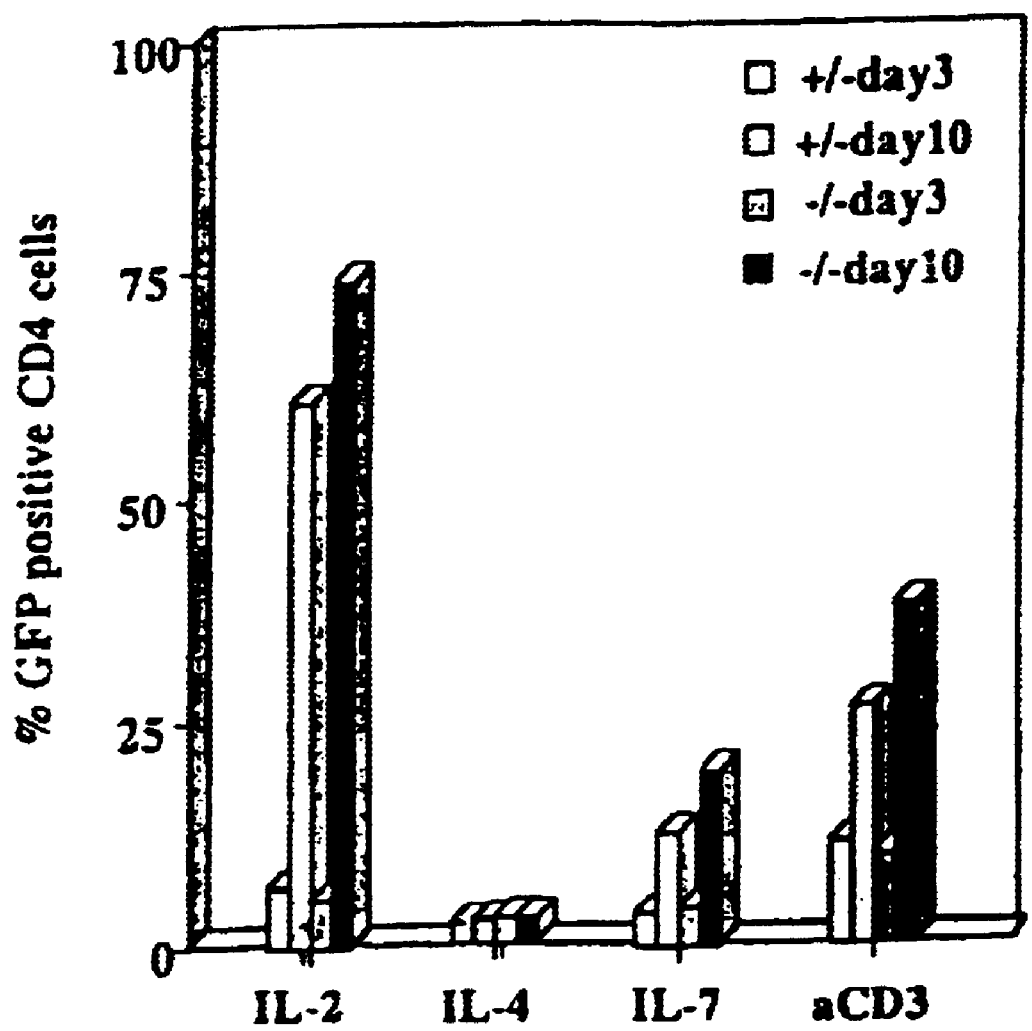
FIG. 14 shows the regulation of mBonzo expression by cytokines. CD4$^+$ T cells were purified from lymph nodes of Bz$^{+/-}$ and Bz$^{-/-}$ mice. $4 \times 10^5$ cells were treated with cytokines (IL-2, IL-7 and IL-4) or activated by plate-bound CD3 antibody and assayed for GFP expression three and ten days later. Most GFP-expressing cells were CD44$^{hi}$. The result is plotted as percentage of CD4$^+$ T cells that are GFP positive.

Finally it was determined whether, similar to human Bouzo, expression of mBouzo can also be modulated by the presence of cytokines. Indeed, dramatic upregulation of GFP expression was observed after 10 days of culture with IL-2, but less with IL-7 and none with IL-4. These results suggest that cytokine-mediated regulation of murine Bonzo fellow the pattern of its human counterpart (FIG. 14).

Discussion

To address the in vivo distribution of Bonzo-expressing cells and the modulation of this expression, a monoclonal antibody was used that is specific for Bonzo to demonstrate that expression of this receptor is highly restricted to the memory subset of resting human T cells. It has been further shown that, similar to CCR5, Bonzo expression is upregulated by the cytokines IL-2 and IL-15. However, in contrast to CCR5, upon PMA treatment or TCR stimulation Bonzo was not down-modulated. A similar expression pattern was observed on mouse CD4+ T cells of mice in which a green fluorescent protein (GFP) gene was knocked into the endogenous Bonzo locus.

The discovery that HIV and SIV utilize chemokine receptors to enter into target cells raised hopes that chemokines and chemokine receptors might hold clues to understanding the progression of HIV-mediated pathogenesis. These discoveries also bolstered the general interest in the regulation of lymphocyte migration by chemokine receptors. The recent development of antibodies to chemokine receptors has revealed the complex subset specific expression of these receptors on T lymphocytes [Oin et al., *Eur J Immunol* 26:640 (1996)]. In this report, it is demonstrated that the expression pattern and regulation of the SIV/HIV coreceptor and putative orphan chemokine-receptor Bonzo strongly parallels those of CC family chemokine receptors. It has been shown that CC family chemokine receptors, CCR2, CCR5 and CCR6 are expressed primarily on the CD45RO+ or CD26+ memory subset of T cells [Liu et al., *Cell* 86:367 (1996), Rabin et al., *J. Immunol* 162:3840 (1999), Liao et al., *J Immunol* 162:186 (1999), Huang et al., *Nat Med* 2:1240 (1996)]. The expression pattern of Bonzo, similarly, was restricted to memory T cells. In this regard, it was found that most Bonzo positive cells also co-expressed CCR5 or CCR6 on peripheral blood T cells. In contrast, Bonzo was not co-expressed with high levels of CXCR4, reflecting lower CXCR4 expression on memory versus naive T cells [Liu et al., *Cell* 86:367 (1996)]. Although Bonzo was expressed on CD4+, CD8+ and γδ subsets of T cells, expression levels were usually higher on CD8+ and TCR γδ+ T cells. Few NK cells were found to express Bonzo, and those that did had relatively low levels of CD16 expression (FIG. 6e), possibly representing recently activated NK cells.

The co-expression of Bonzo and CCR5 on memory T cells is notable from the perspective of HIV coreceptor usage, since CCR5 is the major receptor used by most strains of HIV and almost all SIVs. Expression of CCR5 on the cell surface has been shown to be critical in transmission of HIV-1 infection since a homozygous 32-base pair deletion in the CCR5 gene prevents CCR5 expression and confers resistance against HIV-1 infection [Loetscher et al., *J Exp Med* 184:569 (1996), Dean et al., *Science* 273:1856 (1996), Unutmaz et al., *Proc Natl Acad Sci USA*, 94:1615 (1997)]. As shown herein T cells isolated from individuals who are homozygous for the CCR5 Δ32 mutation expressed normal levels of Bonzo. Although Bonzo is a minor HIV-1 coreceptor, its role during transmission of infection and pathogenesis is unclear. However, Bonzo is a major SIV receptor and is also used by many HIV-2 strains in vitro [Unutmaz et al., *Semin Immunol* 10:225 (1998), Deng et al., *Nature* 388:296 (1997)]. It is interesting to note that different species of non-human primates vary widely in their responses to SIV infection and people infected with HIV-2 usually have a more delayed progression to AIDS. It is possible that Bonzo may substitute for CCR5 usage during infection with SIV and HIV-2 isolates and perhaps influences the course of infection and pathogenesis. In contrast to CCR5, Bonzo was not expressed by macrophages or dendritic cells. This expression pattern may preclude its involvement during the initial phase of infection, where macrophage or dendritic cell infection is thought to be necessary for the virus to get a foothold in the body [Baba et al., *J Biol Chem* 272:14893 (1997)].

Cytokine stimulation of T cells differentially regulates the surface expression of chemokine receptors. IL-2 has been described to potently upregulate CCR1, CCR2, CCR5, CCR6, and CXCR3 [Unutmaz et al., *J Exp Med* 189:1735 (1999), Liu et al., *Cell* 86:367 (1996), Perera et al., *J Immunol* 162:2606 (1999), Loetscher et al., *Eur J Immunol* 28:3696 (1998), Signoret et al., *J Cell Biol* 139:651 (1997)]. More recently IL-15 has also been shown to have similar effects on some of the CC chemokine receptors [Unutmaz et al., *J Exp Med* 189:1735 (1999), Jinquan et al., *J Immunol* 162:4285 (1999)]. CXCR4 expression, on the other hand, is dramatically upregulated in the presence of IL-4 [Wang et al., *J Leukoc Biol* 64:642 (1998), Valentin et al., *Proc Natl Acad Sci USA* 95:8886 (1998), Gosling et al., *Proc Natl Acad Sci USA* 94:5061 (1997)]. As shown herein Bonzo, similar to CC chemokine receptors, is induced through stimulation of highly purified resting T cells with IL-2 or IL-15 and is co-expressed with CCR5 or CCR6. The coordinated regulation of Bonzo and CCR5 on resting T cells by IL-2 or IL-15 recapitulates the ex vivo expression pattern.

Notably, the gene for Bonzo maps to chromosome 3 where most of the chemokine receptors, especially of the CC family, are localized [Loetscher et al., *Curr Biol* 7:652 (1997)]. Additionally, the amino acid sequence of Bonzo is similar to that of other members of the chemokine receptor family. Taken together with the results on its expression pattern and those of cytokine-mediated regulation, these findings suggest that Bonzo is also a chemokine receptor. However, Bonzo stands apart from other chemokine receptors because its expression is resistant to PMA-induced downmodulation. This result contrasts with PMA-induced downmodulation of CXCR4 [Signoret et al., *J Cell Sci* 111:2819 (1998), Sallusto et al., *Nature* 401:708 (1999)], CCR5 (FIG. 11b) or CCR6. However, Bonzo may still be downmodulated by its ligand(s), since the mechanisms of ligand- and PMA-induced downmodulation appear to be different [Sallusto et al., *Immunol Today* 19:568 (1998), Signoret et al., *J Cell Sci* 111:2819 (1998), Sallusto et al., *Nature* 401:708 (1999)]. No ligand-induced downmodulation of Bonzo was detected in the presence of CCR5 ligands, but it could not be ruled out that Bonzo is resistant to ligand-induced endocytosis and thus may still be able to bind to these chemokines.

Since there is no antibody yet available against mouse Bonzo, the targeted knock-in of GFP was used in place of the Bonzo gene as an indicator of Bonzo expression. It was found that murine Bonzo is expressed in cell subsets similar to human Bonzo, namely in T cells, particularly those displaying markers of effector/memory cells and those stimulated by IL-2. However, both in mouse and human only a subset of memory cells expressed Bonzo, similar to CCR5 expression. Chemokines regulate both the inter and intra-organ migration patterns of human T cell subsets. Recently, human memory T cells were subdivided, into two functionally distinct subsets based on CCR7 expression [Kurihara et al., *J Exp Med* 186:1757 (1997)]. CCR7− memory cells express receptors for migration to inflamed tissues and display immediate effector function. In contrast, CCR7+ memory cells express lymph-node homing receptors and lack immediate effector function. Interestingly, the CCR7− cells were enriched for expression of CCR5, CCR6 and CCR1 [Kurihara et al., *J Exp Med* 186:1757 (1997)]. Based on the similar expression patterns, the majority of Bonzo+ T cells appear to be compartmentalized to the CCR7− memory subset, indicating a role for Bonzo in recruiting memory T cells to sites of inflammation.

No functional defect has been detected in homozygous Bonzo knockout mice. This may be due to redundancy in the chemokine receptor system. However, it will be important to perform more detailed analyses of migration patterns of T cells in response to a wide variety of pathogens, and, in particular, to study T cell memory responses to the pathogens. Mutations in other chemokine receptor family members, such as CCR5 and CCR2 resulted in phenotypes revealed only after studies in responses to pathogen or in disease models [Zhou et al., *J Immunol* 160:4018 (1998), Huffnagle et al., *J Immunol* 163:4642 (1999), Traynor et al., *J Immunol* 164:2021 (2000)]. It will also be interesting to establish multiple knockouts between the Bonzo mutant mice and mutants for other chemokine receptors expressed in memory T cells, to identify potentially overlapping functions of these molecules.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are all incorporated by references in their entireties.

What is claimed is:

1. A method of identifying an agent that can enhance the immune response to a specific pathogen or against a specific vaccine comprising:
   (a) contacting an agent with a cell; wherein the cell encodes Bonzo/STRL33; and
   (b) determining the amount of Bonzo/STRL33 expressed by a cell in the presence of the agent; wherein the agent is identified as an agent that can enhance the immune response to a specific pathogen or against a specific vaccine when the amount of expression of Bonzo/STRL33 increases in the presence of the agent relative to in its absence.

2. The method of claim 1 wherein said determining is performed with an antibody raised against Bonzo/STRL33.

3. The method of claim 1 wherein said determining is performed by PCR.

4. An agent obtained by the method of claim 1.

5. A method of enhancing the immune response for a specific pathogen or to enhance the effect of a specific vaccine comprising administering the agent of claim 4 to an animal subject.

6. A method of identifying an agent that can enhance the immune response to a specific pathogen or against a specific vaccine comprising:
  (a) contacting an agent with a cell; wherein the cell normally encodes Bonzo/STRL33 but the coding sequence for Bonzo/STRL33 has been replaced by a coding sequence for a reporter gene; and
  (b) determining the amount of reporter gene expressed by a cell in the presence of the agent; wherein the agent is identified as an agent that can enhance the immune response to a specific pathogen or against a specific vaccine when the amount of expression of the reporter gene increases in the presence of the agent relative to in its absence.

7. The method of claim 6 wherein the coding sequence for the reporter gene encodes green fluorescent protein.

8. The method of claim 6 wherein the coding sequence for the reporter gene encodes luciferase.

9. An agent obtained by the method of claim 6.

10. A method of enhancing the immune response for a specific pathogen or to enhance the effect of a specific vaccine comprising administering the agent of claim 9 to an animal subject.

11. A method of identifying an agent that can inhibit the recruitment of memory cells comprising:
  (a) contacting an agent with a cell; wherein the cell encodes Bonzo/STRL33; and
  (b) determining the amount of Bonzo/STRL33 expressed by a cell in the presence of the agent; wherein the agent is identified as an agent that can inhibit the recruitment of memory cells when the amount of expression of Bonzo/STRL33 decreases in the presence of the agent relative to in its absence.

12. The method of claim 11 wherein said determining is performed with an antibody raised against Bonzo/STRL33.

13. The method of claim 11 wherein said determining is performed by PCR.

14. An agent obtained by the method of claim 11.

15. A method of treating inflammation comprising administering to an animal subject in need of such treatment an agent that causes a decrease in Bonzo/STRL 33 expression and/or function.

* * * * *

```
                        SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
        (A) LENGTH: 1026 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
         (A) ORGANISM: Homo sapiens (xi) SEQUENCE DESCRIPTION: SEQ ID NO: 1:

ATGGCAGAGC ATGATTACCA TGAAGACTAT GGGTTCAGCA GTTTCAATGA CAGCAGCCAG60

GAGGAGCATC AAGACTTCCT GCAGTTCAGC AAGGTCTTTC TGCCCTGCAT GTACCTGGT120

GTGTTTGTCT GTGGTCTGGT GGGGAACTCT CTGGTGTGGT CATATCCATC TTCTACCAT180

AGTTGCAGAG CCTGACGGAT GTGTTCCTGT GAACCTACCC CTGGCTGACC TGGTGTTTG240

CTGCACTCTG CCCTTCTGGG CCTATGCAGG CATCCATGAA TGGGTGTTTG GCCAGGTCA300

GTGCAAGAGC CTACGGGCAT CTACACTATT AACTTCTACA CGTCCATGCT CATCCTCAC360

TGCATCACTG TGGATCGTTT CATTGTAGTG GTTAAGGCCA CCAAGGCCTA CAACCAGCA420

GCCAAGAGGA TGACCTGGGG CAAGGTCACC AGCTTGCTCA TCTGGGTGAT ATCCCTGCT480

GTTTCCTTGC CCCAAATTAT CTATGGCAAT GTCTTTAATC TCGACAAGCT CATATGTGG540

TACCATGACG AGGCAATTTC CACTGTGGTT CTTGCCACCC AGATGACACT GGGGTTCTT600

TTGCCACTGC TCACCATGAT TGTCTGCTAT TCAGTCATAA TCAAAACACT GCTTCATGC660

GGAGGCTTCC AGAAGCACAG ATCTCTAAAG ATCATCTTCC TGGTGATGGC TGTGTTCCT720

CTGACCCAGA TGCCCTTCAA CCTCATGAAG TTCATCCGCA GCACACACTG GGAATACTA780

GCCATGACCA GCTTTCACTA CACCATCATG GTGACAGAGG CCATCGCATA CCTGAGGGC840

TGCCTTAACC CTGTGCTCTA TGCCTTTGTC AGCCTGAAGT TTCGAAAGAA CTTCTGGAA900

CTTGTGAAGG ACATTGGTTG CCTCCCTTAC CTTGGGGTCT CACATCAATG GAAATCTTC960

GAGGACAATT CCAAGACTTT TTCTGCCTCC CACAATGTGG AGGCCACCAG CATGTTCC1020

TTATAG                                                      1026
```

(2) INFORMATION FOR SEQ ID NO: 2:

(i) SEQUENCE CHARACTERISTICS:
        (A) LENGTH: 342 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO: 2:

```
Met Ala Glu His Asp Tyr His Glu Asp Tyr Gly Phe Ser Ser Phe As
  1               5                  10                  15

Asp Ser Ser Gln Glu Glu His Gln Asp Phe Leu Gln Phe Ser Lys Va
             20                  25                  30

Phe Leu Pro Cys Met Tyr Leu Val Val Phe Val Cys Gly Leu Val Gl
             35                  40                  45

Asn Ser Leu Val Leu Val Ile Ser Ile Phe Tyr His Lys Leu Gln Se
         50                  55                  60

Leu Thr Asp Val Phe Leu Val Asn Leu Pro Leu Ala Asp Leu Val Ph
 65                  70                  75                  80

Val Cys Thr Leu Pro Phe Trp Ala Tyr Ala Gly Ile His Glu Trp Va
                 85                  90                  95

Phe Gly Gln Val Met Cys Lys Ser Leu Leu Gly Ile Tyr Thr Ile As
                100                 105                 110

Phe Tyr Thr Ser Met Leu Ile Leu Thr Cys Ile Thr Val Asp Arg Ph
             115                 120                 125

Ile Val Val Val Lys Ala Thr Lys Ala Tyr Asn Gln Gln Ala Lys Ar
         130                 135                 140

Met Thr Trp Gly Lys Val Thr Ser Leu Leu Ile Trp Val Ile Ser Le
145                 150                 155                 160

Leu Val Ser Leu Pro Gln Ile Ile Tyr Gly Asn Val Phe Asn Leu As
                165                 170                 175

Lys Leu Ile Cys Gly Tyr His Asp Glu Ala Ile Ser Thr Val Val Le
             180                 185                 190

Ala Thr Gln Met Thr Leu Gly Phe Phe Leu Pro Leu Leu Thr Met Il
         195                 200                 205

Val Cys Tyr Ser Val Ile Ile Lys Thr Leu Leu His Ala Gly Gly Ph
         210                 215                 220

Gln Lys His Arg Ser Leu Lys Ile Ile Phe Leu Val Met Ala Val Ph
225                 230                 235                 240

Leu Leu Thr Gln Met Pro Phe Asn Leu Met Lys Phe Ile Arg Ser Th
                245                 250                 255

His Trp Glu Tyr Tyr Ala Met Thr Ser Phe His Tyr Thr Ile Met Va
             260                 265                 270

Thr Glu Ala Ile Ala Tyr Leu Arg Ala Cys Leu Asn Pro Val Leu Ty
             275                 280                 285

Ala Phe Val Ser Leu Lys Phe Arg Lys Asn Phe Trp Lys Leu Val Ly
             290                 295                 300

Asp Ile Gly Cys Leu Pro Tyr Leu Gly Val Ser His Gln Trp Lys Se
305                 310                 315                 320

Ser Glu Asp Asn Ser Lys Thr Phe Ser Ala Ser His Asn Val Glu Al
```

```
                      325                 330                 335
            Thr Ser Met Phe Gln Leu
                              340
```

(2) INFORMATION FOR SEQ ID NO: 3:

(i) SEQUENCE CHARACTERISTICS:
       (A) LENGTH: 1037 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (vi) ORIGINAL SOURCE:
      (A) ORGANISM: African Green Monkey (xi) SEQUENCE DESCRIPTION: SEQ ID NO: 3:

```
ATGGCAGAGT ATGATCACTA TGAAGATAAT GGCTTCAACA GTTTCAATGA CAGCAGCCAG 60

GAGGAGCATC AGGACTTCCT GCAGTTCAGC AAGGTCTTTC TGCCCTGCAT GTATCTGGT 120

GTGTTTGTCT GTGGCCTGGT GGGGAACTCC CTGGTGCTGG TCATATCCAT CTTCTACCA 180

AAGCTACAGA GCCTGACGGA CGTGTTCCTG GTGAACCTAC CCCTGGCTGA CCTGGTGTT 240

GTCTGCACTC TGCCCTTCTG GGCCTATGCA GGCATCCATG AATGGATCTT TGGCCAGGT 300

ATGTGCAAGA CCCTACTGGG TATCTACACT ATTAACTTCT ACACATCTAT GCTCATCCT 360

ACCTGCATCA CTGTGGATCG TTTCATTGTA GTGGTTAAGG CCACCAAGGC CTATAACCA 420

CAAGCCAAGA AGATGACTTG GGCAAGGTC ATCTGCTTGC TCATCTGGGT GATATCCCT 480

CTGGTTTCCT TGCCCCAAAT TATCTATGGC AATGTCTTTA ATCTGGACAA GCTCATATG 540

GGTTATCATG ATGAGGAGAT TTCCACTGTG GTTCTTGCCA CCCAGATGAC ACTGGGGTT 600

TTCTTGCCAC TGCTCGCCAT GATTGTCTGC TATTCAGTCA TAATCAAAAC ACTGCTTCA 660

GCTGGAGGCT TCCAGAAGCA CAGATCTCTA AAGATCATCT TCCTTGTGAT GGCTGTGTT 720

CTGCTGACCC AGACACCCTT CAACCTCGTG AAGCTCATCC GCAGCACACA CTGGGAGTA 780

TATGCCATGA CCAGCTTTCA CTACACCATC ATAGTGACAG AGGCCATCGC ATACCTGAG 840

GCCTGCCTTA ACCCTGTGCT CTATGCCTTT GTCAGCCTGA AGTTTCGAAA GAACTTCTG 900

AAACTTGTGA AGGACATTGG CTGTCTCCCT TACCTTGGGG TCTCACATCA ATGGAAATC 960

TCTGAGGACA ATTCCAAGAC TTTTTCTGCC TCCCACAATG TGGAGGCCAC CAGCATGT 1020

CAGTTATAGG CCTTGCC                                             1037
```

(2) INFORMATION FOR SEQ ID NO: 4:

(i) SEQUENCE CHARACTERISTICS:
      (A) LENGTH: 342 amino acids
      (B) TYPE: amino acid
      (C) STRANDEDNESS: single
      (D) TOPOLOGY: linear (ii) MOLECULE TYPE: protein (iii) HYPOTHETICAL: NO (vi) ORIGINAL SOURCE:
      (A) ORGANISM: African Green Monkey (xi) SEQUENCE DESCRIPTION: SEQ ID NO: 4:

```
        Met Ala Glu Tyr Asp His Tyr Glu Asp Asn Gly Phe Asn Ser Phe As
          1               5                  10                  15
```

```
            Asp Ser Ser Gln Glu His Gln Asp Phe Leu Gln Phe Ser Lys Va
                         20                  25                  30

Phe Leu Pro Cys Met Tyr Leu Val Val Phe Val Cys Gly Leu Val Gl
                     35                  40                  45

Asn Ser Leu Val Leu Val Ile Ser Ile Phe Tyr His Lys Leu Gln Se
                 50                  55                  60

Leu Thr Asp Val Phe Leu Val Asn Leu Pro Leu Ala Asp Leu Val Ph
             65                  70                  75                  80

Val Cys Thr Leu Pro Phe Trp Ala Tyr Ala Gly Ile His Glu Trp Il
                             85                  90                  95

Phe Gly Gln Val Met Cys Lys Thr Leu Leu Gly Ile Tyr Thr Ile As
                        100                 105                 110

Phe Tyr Thr Ser Met Leu Ile Leu Thr Cys Ile Thr Val Asp Arg Ph
                    115                 120                 125

Ile Val Val Val Lys Ala Thr Lys Ala Tyr Asn Gln Gln Ala Lys Ly
                130                 135                 140

Met Thr Trp Gly Lys Val Ile Cys Leu Leu Ile Trp Val Ile Ser Le
            145                 150                 155                 160

Leu Val Ser Leu Pro Gln Ile Ile Tyr Gly Asn Val Phe Asn Leu As
                            165                 170                 175

Lys Leu Ile Cys Gly Tyr His Asp Glu Glu Ile Ser Thr Val Val Le
                        180                 185                 190

Ala Thr Gln Met Thr Leu Gly Phe Phe Leu Pro Leu Leu Ala Met Il
                    195                 200                 205

Val Cys Tyr Ser Val Ile Ile Lys Thr Leu Leu His Ala Gly Gly Ph
                210                 215                 220

Gln Lys His Arg Ser Leu Lys Ile Ile Phe Leu Val Met Ala Val Ph
            225                 230                 235                 240

Leu Leu Thr Gln Thr Pro Phe Asn Leu Val Lys Leu Ile Arg Ser Th
                            245                 250                 255

His Trp Glu Tyr Tyr Ala Met Thr Ser Phe His Tyr Thr Ile Ile Va
                        260                 265                 270

Thr Glu Ala Ile Ala Tyr Leu Arg Ala Cys Leu Asn Pro Val Leu Ty
                    275                 280                 285

Ala Phe Val Ser Leu Lys Phe Arg Lys Asn Phe Trp Lys Leu Val Ly
                290                 295                 300

Asp Ile Gly Cys Leu Pro Tyr Leu Gly Val Ser His Gln Trp Lys Se
            305                 310                 315                 320

Ser Glu Asp Asn Ser Lys Thr Phe Ser Ala Ser His Asn Val Glu Al
                            325                 330                 335

Thr Ser Met Phe Gln Leu
                        340

(2) INFORMATION FOR SEQ ID NO: 5:

(i) SEQUENCE CHARACTERISTICS:
        (A) LENGTH: 1029 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: pigtail macaque
```

(xi) SEQUENCE DESCRIPTION: SEQ ID NO: 5:

```
ATGGCAGAGC ATGATTACCA TGAAGACTAT GGGCTCAACA GTTTCAATGA CAGCAGCCAG 60
GAGGAGCATC AAGACTTCCT GCAGTTCAGG AAGGTCTTTC TGCCCTGCAT GTACCTGGT 120
GTGTTTGTCT GTGGCCTGGT GGGGAACTCC CTGGTGCTGG TCATATCCAT CTTCTACCA 180
AAGCTGCAGA GCCTGACGGA CGTGTTCCTG GTGAACCTAC CCCTGGCTGA CCTGGTGTT 240
GTCTGCACTC TGCCCTTCTG GGCCTATGCA GGCATCCATG AATGGATCTT TGGCCAGGT 300
ATGTGCAAGA CCCTACTGGG CGTCTACACT ATTAACTTCT ACACATCCAT GCTCATCCT 360
ACCTGCATCA CTGTGGATCG TTTTCATTGTA GTGGTTAAGG CCACCAAGGC CTACAACCA 420
CAAGCCAAGA GGATGACTTG GGCAAGGTC ATCTGCTTGC TCATCTGGGT GATATCCCT 480
CTGGTTTCCT TGCCCCAAAT TATCTATGGC AATGTCTTTA ATCTGGACAA GCTCATATG 540
GGTTATCATG ACAAGGAGAT TTCCACTGTG GTTCTTGCCA CCCAGATGAC ACTGGGGTT 600
TTCTTGCCAC TGCTCGCCAT GATTGTCTGC TATTCAGTCA TAATCAAAAC ACTGCTTCA 660
GCTGGAGGCT TCCAGAAGCA CAGATCTCTA AAGATCATCT TCCTTGTGAT GGCTGTGTT 720
CTGCTGACCC AGACACCCTT CAACCTCGTG AAGCTCATCC GCAGCACACA CTGGGAGTA 780
TATGCCATGA CCAGCTTTCA CTACACCATC ATAGTGACAG AGGCCATCGC ATACCTGAG 840
GCCTGCCTTA ACCCTGTGCT CTATGCCTTT GTCAGCCTGA AGTTTCGAAA GAACTTCTG 900
AAACTTGTGA AGGACATTGG CTGTCTCCCT TACCTTGGGG TCTCACATCA ATGGAAATC 960
TCTGAGGACA ATTCCAAGAC TTTTTCTGCC TCCCACAATG TGGAGGCCAC CAGCATGT 1020
CAGTTATAG                                                        1029
```

(2) INFORMATION FOR SEQ ID NO: 6:

(i) SEQUENCE CHARACTERISTICS:
(A) LENGTH: 342 amino acids
(B) TYPE: amino acid
(C) STRANDEDNESS: single
(D) TOPOLOGY: linear (ii) MOLECULE TYPE: protein (iii) HYPOTHETICAL: NO (vi) ORIGINAL SOURCE:
(A) ORGANISM: pigtail macaque (xi) SEQUENCE DESCRIPTION: SEQ ID NO: 6:

```
Met Ala Glu His Asp Tyr His Glu Asp Tyr Gly Leu Asn Ser Phe As
1               5                   10                  15

Asp Ser Ser Gln Glu Glu His Gln Asp Phe Leu Gln Phe Arg Lys Va
                20                  25                  30

Phe Leu Pro Cys Met Tyr Leu Val Val Phe Val Cys Gly Leu Val Gl
            35                  40                  45

Asn Ser Leu Val Leu Val Ile Ser Ile Phe Tyr His Lys Leu Gln Se
        50                  55                  60

Leu Thr Asp Val Phe Leu Val Asn Leu Pro Leu Ala Asp Leu Val Ph
65                  70                  75                  80

Val Cys Thr Leu Pro Phe Trp Ala Tyr Ala Gly Ile His Glu Trp Il
                85                  90                  95

Phe Gly Gln Val Met Cys Lys Thr Leu Leu Gly Val Tyr Thr Ile As
                100                 105                 110

Phe Tyr Thr Ser Met Leu Ile Leu Thr Cys Ile Thr Val Asp Arg Ph
```

```
            115                 120                     125
        Ile Val Val Lys Ala Thr Lys Ala Tyr Asn Gln Gln Ala Lys Ar
            130                 135                 140
        Met Thr Trp Gly Lys Val Ile Cys Leu Leu Ile Trp Val Ile Ser Le
        145                 150                 155                 160
        Leu Val Ser Leu Pro Gln Ile Ile Tyr Gly Asn Val Phe Asn Leu As
                        165                 170                 175
        Lys Leu Ile Cys Gly Tyr His Asp Lys Glu Ile Ser Thr Val Val Le
                    180                 185                 190
        Ala Thr Gln Met Thr Leu Gly Phe Phe Leu Pro Leu Leu Ala Met Il
                195                 200                 205
        Val Cys Tyr Ser Val Ile Ile Lys Thr Leu Leu His Ala Gly Gly Ph
        210                 215                 220
        Gln Lys His Arg Ser Leu Lys Ile Ile Phe Leu Val Met Ala Val Ph
        225                 230                 235                 240
        Leu Leu Thr Gln Thr Pro Phe Asn Leu Val Lys Leu Ile Arg Ser Th
                        245                 250                 255
        His Trp Glu Tyr Tyr Ala Met Thr Ser Phe His Tyr Thr Ile Ile Va
                    260                 265                 270
        Thr Glu Ala Ile Ala Tyr Leu Arg Ala Cys Leu Asn Pro Val Leu Ty
                275                 280                 285
        Ala Phe Val Ser Leu Lys Phe Arg Lys Asn Phe Trp Lys Leu Val Ly
        290                 295                 300
        Asp Ile Gly Cys Leu Pro Tyr Leu Gly Val Ser His Gln Trp Lys Se
        305                 310                 315                 320
        Ser Glu Asp Asn Ser Lys Thr Phe Ser Ala Ser His Asn Val Glu Al
                        325                 330                 335
        Thr Ser Met Phe Gln Leu
                    340

(2) INFORMATION FOR SEQ ID NO: 7:

(i) SEQUENCE CHARACTERISTICS:
        (A) LENGTH: 1083 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO: 7:

ATGGACCCAG AAGAAACTTC AGTTTATTTG GATTATTACT ATGCTACGAG CCCAAACTCT60

GACATCAGGG AGACCCACTC CCATGTTCCT TACACCTCTG TCTTCCTTCC AGTCTTTTA120

ACAGCTGTGT TCCTGACTGG AGTGCTGGGG AACCTTGTTC TCATGGGAGC GTTGCATTT180

AAACCCGGCA GCCGAAGACT GATCGACATC TTTATCATCA ATCTGGCTGC CTCTGACTT240

ATTTTTCTTG TCACATTGCC CTCTCTGGGTG GATAAAGAAG CATCTCTAGG ACTGTGGAG300

ACGGGCTCCT TCCTGTGCAA AGGGAGCTCC TACATGATCT CCGTCAATAT GCACTGCAG360

GTCCTCCTGC TCACTTGCAT GAGTGTTGAC CGCTACCTGG CCATTGTGTG GCCAGTCGT420

TCCAGGAAAT TCAGAAGGAC AGACTGTGCA TATGTAGTCT GTGCCAGCAT CTGGTTTAT480

TCCTGCCTGC TGGGGTTGCC TACTCTTCTG TCCAGGGAGC TCACGCTGAT TGATGATAA540
```

-continued

```
CCATACTGTG CAGAGAAAAA GGCAACTCCA ATTAAACTCA TATGGTCCCT GGTGGCCTT  600
ATTTTCACCT TTTTTGTCCC TTTGTTGAGC ATTGTGACCT GCTACTGTTG CATTGCAAG  660
AAGCTGTGTG CCCATTACCA GCAATCAGGA AAGCACAACA AAAAGCTGAA GAAATCTAT  720
AAGATCATCT TTATTGTCGT GGCAGCCTTT CTTGTCTCCT GGCTGCCCTT CAATACTTT  780
AAGTTCCTGG CCATTGTCTC TGGGTTGCGG CAAGAACACT ATTTACCCTC AGCTATTCT  840
CAGCTTGGTA TGGAGGTGAG TGGACCCTTG GCATTTGCCA ACAGCTGTGT CAACCCTTT  900
ATTTACTATA TCTTCGACAG CTACATCCGC CGGGCCATTG TCCACTGCTT GTGCCCTTG  960
CTGAAAAACT ATGACTTTGG GAGTAGCACT GAGACATCAG ATAGTCACCT CACTAAGG  1020
CTCTCCACCT TCATTCATGC AGAAGATTTT GCCAGGAGGA GGAAGAGGTC TGTGTCAC  1080
TAA                                                              1083
```

(2) INFORMATION FOR SEQ ID NO: 8:

(i) SEQUENCE CHARACTERISTICS:
        (A) LENGTH: 360 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO: 8:

```
Met Asp Pro Glu Glu Thr Ser Val Tyr Leu Asp Tyr Tyr Ala Th
 1               5                  10                  15

Ser Pro Asn Ser Asp Ile Arg Glu Thr His Ser His Val Pro Tyr Th
                20                  25                  30

Ser Val Phe Leu Pro Val Phe Tyr Thr Ala Val Phe Leu Thr Gly Va
            35                  40                  45

Leu Gly Asn Leu Val Leu Met Gly Ala Leu His Phe Lys Pro Gly Se
50                  55                  60

Arg Arg Leu Ile Asp Ile Phe Ile Ile Asn Leu Ala Ala Ser Asp Ph
65                  70                  75                  80

Ile Phe Leu Val Thr Leu Pro Leu Trp Val Asp Lys Glu Ala Ser Le
                85                  90                  95

Gly Leu Trp Arg Thr Gly Ser Phe Leu Cys Lys Gly Ser Ser Tyr Me
                100                 105                 110

Ile Ser Val Asn Met His Cys Ser Val Leu Leu Leu Thr Cys Met Se
            115                 120                 125

Val Asp Arg Tyr Leu Ala Ile Val Trp Pro Val Val Ser Arg Lys Ph
        130                 135                 140

Arg Arg Thr Asp Cys Ala Tyr Val Val Cys Ala Ser Ile Trp Phe Il
145                 150                 155                 160

Ser Cys Leu Leu Gly Leu Pro Thr Leu Leu Ser Arg Glu Leu Thr Le
                165                 170                 175

Ile Asp Asp Lys Pro Tyr Cys Ala Glu Lys Lys Ala Thr Pro Ile Ly
            180                 185                 190

Leu Ile Trp Ser Leu Val Ala Leu Ile Phe Thr Phe Phe Val Pro Le
        195                 200                 205

Leu Ser Ile Val Thr Cys Tyr Cys Cys Ile Ala Arg Lys Leu Cys Al
```

```
                210              215              220
    His Tyr Gln Gln Ser Gly Lys His Asn Lys Lys Leu Lys Lys Ser Il
    225                 230                 235                 240

Lys Ile Ile Phe Ile Val Val Ala Ala Phe Leu Val Ser Trp Leu Pr
                    245                 250                 255

Phe Asn Thr Phe Lys Phe Leu Ala Ile Val Ser Gly Leu Arg Gln Gl
                    260                 265                 270

His Tyr Leu Pro Ser Ala Ile Leu Gln Leu Gly Met Glu Val Ser Gl
                275                 280                 285

Pro Leu Ala Phe Ala Asn Ser Cys Val Asn Pro Phe Ile Tyr Tyr Il
                290                 295                 300

Phe Asp Ser Tyr Ile Arg Arg Ala Ile Val His Cys Leu Cys Pro Cy
    305                 310                 315                 320

Leu Lys Asn Tyr Asp Phe Gly Ser Ser Thr Glu Thr Ser Asp Ser Hi
                    325                 330                 335

Leu Thr Lys Ala Leu Ser Thr Phe Ile His Ala Glu Asp Phe Ala Ar
                    340                 345                 350

Arg Arg Lys Arg Ser Val Ser Leu
                    355                 360
```

(2) INFORMATION FOR SEQ ID NO: 9:

(i) SEQUENCE CHARACTERISTICS:
        (A) LENGTH: 1083 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: African Green Monkey (xi) SEQUENCE DESCRIPTION: SEQ ID NO: 9:

```
ATGGACCCAG AAGAAACTTC AGTTTATTTG GATTATTACT ATGCTACAAG CCCAAACCCG 60

GACATCAGGG AGACCCACTC CCATGTTCCT TACACCTCTG TCTTCCTTCC AGTCTTTTA 120

ATAGCTGTGT TCCTGACTGG AGTGCTGGGG AACCTTGTTC TCATGGGAGC GTTGCATTT 180

AAACCCGGCA GCCGAAGACT GATCGACATC TTTATCATCA ATCTGGCTGC CTCTGACTT 240

ATTTTCCTTG TCACGTTGCC CTCTCTGGTG GATAAAGAAG CATCTTTAGG ACTGTGGAG 300

ACGGGCTCCT TCCTGTGCAA AGGGAGCTCC TACATGATCT CCGTCAATAT GCACTGCAG 360

GTCTTCCTGC TCACTTGCAT GAGTGTTGAC CGCTACCTGG CCATTGTGTG CCCAGTCGT 420

TCCAGGAAAT TCAGAAGGAC AGACTGTGCA TATGTAGTTT GCGCCAGCAT CTGGTTTAT 480

TCCTGCCTGC TGGGGTTGCC TACTCTTCTG TCCAGGGAGC TCACGCTGAT TGATGATAA 540

CCATACTGTG CAGAGAAAAA GGCAACTCCA CTTAAACTCA TATGGTCCCT GGTGGCCTT 600

ATTTTCACTT TTTTTGTCCC TTTGTTGAGC ATTGTGACCT GCTACTGTCG CATTGCAAG 660

AAGCTGTGTG CCCATTACCA GCAGTCAGGA AAGCACAACA AAAAGCTGAA GAAATCTAT 720

AAGATCATCT TTATCGTCGT GGCAGCCTTT CTTGTCTCCT GGCTGCCCTT CAATACTTC 780

AAGCTCCTGG CCATTGTCTC TGGGTTGCAG CAAGAACGCT ATTTTCCCTC AGCCATTCT 840

CAGCTTGGTA TGGAGGTGAG TGGACCCTTG GCATTTGCCA ACAGCTGTGT CAACCCTTT 900

ATTTACTATA TCTTCGACAG CTACATCCGC CGGGCTATTG TCCACTGCTT GTGCCCTTG 960
```

-continued

```
CTGAAAAACT ATGACTTTGG GAGTAGCACC GAGACATCAG ATAGTCACCT CACTAAGG 1020

CTCTCCACCT TCATTCATGC AGAAGATTTT ACCAGGAGGA GGAAGAGGTC TGTGTCAC 1080

TAA                                                          1083
```

(2) INFORMATION FOR SEQ ID NO: 10:

(i) SEQUENCE CHARACTERISTICS:
        (A) LENGTH: 360 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
       (A) ORGANISM: African Green Monkey (xi) SEQUENCE DESCRIPTION: SEQ ID NO: 10:

```
Met Asp Pro Glu Glu Thr Ser Val Tyr Leu Asp Tyr Tyr Ala Th
 1               5                  10                  15

Ser Pro Asn Pro Asp Ile Arg Glu Thr His Ser His Val Pro Tyr Th
                20                  25                  30

Ser Val Phe Leu Pro Val Phe Tyr Ile Ala Val Phe Leu Thr Gly Va
            35                  40                  45

Leu Gly Asn Leu Val Leu Met Gly Ala Leu His Phe Lys Pro Gly Se
    50                  55                  60

Arg Arg Leu Ile Asp Ile Phe Ile Ile Asn Leu Ala Ala Ser Asp Ph
65                  70                  75                  80

Ile Phe Leu Val Thr Leu Pro Leu Trp Val Asp Lys Glu Ala Ser Le
                85                  90                  95

Gly Leu Trp Arg Thr Gly Ser Phe Leu Cys Lys Gly Ser Ser Tyr Me
            100                 105                 110

Ile Ser Val Asn Met His Cys Ser Val Phe Leu Leu Thr Cys Met Se
        115                 120                 125

Val Asp Arg Tyr Leu Ala Ile Val Cys Pro Val Val Ser Arg Lys Ph
    130                 135                 140

Arg Arg Thr Asp Cys Ala Tyr Val Val Cys Ala Ser Ile Trp Phe Il
145                 150                 155                 160

Ser Cys Leu Leu Gly Leu Pro Thr Leu Leu Ser Arg Glu Leu Thr Le
                165                 170                 175

Ile Asp Asp Lys Pro Tyr Cys Ala Glu Lys Ala Thr Pro Leu Ly
            180                 185                 190

Leu Ile Trp Ser Leu Val Ala Leu Ile Phe Thr Phe Phe Val Pro Le
        195                 200                 205

Leu Ser Ile Val Thr Cys Tyr Cys Arg Ile Ala Arg Lys Leu Cys Al
    210                 215                 220

His Tyr Gln Gln Ser Gly Lys His Asn Lys Lys Leu Lys Lys Ser Il
225                 230                 235                 240

Lys Ile Ile Phe Ile Val Val Ala Ala Phe Leu Val Ser Trp Leu Pr
                245                 250                 255

Phe Asn Thr Ser Lys Leu Leu Ala Ile Val Ser Gly Leu Gln Gln Gl
            260                 265                 270

Arg Tyr Phe Pro Ser Ala Ile Leu Gln Leu Gly Met Glu Val Ser Gl
        275                 280                 285

Pro Leu Ala Phe Ala Asn Ser Cys Val Asn Pro Phe Ile Tyr Tyr Il
```

```
                    290              295               300
        Phe Asp Ser Tyr Ile Arg Arg Ala Ile Val His Cys Leu Cys Pro Cy
        305                 310                 315                 320

Leu Lys Asn Tyr Asp Phe Gly Ser Ser Thr Glu Thr Ser Asp Ser Hi
                        325                 330                 335

Leu Thr Lys Ala Leu Ser Thr Phe Ile His Ala Glu Asp Phe Thr Ar
                        340                 345                 350

Arg Arg Lys Arg Ser Val Ser Leu
                        355             360
```

(2) INFORMATION FOR SEQ ID NO: 11:

(i) SEQUENCE CHARACTERISTICS:
        (A) LENGTH: 1083 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: pigtail macaque (xi) SEQUENCE DESCRIPTION: SEQ ID NO: 11:

```
ATGGACCCAG AAGAAACTTC AGTTTATTTG GATTATTACT ATGCTACGAG CCCAAACCCG 60
GACATCAGGG AGACCCATTC CCATGTTCCT TACACCTCTG TCTTCCTTCC AGTCTTTTA 120
ACAGCTGTGT TCCTGACTGG AGTGCTGGGG AACCTTGTTC TCATGGGAGC GTTGCATTT 180
AAACCCGGCA GCCGAAGACT GATCGACATC TTTATCATCA ATCTGGCTGC CTCTGACTT 240
ATTTTCCTTG TCACGTTGCC CTCTCTGGGTG GATAAAGAAG CATCTTTAGG ACTGTGGAG 300
ACGGGCTCCT TCCTGTGCAA AGGGAGCTCC TACATGATCT CCGTCAATAT GCACTGCAG 360
GTCTTCCTGC TCACTTGCAT GAGTGTTGAC CGCTACCTGG CCATTGTGTG CCCAGTCGT 420
TCCAGGAAAT TCAGAAGGAC AGACTGTGCA TATGTAGTCT GTGCCAGCAT CTGGTTTAT 480
TCCTGCCTGC TGGGGTTGCC TACTCTTCTA TCCAGGGAGC TCACACTGAT TGATGATAA 540
CCATACTGTG CAGAGAAAAA GGCAACTCCA CTTAAACTCA TATGGTCCCT GGTGGCCTT 600
ATTTTCACCT TTTTTGTCCC TTTGTTGAGC ATTGTGACCT GCTACTGTTG CATTGCAAG 660
AAGCTGTGTG CCCATTACCA GCAGTCAGGA AAGCACAACA AAAAGCTGAA GAAATCTAT 720
AAGATCATCT TTATCGTCGT GGCAGCCTTT CTTGTCTCCT GGCTGCCCTT CAATACTTC 780
AAGCTCCTGG CCATTGTCTC TGGGTTGCAG CAAGAACGCT ATTTTCCCTC AGCCATTCT 840
CAGCTTGGTA TGGAGGTGAG TGGACCCTTG GCATTTGCCA ACAGCTGTGT CAACCCTTT 900
ATTTACTATA TCTTCGACAG CTACATCCGC CGGGCTATTG TCCACTGCTT GTGCCCTTG 960
CTGAAAAACT ATGACTTTGG GAGTAGCACC GAGACATCAG ATAGTCACCT CACTAAGG 1020
CTCTCCACCT TCATTCATGC AGAAGATTTT ACCAGGAGGA GGAAGAGGTC TGTGTCAC 1080
TAA                                                          1083
```

(2) INFORMATION FOR SEQ ID NO: 12:

(i) SEQUENCE CHARACTERISTICS:
        (A) LENGTH: 360 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
    (A) ORGANISM: pigtail macaque (xi) SEQUENCE DESCRIPTION: SEQ ID NO: 12:

```
Met Asp Pro Glu Glu Thr Ser Val Tyr Leu Asp Tyr Tyr Ala Th
 1               5                  10                  15

Ser Pro Asn Pro Asp Ile Arg Glu Thr His Ser His Val Pro Tyr Th
            20                  25                  30

Ser Val Phe Leu Pro Val Phe Tyr Thr Ala Val Phe Leu Thr Gly Va
        35                  40                  45

Leu Gly Asn Leu Val Leu Met Gly Ala Leu His Phe Lys Pro Gly Se
    50                  55                  60

Arg Arg Leu Ile Asp Ile Phe Ile Ile Asn Leu Ala Ala Ser Asp Ph
65                  70                  75                  80

Ile Phe Leu Val Thr Leu Pro Leu Trp Val Asp Lys Glu Ala Ser Le
                85                  90                  95

Gly Leu Trp Arg Thr Gly Ser Phe Leu Cys Lys Gly Ser Ser Tyr Me
                100                 105                 110

Ile Ser Val Asn Met His Cys Ser Val Phe Leu Leu Thr Cys Met Se
            115                 120                 125

Val Asp Arg Tyr Leu Ala Ile Val Cys Pro Val Val Ser Arg Lys Ph
        130                 135                 140

Arg Arg Thr Asp Cys Ala Tyr Val Val Cys Ala Ser Ile Trp Phe Il
145                 150                 155                 160

Ser Cys Leu Leu Gly Leu Pro Thr Leu Leu Ser Arg Glu Leu Thr Le
                165                 170                 175

Ile Asp Asp Lys Pro Tyr Cys Ala Glu Lys Lys Ala Thr Pro Leu Ly
            180                 185                 190

Leu Ile Trp Ser Leu Val Ala Leu Ile Phe Thr Phe Phe Val Pro Le
        195                 200                 205

Leu Ser Ile Val Thr Cys Tyr Cys Ile Ala Arg Lys Leu Cys Al
210                 215                 220

His Tyr Gln Gln Ser Gly Lys His Asn Lys Lys Leu Lys Lys Ser Il
225                 230                 235                 240

Lys Ile Ile Phe Ile Val Val Ala Ala Phe Leu Val Ser Trp Leu Pr
                245                 250                 255

Phe Asn Thr Ser Lys Leu Leu Ala Ile Val Ser Gly Leu Gln Gln Gl
            260                 265                 270

Arg Tyr Phe Pro Ser Ala Ile Leu Gln Leu Gly Met Glu Val Ser Gl
        275                 280                 285

Pro Leu Ala Phe Ala Asn Ser Cys Val Asn Pro Phe Ile Tyr Tyr Il
        290                 295                 300

Phe Asp Ser Tyr Ile Arg Arg Ala Ile Val His Cys Leu Cys Pro Cy
305                 310                 315                 320

Leu Lys Asn Tyr Asp Phe Gly Ser Ser Thr Glu Thr Ser Asp Ser Hi
            325                 330                 335

Leu Thr Lys Ala Leu Ser Thr Phe Ile His Ala Glu Asp Phe Thr Ar
        340                 345                 350

Arg Arg Lys Arg Ser Val Ser Leu
        355                 360
```

```
(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 13:

GGTGGACCAT TCTCTAGACT                                         20

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 14:

CCCTTTTTCT GGAGACTAAA T                                       21

(2) INFORMATION FOR SEQ ID NO: 15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 15:

CATCTGCTCT TTGGTGATG                                          19

(2) INFORMATION FOR SEQ ID NO: 16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 16:

GTATGGCTTA TCATCAATCA GC                                      22

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

-continued

```
    (ii) MOLECULE TYPE: other nucleic acid
        (A) DESCRIPTION: /desc = "primer"

(iii) HYPOTHETICAL: NO (xi) SEQUENCE DESCRIPTION: SEQ ID NO: 17:

CAGGCATCCA TGAATGGGTG T                                         21

(2) INFORMATION FOR SEQ ID NO: 18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 18:

CAAGGCCTAT AACTGGAACA TGCTG                                     25

(2) INFORMATION FOR SEQ ID NO: 19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 19:

GCTTGCTCAT TTGGGTG                                              17

(2) INFORMATION FOR SEQ ID NO: 20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 20:

CGCCGCGTCG ACCTTCTCTA AGTGTGGCAA GGC    33

1
```